(12) United States Patent
Brunstedt et al.

(10) Patent No.: US 9,175,271 B2
(45) Date of Patent: Nov. 3, 2015

(54) LIPID ACYLTRANSFERASE PROTEINS AND METHODS OF MAKING THEM

(75) Inventors: Janne Brunstedt, Roskilde (DK); Jens Frisbæk Sorensen, Aarhus (DK); Jørn Borch Søe, Tilst (DK); Charlotte Johansen Vedel, Holte (DK); Birgitte Ø. Wittschieben, Risskov (DK); Jørn Dalgaard Mikkelsen, Hvidovre (DK); Charlotte Horsmans Poulsen, Brabrand (DK); Lene B. Jensen, Højbjerg (DK); Lone B. Miller, Viby J (DK); Morten K. Larsen, Sabro (DK); Rikke H. Lorentzen, Randers (DK); Charlotte R. Thoudahl, Greve (DK); Marguerite A. Cervin, Redwood City, CA (US); Richard R. Bott, Burlingame, CA (US)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 716 days.

(21) Appl. No.: 13/444,302

(22) Filed: Apr. 11, 2012

(65) Prior Publication Data
US 2013/0034627 A1    Feb. 7, 2013

Related U.S. Application Data

(63) Continuation-in-part of application No. PCT/IB2009/054535, filed on Oct. 15, 2009.

(51) Int. Cl.
| | |
|---|---|
| C12N 9/10 | (2006.01) |
| C12N 15/00 | (2006.01) |
| C07H 21/04 | (2006.01) |
| C12N 1/20 | (2006.01) |
| A21D 8/02 | (2006.01) |
| A21D 10/00 | (2006.01) |

(52) U.S. Cl.
CPC ............... *C12N 9/1029* (2013.01); *A21D 8/02* (2013.01); *C12N 15/00* (2013.01); *A23V 2002/00* (2013.01)

(58) Field of Classification Search
CPC .. C12N 9/1029; C12N 15/00; A23V 2002/00; A21D 8/02
See application file for complete search history.

(56) References Cited

U.S. PATENT DOCUMENTS

| 6,344,328 B1 | 2/2002 | Short |
|---|---|---|
| 6,361,974 B1 | 3/2002 | Short et al. |
| 2002/0009518 A1 | 1/2002 | Soe |
| 2004/0091574 A1 | 5/2004 | Soe |
| 2005/0196766 A1 | 9/2005 | Soe |
| 2006/0078648 A1 | 4/2006 | De Kreij et al. |
| 2007/0026106 A1 | 2/2007 | De Kreij et al. |
| 2008/0063783 A1 | 3/2008 | De Kreij et al. |

FOREIGN PATENT DOCUMENTS

| EP | 1131416 | 9/2009 |
|---|---|---|
| WO | WO 02/06457 | 1/2002 |
| WO | WO 02/14490 | 2/2002 |
| WO | WO 03/002810 | 1/2003 |
| WO | WO 2004/064537 | 8/2004 |
| WO | WO 2004/064987 | 8/2004 |
| WO | WO 2005/066347 | 7/2005 |
| WO | WO 2005/066351 | 7/2005 |
| WO | WO 2006/008508 | 1/2006 |
| WO | WO 2008/090395 | 7/2008 |
| WO | WO 2009/081094 | 7/2009 |

OTHER PUBLICATIONS

Branden et al. (Introduction to Protein Structure, Garland Publishing Inc., New York, p. 247, 1991.*
Copland et al. B2J4D2_NOSP7 UniProtKB Database—Jun. 2008.*
Brumlik, et al., Identification of the Catalytic Triad of the Lipase/Acyltransferase From *Aeromonas hydrophila*, Journal of Bacteriology (1996) vol. 178, No. 7, p. 2060-2064.
J. Thomas Buckley, Mechanism of Action of Bacterial Glycerophospholipid: Cholesterol Acyltransferase, Biochemistry (1983) vol. 22, p. 5490-5493.
Hilton, et al., Studies on the Reaction Mechanism of a Microbial Lipase/Acyltransferase Using Chemical Modification and Site-Directed Mutagenesis, Journal of Biological Chemistry (1991) vol. 266, No. 2, p. 997-1000.
Robertson, et al., Influence of Active Site and Tyrosine Modification on the Secretion and Activity of the *Aeromonas hydrophila* Lipse/Acyltransferase, Journal of Biological Chemistry (1994) vol. 269, No. 3, p. 2146-2150.
Julian Thornton, et al., Molecular Cloning of a Phospholipid-Cholesterol Acyltransferase From *Aeromonas hydrophila*. Sequence Homologies With Lecithin-Cholesterol Acyltransferase and Other Lipases, Biochimica et Biophysica Acta (1988) vol. 959, p. 153-159.
Upton, et al., A New Family of Lipolytic Enzymes? TIBS (1995) Vo. 20, No. 5, p. 178-179.

* cited by examiner

*Primary Examiner* — Yong Pak
(74) *Attorney, Agent, or Firm* — Vedder Price P.C.; Thomas J. Kowalski; Mark W. Russell

(57) ABSTRACT

The present invention provides a method for preparing a variant lipid acyltransferase enzyme by expressing a nucleotide sequence encoding a lipid acyltransferase which may comprise at least one modification at a position(s) which corresponds in the encoded amino acid sequence to an amino acid(s) located in a) the canyon region of the enzyme (i.e. preferably amino acid residues 31, 27, 85, 86, 119, and 120); and/or b) insertion site 1 (i.e. amino acid residues 22-36) and/or c) insertion site 2 (i.e. amino acid residues 74-88), wherein the canyon region, insertion site 1 and/or insertion site 2 are defined as that region which when aligned based on primary or tertiary structure corresponds to the canyon region, insertion site 1 or insertion site 2 (or the corresponding amino acid residues taught above) of the enzyme shown herein as SEQ ID No. 16 or 6 in a host organism.

9 Claims, 42 Drawing Sheets

FIGURE 1

SEQ ID No. 6

```
  1   ADTRPAFSRI VMFGDSLSDT GKMYSKMRGY LPSSPPYYEG RFSNGPVWLE QLTKQFPGLT
 61   IANEAEGGAT AVAYNKISWD PKYQVINNLD YEVTQFLQKD SFKPDDLVIL WVGANDYLAY
121   GWNTEQDAKR VRDAISDAAN RMVLNGAKQI LLFNLPDLGQ NPSARSQKVV EAVSHVSAYH
181   NKLLLNLARQ LAPTGMVKLF EIDKQFAEML RDPQNFGLSD VENPCYDGGY VWKPFATRSV
241   STDRQLSAFS PQERLAIAGN PLLAQAVASP MARRSASPLN CEGKMFWDQV HPTTVVHAAL
301   SERAATFIET QYEFLAHG
```

FIGURE 2

(SEQ ID No. 1)

```
  1   MKKWFVCLLG LVALTVQAAD SRPAFSRIVM FGDSLSDTGK MYSKMRGYLP
 51   SSPPYYEGRF SNGPVWLEQL TKQFPGLTIA NEAEGGATAV AYNKISWNPK
101   YQVINNLDYE VTQFLQKDSF KPDDLVILWV GANDYLAYGW NTEQDAKRVR
151   DAISDAANRM VLNGAKQILL FNLPDLGQNP SARSQKVVEA VSHVSAYHNQ
201   LLLNLARQLA PTGMVKLFEI DKQFAEMLRD PQNFGLSDVE NPCYDGGYVW
251   KPFATRSVST DRQLSAFSPQ ERLAIAGNPL LAQAVASPMA RRSASPLNCE
301   GKMFWDQVHP TTVVHAALSE RAATFIANQY EFLAH*
```

FIGURE 3

(SEQ ID No. 2)

```
  1 ivafGD1Td  geayygdsdg  ggwgagladr  Ltallrlrar  prgvdvfnrg  isGrtsdGrl
 61 ivDalvallF  laqslglpnL  pPYLsgdflr  GANFAsagAt  Ilptsgpfli  QvqFkdfksq
121 vlelrqalgl  lqellrllpv  ldakspdlvt  imiGtNDlit  saffgpkste  sdrnvsvpef
181 kdnlrqlikr  Lrsnngarii  vlitlvilnl  gplGClPlkl  alalassknv  dasgclerln
241 eavadfneal  relaiskled  qlrkdglpdv  kgadvpyvDl  ysifqdldgi  qnpsayvyGF
301 ettkaCCGyG  gryNynrvCG  naglcnvtak  aCnpssylls  flfwgfips   ekGykavAea
361 l
```

FIGURE 4

(SEQ ID No. 3)

```
  1 mkkwfvcllg  lvaltvqaad  srpafsrivm  fgdslsdtgk  myskmrgylp  ssppyyegrf
 61 sngpvwleql  tnefpgltia  neaeggptav  aynkiswnpk  yqvinnldye  vtqflqkdsf
121 kpddlvilwv  gandylaygw  nteqdakrvr  daisdaanrm  vlngakeill  fnlpdlgqnp
181 sarsqkvvea  ashvsayhnq  lllnlarqla  ptgmvklfei  dkqfaemlrd  pqnfglsdqr
241 nacyggsyvw  kpfasrsast  dsqlsafnpq  erlaiagnpl  laqavaspma  arsastlnce
301 gkmfwdqvhp  ttvvhaalse  paatfiesqy  eflah
```

FIGURE 5

SEQ ID No. 4

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydgqyvw kpfatrsvst drqlsafspq erlaiagnpl laqavaspma rrsasplnce
301 gkmfwdqvhp ttvvhaalse raatfietqy eflahg
```

FIGURE 6 (SEQ ID No. 5)

```
  1 MKKWFVCLLG LIALTVQAAD TRPAFSRIVM FGDSLSDTGK MYSKMRGYLP
 51 SSPPYYEGRF SNGPVWLEQL TKQFPGLTIA NEAEGGATAV AYNKISWNPK
101 YQVINNLDYE VTQFLQKDSF KPDDLVILWV GANDYLAYGW NTEQDAKRVR
151 DAISDAANRM VLNGAKQILL FNLPDLGQNP SARSQKVVEA VSHVSAYHNK
201 LLLNLARQLA PTGMVKLFEI DKQFAEMLRD PQNFGLSDVE NPCYDGGYVW
251 KPFATRSVST DRQLSAFSPQ ERLAIAGNPL LAQAVASPMA RRSASPLNCE
301 GKMFWDQVHP TTVVHAALSE RAATFIETQY EFLAHG*
```

FIGURE 7    (SEQ ID No. 7)

```
  1 MFKFKKNFLV GLSAALMSIS LFSATASAAS ADSRPAFSRI VMFGDSLSDT
 51 GKMYSKMRGY LPSSPPYYEG RFSNGPVWLE QLTKQFPGLT IANEAEGGAT
101 AVAYNKISWN PKYQVINNLD YEVTQFLQKD SFKPDDLVIL WVGANDYLAY
151 GWNTEQDAKR VRDAISDAAN RMVLNGAKQI LLFNLPDLGQ NPSARSQKVV
201 EAVSHVSAYH NQLLLNLARQ LAPTGMVKLF EIDKQFAEML RDPQNFGLSD
251 VENPCYDGGY VWKPFATRSV STDRQLSAFS PQERLAIAGN PLLAQAVASP
301 MARRSASPLN CEGKMFWDQV HPTTVVHAAL SERAATFIAN QYEFLAH**
```

FIGURE 8

(SEQ ID No. 8)

```
ADSRPAFSRIVMFGDSLSDTGKMYSKMRGYLPSSPPYYEGRFSNGPVWLEQLTNEFPGLTIANEAEGGPT
AVAYNKISWNPKYQVINNLDYEVTQFLQKDSFKPDDLVILWVGANDYLAYGWNTEQDAKRVRDAISDAAN
RMVLNGAKEILLFNLPDLGQNPSARSQKVVEAASHVSAYHNQLLLNLARQLAPTGMVKLFEIDKQFAEML
RDPQNFGLSDQRNACYGGSYVWKPFASRSASTDSQLSAFNPQERLAIAGNPLLAQAVASPMAARSASTLN
CE
GKMFWDQVHPTTVVHAALSEPAATFIESQYEFLAH
```

FIGURE 9

(SEQ ID No. 9)

```
  1  ADTRPAFSRI VMFGDSLSDT GKMYSKMRGY LPSSPPYYEG RFSNGPVWLE QLTKQFPGLT
 61  IANEAEGGAT AVAYNKISWN PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

```
                       10        20        30        40        50        60
              ....*....|....*....|....*....|....*....|....*....|....*....|
1IVN_A      4 LLILGDSLSAG--------------------YRMSASAAWPALLNDKWqsk----------- 34
P10480     28 IVMFGDSLSDTgkmyskmrgylpssppyyeGRFSNGPVWLEQLTNEFPGLTianeaeggp 87

70        80        90       100       110       120
              ....*....|....*....|....*....|....*....|....*....|....*....|
1IVN_A     35 -tsvVNASISGDT-------------------------SQQGLARLPALLKQHQPRW 65
P10480     88 tavaYNKISWNPKyq------------------------vINNLDYEVTQFLQKDSFKPDDL 125

130       140       150       160       170       180
              ....*....|....*....|....*....|....*....|....*....|....*....|
1IVN_A     66 VLVELGGNDG-----------------------------------LRGFQPQQTEQT 87
P10480    126 VILWVGANDY--------------------------------LA---YGWNTEQDAKRVRDA 152

190       200       210       220       230       240
              ....*....|....*....|....*....|....*....|....*....|....*....|
1IVN_A     88 LRQILQDVKaANAEPilmqiRLPANYGR--------------------------------- 115
P10480    153 ISDAANRMV-LNGAK------EILLFNLPdlg-------------------------qnP 180

250       260       270       280       290       300
              ....*....|....*....|....*....|....*....|....*....|....*....|
1IVN_A    116 ---------------RYNEAFSAIYPKLAke---------------------fDVPLLPFFME 142
P10480    181 SARSQKVVEAASHVSAYHNQLLLNLArqlaptg----------mvklfeiDKQFAEMLRD 230

310       320       330       340       350       360
              ....*....|....*....|....*....|....*....|....*....|....*....|
1IVN_A    143 EVYLKPQW----------------------------------------------------- 150
P10480    231 PQNFGLSDQRNacyggsyvwkpfasrsastdsqlsafnpqerlaiagnpllaqavaspma 290

370       380       390       400
              ....*....|....*....|....*....|....*....|
1IVN_A    151 ------------MQDDGI---------HPNRDAQPFIADWM 170
P10480    291 arsastlncegkMFWDQV---------HPTTVVHAALSEPA 322
```

FIGURE 17

```
                  1                                                50
P10480      (1)   MKKWFVCLLGLVALTVQAADSRPAFSRIVMFGDSLSDTGKMYSKMRGYLP
A. sal      (1)   ------------------ADTRPAFSRIVMFGDSLSDTGKMYSKMRGYLP
A. hyd      (1)   ------------------ADSRPAFSRIVMFGDSLSDTGKMYSKMRGYLP
Consensus   (1)                     AD*RPAFSRIVMFGDSLSDTGKMYSKMRGYLP
                  51                                               100
P10480      (51)  SSPPYYEGRFSNGPVWLEQLTNEFPGLTIANEAEGGPTAVAYNKISWNPK
A. sal      (33)  SSPPYYEGRFSNGPVWLEQLTKQFPGLTIANEAEGGATAVAYNKISWNPK
A. hyd      (33)  SSPPYYEGRFSNGPVWLEQLTKQFPGLTIANEAEGGATAVAYNKISWNPK
Consensus   (51)  SSPPYYEGRFSNGPVWLEQLT**FPGLTIANEAEGG*TAVAYNKISWNPK
                  101                                              150
P10480      (101) YQVINNLDYEVTQFLQKDSFKPDDLVILWVGANDYLAYGWNTEQDAKRVR
A. sal      (83)  YQVINNLDYEVTQFLQKDSFKPDDLVILWVGANDYLAYGWNTEQDAKRVR
A. hyd      (83)  YQVINNLDYEVTQFLQKDSFKPDDLVILWVGANDYLAYGWNTEQDAKRVR
Consensus   (101) YQVINNLDYEVTQFLQKDSFKPDDLVILWVGANDYLAYGWNTEQDAKRVR
                  151                                              200
P10480      (151) DAISDAANRMVLNGAKEILLFNLPDLGQNPSARSQKVVEAASHVSAYHNQ
A. sal      (133) DAISDAANRMVLNGAKQILLFNLPDLGQNPSARSQKVVEAVSHVSAYHNK
A. hyd      (133) DAISDAANRMVLNGAKQILLFNLPDLGQNPSARSQKVVEAVSHVSAYHNQ
Consensus   (151) DAISDAANRMVLNGAK*ILLFNLPDLGQNPSARSQKVVEA*SHVSAYHN*
                  201                                              250
P10480      (201) LLLNLARQLAPTGMVKLFEIDKQFAEMLRDPQNFGLSDQRNACYGGSYVW
A. sal      (183) LLLNLARQLAPTGMVKLFEIDKQFAEMLRDPQNFGLSDVENPCYDGGYVW
A. hyd      (183) LLLNLARQLAPTGMVKLFEIDKQFAEMLRDPQNFGLSDVENPCYDGGYVW
Consensus   (201) LLLNLARQLAPTGMVKLFEIDKQFAEMLRDPQNFGLSD**N*CY*G*YVW
                  251                                              300
P10480      (251) KPFASRSASTDSQLSAFNPQERLAIAGNPLLAQAVASPMAARSASTLNCE
A. sal      (233) KPFATRSVSTDRQLSAFSPQERLAIAGNPLLAQAVASPMARRSASPLNCE
A. hyd      (233) KPFATRSVSTDRQLSAFSPQERLAIAGNPLLAQAVASPMARRSASPLNCE
Consensus   (251) KPFA*RS*STD*QLSAF*PQERLAIAGNPLLAQAVASPMA*RSAS*LNCE
                  301                         336
P10480      (301) GKMFWDQVHPTTVVHAALSEPAATFIESQYEFLAH-
A. sal      (283) GKMFWDQVHPTTVVHAALSERAATFIETQYEFLAHG
A. hyd      (283) GKMFWDQVHPTTVVHAALSERAATFIANQYEFLAH-
Consensus   (301) GKMFWDQVHPTTVVHAALSE*AATFI**QYEFLAH*
```

FIGURE 18

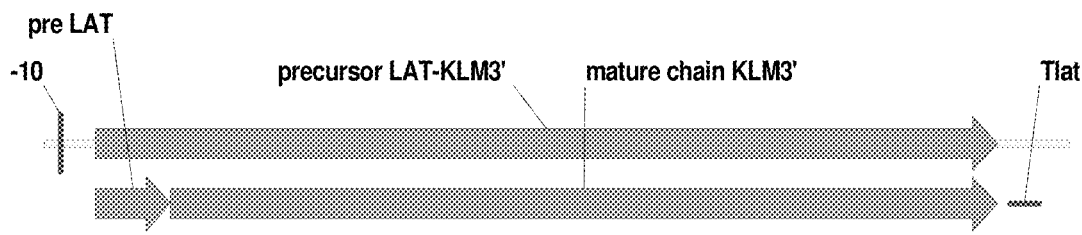

Gene construct for KLM3' expression 1182 bp

FIGURE 20

```
                                                   -35
   1 GCTTTTCTTT TGGAAGAAAA TATAGGGAAA ATGGTACTTG TTAAAAATTC GGAATATTTA
     CGAAAAGAAA ACCTTCTTTT ATATCCCTTT TACCATGAAC AATTTTTAAG CCTTATAAAT
     -10                                           M  K  Q  Q  K  R  L ·
  61 TACAATATCA TATGTTTCAC ATTGAAAGGG GAGGAGAATC ATGAAACAAC AAAAACGGCT
     ATGTTATAGT ATACAAAGTG TAACTTTCCC CTCCTCTTAG TACTTTGTTG TTTTTGCCGA
     · Y  A  R  L  L  T  L  L  F  A  L  I  F  L  L  P  H  S  A  A ·
 121 TTACGCCCGA TTGCTGACGC TGTTATTTGC GCTCATCTTC TTGCTGCCTC ATTCTGCAGC
     AATGCGGGCT AACGACTGCG ACAATAAACG CGAGTAGAAG AACGACGGAG TAAGACGTCG
     · S  A  A  D  T  R  P  A  F  S  R  I  V  M  F  G  D  S  L  S ·
 181 TTCAGCAGCA GATACAAGAC CGGCGTTTAG CCGGATCGTC ATGTTTGGAG ATAGCCTGAG
     AAGTCGTCGT CTATGTTCTG GCCGCAAATC GGCCTAGCAG TACAAACCTC TATCGGACTC
     · D  T  G  K  M  Y  S  K  M  R  G  Y  L  P  S  S  P  Y  Y ·
 241 CGATACGGGC AAAATGTATA GCAAAATGAG AGGCTATCTT CCGTCAAGCC CGCCGTATTA
     GCTATGCCCG TTTTACATAT CGTTTTACTC TCCGATAGAA GGCAGTTCGG GCGGCATAAT
     · E  G  R  F  S  N  G  P  V  W  L  E  Q  L  T  K  Q  F  P  G ·
 301 TGAAGGCCGC TTTAGCAATG GACCGGTCTG GCTGGAACAA CTGACGAAAC AATTTCCGGG
     ACTTCCGGCG AAATCGTTAC CTGGCCAGAC CGACCTTGTT GACTGCTTTG TTAAAGGCCC
     · L  T  I  A  N  E  A  E  G  G  A  T  A  V  A  Y  N  K  I  S ·
 361 ACTGACGATC GCTAATGAAG CAGAAGGAGG AGCAACAGCG GTCGCCTATA ACAAAATCAG
     TGACTGCTAG CGATTACTTC GTCTTCCTCC TCGTTGTCGC CAGCGGATAT TGTTTTAGTC
     · W  D  P  K  Y  Q  V  I  N  N  L  D  Y  E  V  T  Q  F  L  Q ·
 421 CTGGGACCCG AAATATCAGG TCATCAACAA CCTGGACTAT GAAGTCACAC AGTTTCTTCA
     GACCCTGGGC TTTATAGTCC AGTAGTTGTT GGACCTGATA CTTCAGTGTG TCAAAGAAGT
     · K  D  S  F  K  P  D  D  L  V  I  L  W  V  G  A  N  D  Y  L ·
 481 GAAAGACAGC TTTAAACCGG ATGATCTGGT CATCCTTTGG GTCGGCGCCA ATGATTATCT
     CTTTCTGTCG AAATTTGGCC TACTAGACCA GTAGGAAACC CAGCCGCGGT TACTAATAGA
     · A  Y  G  W  N  T  E  Q  D  A  K  R  V  R  D  A  I  S  D  A ·
 541 GGCGTATGGC TGGAACACAG AACAAGATGC CAAAAGAGTC AGAGATGCCA TCAGCGATGC
     CCGCATACCG ACCTTGTGTC TTGTTCTACG GTTTTCTCAG TCTCTACGGT AGTCGCTACG
     · A  N  R  M  V  L  N  G  A  K  Q  I  L  F  N  L  P  D  L ·
 601 CGCTAATAGA ATGGTCCTGA ACGGCGCCAA ACAAATCCTG CTGTTTAACC TGCCGGATCT
     GCGATTATCT TACCAGGACT TGCCGCGGTT TGTTTAGGAC GACAAATTGG ACGGCCTAGA
     · G  Q  N  P  S  A  R  S  Q  K  V  V  E  A  V  S  H  V  S  A ·
 661 GGGACAAAAT CCGAGCGCCA GAAGCCAAAA AGTCGTCGAA GCAGTCAGCC ATGTCAGCGC
     CCCTGTTTTA GGCTCGCGGT CTTCGGTTTT TCAGCAGCTT CGTCAGTCGG TACAGTCGCG
     · Y  H  N  K  L  L  L  N  L  A  R  Q  L  A  P  T  G  M  V  K ·
 721 CTATCATAAC AAAACTGCTG CTGAACCTGG CAAGACAATTG GCACCGACGG GAATGGTTAA
     GATAGTATTG TTTGACGACG ACTTGGACCG TTCTGTTAAC CGTGGCTGCC CTTACCAATT
     · L  F  E  I  D  K  Q  F  A  E  M  L  R  D  P  Q  N  F  G  L ·
 781 ATTGTTTGAA ATTGACAAAC AGTTTGCCGA AATGCTGAGA GATCCGCAAA ATTTTGGCCT
     TAACAAACTT TAACTGTTTG TCAAACGGCT TTACGACTCT CTAGGCGTTT TAAAACCGGA
     · S  D  V  E  N  P  C  Y  D  G  G  Y  V  W  K  P  F  A  T  R ·
 841 GAGCGATGTC GAAAACCCGT GCTATGATGG CGGATATGTC TGGAAACCGT TTGCCACAAG
     CTCGCTACAG CTTTTGGGCA CGATACTACC GCCTATACAG ACCTTTGGCA AACGGTGTTC
     · S  V  S  T  D  R  Q  L  S  A  F  S  P  Q  E  R  L  A  I  A ·
 901 AAGCGTCAGC ACGGATAGAC AACTGTCAGC GTTTAGCCCG CAAGAAAGAC TGGCAATCGC
     TTCGCAGTCG TGCCTATCTG TTGACAGTCG CAAATCGGGC GTTCTTTCTG ACCGTTAGCG
     · G  N  P  L  L  A  Q  A  V  A  S  P  M  A  R  R  S  A  S  P ·
 961 CGGAAATCCG CTTTTGGCAC AAGCAGTTGC TTCACCGATG GCAAGAAGAT CAGCAAGCCC
     GCCTTTAGGC GAAAACCGTG TTCGTCAACG AAGTGGCTAC CGTTCTTCTA GTCGTTCGGG
     · L  N  C  E  G  K  M  F  W  D  Q  V  H  P  T  I  V  H  A ·
1021 GCTGAATTGC GAAGGCAAAA TGTTTTGGGA TCAGGTCCAT CCGACAACAG TTGTCCATGC
     CGACTTAACG CTTCCGTTTT ACAAAACCCT AGTCCAGGTA GGCTGTTGTC AACAGGTACG
     · A  L  S  E  R  A  A  T  F  I  E  T  Q  Y  E  F  L  A  H  G ·
1081 TGCCCTTTCA GAAAGAGCGG CGACGTTTAT CGAAACACAG TATGAATTTC TGGCCCATGG
     ACGGGAAAGT CTTTCTCGCC GCTGCAAATA GCTTTGTGTC ATACTTAAAG ACCGGGTACC
     ·stop
1141 CTGAGTTAAC AGAGGACGGA TTTCCTGAAG GAAATCCGTT TTTTTATTTT AAGCTTGGAG
     GACTCAATTG TCTCCTGCCT AAAGGACTTC CTTTAGGCAA AAAATAAAA TTCGAACCTC
1201 ACAAGGTAAA GGATAAAACC TCGAG
     TGTTCCATTT CCTATTTTGG AGCTC
```

FIGURE 22 (SEQ ID No. 10)

```
   1  ATGAAACAAC AAAAACGGCT TTACGCCCGA TTGCTGACGC TGTTATTTGC
      TACTTTGTTG TTTTTGCCGA AATGCGGGCT AACGACTGCG ACAATAAACG

51  GCTCATCTTC TTGCTGCCTC ATTCTGCAGC TTCAGCAGCA GATACAAGAC
      CGAGTAGAAG AACGACGGAG TAAGACGTCG AAGTCGTCGT CTATGTTCTG

101  CGGCGTTTAG CCGGATCGTC ATGTTTGGAG ATAGCCTGAG CGATACGGGC
      GCCGCAAATC GGCCTAGCAG TACAAACCTC TATCGGACTC GCTATGCCCG

151  AAAATGTATA GCAAAATGAG AGGCTATCTT CCGTCAAGCC CGCCGTATTA
      TTTTACATAT CGTTTTACTC TCCGATAGAA GGCAGTTCGG GCGGCATAAT

201  TGAAGGCCGC TTTAGCAATG GACCGGTCTG GCTGGAACAA CTGACGAAAC
      ACTTCCGGCG AAATCGTTAC CTGGCCAGAC CGACCTTGTT GACTGCTTTG

251  AATTTCCGGG ACTGACGATC GCTAATGAAG CAGAAGGAGG AGCAACAGCG
      TTAAAGGCCC TGACTGCTAG CGATTACTTC GTCTTCCTCC TCGTTGTCGC

301  GTCGCCTATA CAAAATCAG CTGGGACCCG AAATATCAGG TCATCAACAA
      CAGCGGATAT GTTTTAGTC GACCCTGGGC TTTATAGTCC AGTAGTTGTT

351  CCTGGACTAT GAAGTCACAC AGTTTCTTCA GAAAGACAGC TTTAAACCGG
      GGACCTGATA CTTCAGTGTG TCAAAGAAGT CTTTCTGTCG AAATTTGGCC

401  ATGATCTGGT CATCCTTTGG GTCGGCGCCA ATGATTATCT GGCGTATGGC
      TACTAGACCA GTAGGAAACC CAGCCGCGGT TACTAATAGA CCGCATACCG

451  TGGAACACAG AACAAGATGC CAAAAGAGTC AGAGATGCCA TCAGCGATGC
      ACCTTGTGTC TTGTTCTACG GTTTTCTCAG TCTCTACGGT AGTCGCTACG

501  CGCTAATAGA ATGGTCCTGA ACGGCGCCAA ACAAATCCTG CTGTTTAACC
      GCGATTATCT TACCAGGACT TGCCGCGGTT TGTTTAGGAC GACAAATTGG

551  TGCCGGATCT GGGACAAAAT CCGAGCGCCA GAAGCCAAAA AGTCGTCGAA
      ACGGCCTAGA CCCTGTTTTA GGCTCGCGGT CTTCGGTTTT TCAGCAGCTT

601  GCAGTCAGCC ATGTCAGCGC CTATCATAAC AAACTGCTGC TGAACCTGGC
      CGTCAGTCGG TACAGTCGCG GATAGTATTG TTTGACGACG ACTTGGACCG

651  AAGACAATTG GCACCGACGG GAATGGTTAA ATTGTTTGAA ATTGACAAAC
      TTCTGTTAAC CGTGGCTGCC CTTACCAATT TAACAAACTT TAACTGTTTG

701  AGTTTGCCGA AATGCTGAGA GATCCGCAAA ATTTTGGCCT GAGCGATGTC
      TCAAACGGCT TTACGACTCT CTAGGCGTTT TAAAACCGGA CTCGCTACAG

751  GAAAACCCGT GCTATGATGG CGGATATGTC TGGAAACCGT TTGCCACAAG
      CTTTTGGGCA CGATACTACC GCCTATACAG ACCTTTGGCA AACGGTGTTC

801  AAGCGTCAGC ACGGATAGAC AACTGTCAGC GTTAGCCCG CAAGAAAGAC
      TTCGCAGTCG TGCCTATCTG TTGACAGTCG CAAATCGGGC GTTCTTTCTG

851  TGGCAATCGC CGGAAATCCG CTTTTGGCAC AAGCAGTTGC TTCACCGATG
      ACCGTTAGCG GCCTTAGGC GAAAACCGTG TTCGTCAACG AAGTGGCTAC

901  GCAAGAAGAT CAGCAAGCCC GCTGAATTGC GAAGGCAAAA TGTTTTGGGA
      CGTTCTTCTA GTCGTTCGGG CGACTTAACG CTTCCGTTTT ACAAAACCCT

951  TCAGGTCCAT CCGACAACAG TTGTCCATGC TGCCCTTTCA GAAAGAGCGG
      AGTCCAGGTA GGCTGTTGTC AACAGGTACG ACGGGAAAGT CTTTCTCGCC

1001  CGACGTTTAT CGAAACACAG TATGAATTTC TGGCCCATGG CTGA
      GCTGCAAATA GCTTTGTGTC ATACTTAAAG ACCGGGTACC GACT
```

FIGURE 23 (SEQ ID No. 11)

```
  1  ATGAAAAAAT GGTTTGTGTG TTTATTGGGA TTGGTCGCGC TGACAGTTCA GGCAGCCGAC
 61  AGCCGTCCCG CCTTCTCCCG GATCGTGATG TTTGGCGACA GCCTCTCCGA TACCGGCAAG
121  ATGTACAGCA AGATGCGCGG TTACCTCCCC TCCAGCCCCC CCTACTATGA GGGCCGCTTC
181  TCCAACGGGC CCGTCTGGCT GGAGCAGCTG ACCAACGAGT TCCCGGGCCT GACCATAGCC
241  AACGAGGCGG AAGGCGGACC GACCGCCGTG GCTTACAACA AGATCTCCTG GAATCCCAAG
301  TATCAGGTCA TCAACAACCT GGACTACGAG GTCACCCAGT TCCTGCAAAA AGACAGCTTC
361  AAGCCGGACG ATCTGGTGAT CCTCTGGGTC GGCGCCAACG ACTATCTGGC CTATGGCTGG
421  AACACAGAGC AGGATGCCAA GCGGGTGCGC GACGCCATCA GCGATGCGGC CAACCGCATG
481  GTGCTGAACG GCGCCAAGGA GATACTGCTG TTCAACCTGC GGATCTGGG CCAGAACCCC
541  TCGGCCCGCA GCCAGAAGGT GGTCGAGGCG GCCAGCCATG TCTCCGCCTA CCACAACCAG
601  CTGCTGCTGA ACCTGGCACG CCAGCTGGCT CCCACCGGCA TGGTGAAGCT GTTCGAGATC
661  GACAAGCAGT TGCCGAGAT GCTGCGTGAT CCGCAGAACT TCGGCCTGAG CGACCAGAGG
721  AACGCCTGCT ACGGTGGCAG CTATGTATGG AAGCCGTTTG CCTCCCGCAG CGCCAGCACC
781  GACAGCCAGC TCTCCGCCTT CAACCCGCAG GAGCGCCTCG CCATCGCCGG CAACCCGCTG
841  CTGGCCCAGG CCGTCGCCAG CCCCATGGCT GCCCGCAGCG CCAGCACCCT CAACTGTGAG
901  GGCAAGATGT CTGGGATCA GGTCCACCCC ACCACTGTCG TGCACGCCGC CCTGAGCGAG
961  CCCGCCGCCA CCTTCATCGA GAGCCAGTAC GAGTTCCTCG CCCAC
```

FIGURE 24 (SEQ ID No. 12)

```
  1  ATGAAAAAAT GGTTTGTTTG TTTATTGGGG TTGATCGCGC TGACAGTTCA GGCAGCCGAC
 61  ACTCGCCCCG CCTTCTCCCG GATCGTGATG TTCGGCGACA GCCTCTCCGA TACCGGCAAA
121  ATGTACAGCA AGATGCGCGG TTACCTCCCC TCCAGCCCGC CCTACTATGA GGGCCGTTTC
181  TCCAACGGAC CCGTCTGGCT GGAGCAGCTG ACCAAGCAGT TCCCGGGTCT GACCATCGCC
241  AACGAAGCGG AAGGCGGTGC CACTGCCGTG GCTTACAACA AGATCTCCTG GAATCCCAAG
301  TATCAGGTCT ACAACAACCT GGACTACGAG GTCACCCAGT TCTTGCAGAA AGACAGCTTC
361  AAGCCGGACG ATCTGGTGAT CCTCTGGGTC GGTGCCAATG ACTATCTGGC ATATGGCTGG
421  AATACGGAGC AGGATGCCAA GCGAGTTCGC GATGCCATCA GCGATGCGGC CAACCGCATG
481  GTACTGAACG GTGCCAAGCA GATACTGCTG TTCAACCTGC GGATCTGGG CCAGAACCCG
541  TCAGCCCGCA GTCAGAAGGT GGTCGAGGCG GTCAGCCATG TCTCCGCCTA TCACAACAAG
601  CTGCTGCTGA ACCTGGCACG CCAGCTGGCC CCCACCGGCA TGGTAAAGCT GTTCGAGATC
661  GACAAGCAAT TGCCGAGAT GCTGCGTGAT CCGCAGAACT TCGGCCTGAG CGACGTCGAG
721  AACCCCTGCT ACGACGGCGG CTATGTGTGG AAGCCGTTTG CCACCCGCAG CGTCAGCACC
781  GACAGCCAGC TCTCCGCCTT CAGTCCGCAG GAACGCCTCG CCATCGCCGG CAACCCGCTG
841  CTGGCACAGG CCGTTGCCAG TCCTATGGCC CGCCGCAGCG CCAGCCCCCT CAACTGTGAG
901  GGCAAGATGT CTGGGATCA GGTACACCCG ACCACTGTCG TGCACGCAGC CCTGAGCGAG
961  CGCGCCGCCA CCTTCATCGA GACCCAGTAC GAGTTCCTCG CCCACGGATG A
```

FIGURE 25 (SEQ ID No. 13)

```
   1  ATGAAAAAAT GGTTTGTGTG TTTATTGGGA TTGGTCGCGC TGACAGTTCA
      TACTTTTTTA CCAAACACAC AAATAACCCT AACCAGCGCG ACTGTCAAGT

51  GGCAGCCGAC AGTCGCCCCG CCTTTTCCCG GATCGTGATG TTCGGCGACA
      CCGTCGGCTG TCAGCGGGGC GGAAAAGGGC CTAGCACTAC AAGCCGCTGT

101  GCCTCTCCGA TACCGGCAAA ATGTACAGCA AGATGCGCGG TTACCTCCCC
      CGGAGAGGCT ATGGCCGTTT TACATGTCGT TCTACGCGCC AATGGAGGGG

151  TCCAGCCCGC CCTACTATGA GGGCCGTTTC TCCAACGGAC CCGTCTGGCT
      AGGTCGGGCG GGATGATACT CCCGGCAAAG AGGTTGCCTG GGCAGACCGA

201  GGAGCAGCTG ACCAAACAGT TCCCGGGTCT GACCATCGCC AACGAAGCGG
      CCTCGTCGAC TGGTTTGTCA AGGGCCCAGA CTGGTAGCGG TTGCTTCGCC

251  AAGGCGGTGC CACTGCCGTG GCTTACAACA AGATCTCCTG GAATCCCAAG
      TTCCGCCACG GTGACGGCAC CGAATGTTGT TCTAGAGGAC CTTAGGGTTC

301  TATCAGGTCA TCAACAACCT GGACTACGAG GTCACCCAGT TCTTGCAGAA
      ATAGTCCAGT AGTTGTTGGA CCTGATGCTC CAGTGGGTCA AGAACGTCTT

351  AGACAGCTTC AAGCCGGACG ATCTGGTGAT CCTCTGGGTC GGTGCCAATG
      TCTGTCGAAG TTCGGCCTGC TAGACCACTA GGAGACCCAG CCACGGTTAC

401  ACTATCTGGC CTATGGCTGG AACACGGAGC AGGATGCCAA GCGGGTTCGC
      TGATAGACCG GATACCGACC TTGTGCCTCG TCCTACGGTT CGCCCAAGCG

451  GATGCCATCA GCGATGCGGC CAACCGCATG GTACTGAACG GTGCCAAGCA
      CTACGGTAGT CGCTACGCCG GTTGGCGTAC CATGACTTGC CACGGTTCGT

501  GATACTGCTG TTCAACCTGC CGGATCTGGG CCAGAACCCG TCAGCTCGCA
      CTATGACGAC AAGTTGGACG GCCTAGACCC GGTCTTGGGC AGTCGAGCGT

551  GTCAGAAGGT GGTCGAGGCG GTCAGCCATG TCTCCGCCTA TCACAACCAG
      CAGTCTTCCA CCAGCTCCGC CAGTCGGTAC AGAGGCGGAT AGTGTTGGTC

601  CTGCTGCTGA ACCTGGCACG CCAGCTGGCC CCCACCGGCA TGGTAAAGCT
      GACGACGACT TGGACCGTGC GGTCGACCGG GGGTGGCCGT ACCATTTCGA

651  GTTCGAGATC GACAAGCAAT TTGCCGAGAT GCTGCGTGAT CCGCAGAACT
      CAAGCTCTAG CTGTTCGTTA AACGGCTCTA CGACGCACTA GGCGTCTTGA

701  TCGGCCTGAG CGACGTCGAG AACCCCTGCT ACGACGGCGG CTATGTGTGG
      AGCCGGACTC GCTGCAGCTC TTGGGGACGA TGCTGCCGCC GATACACACC

751  AAGCCGTTTG CCACCCGCAG CGTCAGCACC GACCGCCAGC TCTCCGCCTT
      TTCGGCAAAC GGTGGGCGTC GCAGTCGTGG CTGGCGGTCG AGAGGCGGAA

801  CAGTCCGCAG GAACGCCTCG CCATCGCCGG CAACCCGCTG CTGGCACAGG
      GTCAGGCGTC CTTGCGGAGC GGTAGCGGCC GTTGGGCGAC GACCGTGTCC

851  CCGTTGCCAG TCCTATGGCC CGCCGCAGCG CCAGCCCCCT CAACTGTGAG
      GGCAACGGTC AGGATACCGG GCGGCGTCGC GGTCGGGGGA GTTGACACTC

901  GGCAAGATGT TCTGGGATCA GGTACACCCG ACCACTGTCG TGCACGCAGC
      CCGTTCTACA AGACCCTAGT CCATGTGGGC TGGTGACAGC ACGTGCGTCG

951  CCTGAGCGAG CGCGCCGCCA CCTTCATCGC GAACCAGTAC GAGTTCCTCG
      GGACTCGCTC GCGCGGCGGT GGAAGTAGCG CTTGGTCATG CTCAAGGAGC

1001  CCCAC TGA
      GGGTG ACT
```

FIGURE 26 (SEQ ID No. 14)

```
   1 ATGAAAAAAT GGTTTGTTTG TTTATTGGGG TTGATCGCGC TGACAGTTCA
     TACTTTTTTA CCAAACAAAC AAATAACCCC AACTAGCGCG ACTGTCAAGT

51 GGCAGCCGAC ACTCGCCCCG CCTTCTCCCG GATCGTGATG TTCGGCGACA
     CCGTCGGCTG TGAGCGGGGC GGAAGAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAGCAGT TCCCGGGTCT GACCATCGCC AACGAAGCGG
     CCTCGTCGAC TGGTTCGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC ATATGGCTGG AATACGGAGC AGGATGCCAA GCGAGTTCGC
     TGATAGACCG TATACCGACC TTATGCCTCG TCCTACGGTT CGCTCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCCCGCA
     CTATGACGAC AAGTTGGACG GCCTAGACCC GGTCTTGGGC AGTCGGGCGT

551 GTCAGAAGGT GGTCGAGGCG GTCAGCCATG TCTCCGCCTA TCACAACAAG
     CAGTCTTCCA CCAGCTCCGC CAGTCGGTAC AGAGGCGGAT AGTGTTGTTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGA GACCCAGTAC GAGTTCCTCG
     GGACTCGCTC GCGCGGCGGT GGAAGTAGCT CTGGGTCATG CTCAAGGAGC

1001 CCCACGGATG A
     GGGTGCCTAC T
```

FIGURE 27 (SEQ ID No. 15)

```
   1 ATGTTTAAGT TTAAAAAGAA TTTCTTAGTT GGATTATCGG CAGCTTTAAT
     TACAAATTCA AATTTTTCTT AAAGAATCAA CCTAATAGCC GTCGAAATTA

51 GAGTATTAGC TTGTTTTCGG CAACCGCCTC TGCAGCTAGC GCCGACAGCC
     CTCATAATCG AACAAAAGCC GTTGGCGGAG ACGTCGATCG CGGCTGTCGG

101 GTCCCGCCTT TTCCCGGATC GTGATGTTCG GCGACAGCCT CTCCGATACC
     CAGGGCGGAA AAGGGCCTAG CACTACAAGC CGCTGTCGGA GAGGCTATGG

151 GGCAAAATGT ACAGCAAGAT GCGCGGTTAC CTCCCCTCCA GCCCGCCCTA
     CCGTTTTACA TGTCGTTCTA CGCGCCAATG GAGGGGAGGT CGGGCGGGAT

201 CTATGAGGGC CGTTTCTCCA ACGGACCCGT CTGGCTGGAG CAGCTGACCA
     GATACTCCCG GCAAAGAGGT TGCCTGGGCA GACCGACCTC GTCGACTGGT

251 AACAGTTCCC GGGTCTGACC ATCGCCAACG AAGCGGAAGG CGGTGCCACT
     TTGTCAAGGG CCCAGACTGG TAGCGGTTGC TTCGCCTTCC GCCACGGTGA

301 GCCGTGGCTT ACAACAAGAT CTCCTGGAAT CCCAAGTATC AGGTCATCAA
     CGGCACCGAA TGTTGTTCTA GAGGACCTTA GGGTTCATAG TCCAGTAGTT

351 CAACCTGGAC TACGAGGTCA CCCAGTTCTT GCAGAAAGAC AGCTTCAAGC
     GTTGGACCTG ATGCTCCAGT GGGTCAAGAA CGTCTTTCTG TCGAAGTTCG

401 CGGACGATCT GGTGATCCTC TGGGTCGGTG CCAATGACTA TCTGGCCTAT
     GCCTGCTAGA CCACTAGGAG ACCCAGCCAC GGTTACTGAT AGACCGGATA

451 GGCTGGAACA CGGAGCAGGA TGCCAAGCGG GTTCGCGATG CCATCAGCGA
     CCGACCTTGT GCCTCGTCCT ACGGTTCGCC CAAGCGCTAC GGTAGTCGCT

501 TGCGGCCAAC CGCATGGTAC TGAACGGTGC CAAGCAGATA CTGCTGTTCA
     ACGCCGGTTG GCGTACCATG ACTTGCCACG GTTCGTCTAT GACGACAAGT

551 ACCTGCCGGA TCTGGGCCAG AACCCGTCAG CTCGCAGTCA GAAGGTGGTC
     TGGACGGCCT AGACCCGGTC TTGGGCAGTC GAGCGTCAGT CTTCCACCAG

601 GAGGCGGTCA GCCATGTCTC CGCCTATCAC AACCAGCTGC TGCTGAACCT
     CTCCGCCAGT CGGTACAGAG GCGGATAGTG TTGGTCGACG ACGACTTGGA

651 GGCACGCCAG CTGGCCCCCA CCGGCATGGT AAAGCTGTTC GAGATCGACA
     CCGTGCGGTC GACCGGGGGT GGCCGTACCA TTTCGACAAG CTCTAGCTGT

701 AGCAATTTGC CGAGATGCTG CGTGATCCGC AGAACTTCGG CCTGAGCGAC
     TCGTTAAACG GCTCTACGAC GCACTAGGCG TCTTGAAGCC GGACTCGCTG

751 GTCGAGAACC CCTGCTACGA CGGCGGCTAT GTGTGGAAGC CGTTTGCCAC
     CAGCTCTTGG GGACGATGCT GCCGCCGATA CACACCTTCG GCAAACGGTG

801 CCGCAGCGTC AGCACCGACC GCCAGCTCTC CGCCTTCAGT CCGCAGGAAC
     GGCGTCGCAG TCGTGGCTGG CGGTCGAGAG GCGGAAGTCA GGCGTCCTTG

851 GCCTCGCCAT CGCCGGCAAC CCGCTGCTGG CACAGGCCGT TGCCAGTCCT
     CGGAGCGGTA GCGGCCGTTG GGCGACGACC GTGTCCGGCA ACGGTCAGGA

901 ATGGCCCGCC GCAGCGCCAG CCCCCTCAAC TGTGAGGGCA AGATGTTCTG
     TACCGGGCGG CGTCGCGGTC GGGGGAGTTG ACACTCCCGT TCTACAAGAC

951 GGATCAGGTA CACCCGACCA CTGTCGTGCA CGCAGCCCTG AGCGAGCGCG
     CCTAGTCCAT GTGGGCTGGT GACAGCACGT GCGTCGGGAC TCGCTCGCGC

1001 CCGCCACCTT CATCGCGAAC CAGTACGAGT TCCTCGCCCA CTGATGA
     GGCGGTGGAA GTAGCGCTTG GTCATGCTCA AGGAGCGGGT GACTACT
```

FIGURE 28

SEQ ID No. 16

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPF

236  RSASPLNCEG KMFWDQVHPT TVVHAALSER AATFIETQYE FLAHG
```

FIGURE 42

SEQ ID No. 25

```
  1 GACACTCGCC CCGCCTTCTC CCGGATCGTG ATGTTCGGCG ACAGCCTCTC CGATACCGGC
    CTGTGAGCGG GGCGGAAGAG GGCCTAGCAC TACAAGCCGC TGTCGGAGAG GCTATGGCCG

61 AAAATGTACA GCAAGATGCG CGGTTACCTC CCCTCCAGCC CGCCCTACTA TGAGGGCCGT
    TTTTACATGT CGTTCTACGC GCCAATGGAG GGGAGGTCGG GCGGGATGAT ACTCCCGGCA

121 TTCTCCAACG GACCCGTCTG GCTGGAGCAG CTGACCAAGC AGTTCCCGGG TCTGACCATC
    AAGAGGTTGC CTGGGCAGAC CGACCTCGTC GACTGGTTCG TCAAGGGCCC AGACTGGTAG

181 GCCAACGAAG CGGAAGGCGG TGCCACTGCC GTGGCTTACA ACAAGATCTC CTGGGACCCC
    CGGTTGCTTC GCCTTCCGCC ACGGTGACGG CACCGAATGT TGTTCTAGAG GACCCTGGGG

241 AAGTATCAGG TCATCAACAA CCTGGACTAC GAGGTCACCC AGTTCTTGCA GAAAGACAGC
    TTCATAGTCC AGTAGTTGTT GGACCTGATG CTCCAGTGGG TCAAGAACGT CTTTCTGTCG

301 TTCAAGCCGG ACGATCTGGT GATCCTCTGG GTCGGTGCCA ATGACTATCT GGCATATGGC
    AAGTTCGGCC TGCTAGACCA CTAGGAGACC CAGCCACGGT TACTGATAGA CCGTATACCG

361 TGGAATACCG AGCAGGATGC CAAGCGAGTT CGCGATGCCA TCAGCGATGC GGCCAACCGC
    ACCTTATGCC TCGTCCTACG GTTCGCTCAA GCGCTACGGT AGTCGCTACG CCGGTTGGCG

421 ATGGTACTGA ACGGTGCCAA GCAGATACTG CTGTTCAACC TGCCGGATCT GGGCCAGAAC
    TACCATGACT TGCCACGGTT CGTCTATGAC GACAAGTTGG ACGGCCTAGA CCCGGTCTTG

481 CCGTCAGCCC GCAGTCAGAA GGTGGTCGAG GCGGTCAGCC ATGTCTCCGC CTATCACAAC
    GGCAGTCGGG CGTCAGTCTT CCACCAGCTC CGCCAGTCGG TACAGAGGCG GATAGTGTTG

541 AAGCTGCTGC TGAACCTGGC ACGCCAGCTG GCCCCCACCG GCATGGTAAA GCTGTTCGAG
    TTCGACGACG ACTTGGACCG TGCGGTCGAC CGGGGGTGGC CGTACCATTT CGACAAGCTC

601 ATCGACAAGC AATTTGCCGA GATGCTGCGT GATCCGCAGA ACTTCGGCCT GAGCGACGTC
    TAGCTGTTCG TTAAACGGCT CTACGACGCA CTAGGCGTCT TGAAGCCGGA CTCGCTGCAG

661 GAGAACCCCT GCTACGACGG CGGCTATGTG TGGAAGCCGT TGCCACCCG CAGCGTCAGC
    CTCTTGGGGA CGATGCTGCC GCCGATACAC ACCTTCGGCA AACGGTGGGC GTCGCAGTCG

721 ACCGACCGCC AGCTCTCCGC CTTCAGTCCG CAGGAACGCC TCGCCATCGC CGGCAACCCG
    TGGCTGGCGG TCGAGAGGCG GAAGTCAGGC GTCCTTGCGG AGCGGTAGCG GCCGTTGGGC

781 CTGCTGGCAC AGGCCGTTGC CAGTCCTATG GCCCGCCGCA GCGCCAGCCC CCTCAACTGT
    GACGACCGTG TCCGGCAACG GTCAGGATAC CGGGCGGCGT CGCGGTCGGG GGAGTTGACA

841 GAGGGCAAGA TGTTCTGGGA TCAGGTACAC CCGACCACTG TCGTGCACGC AGCCCTGAGC
    CTCCCGTTCT ACAAGACCCT AGTCCATGTG GGCTGGTGAC AGCACGTGCG TCGGGACTCG

901 GAGCGCGCCG CCACCTTCAT CGAGACCCAG TACGAGTTCC TCGCCCACGG ATGA
    CTCGCGCGGC GGTGGAAGTA GCTCTGGGTC ATGCTCAAGG AGCGGGTGCC TACT
```

LIPID ACYLTRANSFERASE PROTEINS AND METHODS OF MAKING THEM

INCORPORATION BY REFERENCE

This application is a continuation-in-part application of international patent application Serial No. PCT/IB2009/054535 filed 15 Oct. 2009, which published as PCT Publication No. WO 2011/045629 on 21 Apr. 2011. Reference is also made to the following related applications: US 2002-0009518, US 2004-0091574, WO2004/064537, WO2004/064987, WO2005/066347, WO2005/066351, U.S. Application Ser. No. 60/764,430 filed on 2 Feb. 2006, WO2006/008508, International Patent Application Number PCT/IB2007/000558 and U.S. application Ser. No. 11/671,953.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted in ASCII format via EFS-Web and is hereby incorporated by reference in its entirety. Said ASCII copy, created on Sep. 26, 2012, is named 43049002.txt and is 75,655 bytes in size.

FIELD OF THE INVENTION

The present invention relates to methods of engineering and producing variant enzymes. The present invention further relates to novel variant enzymes and to the use of these novel variant enzymes.

BACKGROUND OF THE INVENTION

Lipid:cholesterol acyltransferase enzymes have been known for some time (see for example Buckley—Biochemistry 1983, 22, 5490-5493). In particular, glycerophospholipid:cholesterol acyl transferases (GCATs) have been found, which like the plant and/or mammalian lecithin:cholesterol acyltransferases (LCATs), will catalyse fatty acid transfer between phosphatidylcholine and cholesterol.

Upton and Buckley (TIBS 20, May 1995, p 178-179) and Brumlik and Buckley (J. of Bacteriology April 1996, p 2060-2064) teach a lipase/acyltransferase from *Aeromonas hydrophila* which has the ability to carry out acyl transfer to alcohol receptors in aqueous media.

A putative substrate binding domain and active site of the *A. hydrophila* acyltransferase have been identified (see for example Thornton et al 1988 Biochem. et Biophys. Acta. 959, 153-159 and Hilton & Buckley 1991 J. Biol. Chem. 266, 997-1000) for this enzyme.

Buckley et al (J. Bacteriol 1996, 178(7) 2060-4) taught that Ser16, Asp116 and His291 are essential amino acids which must be retained for enzyme activity to be maintained.

Robertson et al (J. Biol. Chem. 1994, 269, 2146-50) taught some specific mutations, namely Y226F, Y230F, Y30F, F13S, S18G, and S18V of the *A. hydrophila* acyltransferase, none of which is encompassed by the present invention.

WO 2005/066347 relates to variant lipid acyltransferases and methods of making same. These variant enzymes are not encompassed by the present invention.

The development of variant lipid acyltransferases with modified (enhanced) activity has not been without difficulties, particularly in finding variant lipid acyltransferases which have high specific activity in a number of applications.

Citation or identification of any document in this application is not an admission that such document is available as prior art to the present invention.

SUMMARY OF THE PRESENT INVENTION

The present invention is predicated upon the finding by the inventors of particular sites of interest for modification. The present inventors for the first time have modelled the lipid acyltransferase enzyme and using the tertiary structure of the enzyme identified specific regions for modification. In addition the present inventors have prepared and tested enzymes modified in accordance with their findings above and identified advantageous variant lipid acyltransferases for use in a number of applications.

Aspects of the present invention are presented in the claims and in the following commentary.

In one aspect of the present invention there is provided a method for preparing a variant lipid acyltransferase enzyme comprising expressing in a host organism a nucleotide sequence which has at least 90% identity with a nucleotide sequence encoding a parent lipid acyltransferase and comprises at least one modification (suitably at least two modifications) at a position(s) which corresponds in the encoded amino acid sequence to an amino acid(s) located in a) the canyon region of the enzyme and/or b) insertion site 1 and/or c) insertion site 2, wherein the canyon region, insertion site 1 and/or insertion site 2 enzyme is defined as that region which when aligned based on primary or tertiary structure corresponds to the canyon region, insertion site 1 or insertion site 2 of the enzyme shown herein as SEQ ID No. 6 or SEQ ID No. 16.

In one embodiment preferably the modification(s) at a position located in the canyon and/or insertion site 1 and/or insertion site 2 is combined with at least one modification at a position which corresponds in the encoded amino acid sequence to an amino acid located outside of the canyon region and/or insertion site 1 and/or insertion site 2.

In another aspect of the present invention there is provided a method for preparing a variant lipid acyltransferase enzyme comprising expressing in a host organism a nucleotide sequence which has at least 90% identity with a nucleotide sequence encoding a parent lipid acyltransferase and comprises at least one modification (suitably at least two modifications) at a position(s) which corresponds in the encoded amino acid sequence to an amino acid(s) located at position 27, 31, 85, 86, 122, 119, 120, 201, 245, 232, 235 and/or 236 (preferably at position 27, 31, 85, 86, 119 and/or 120, more preferably at position 27 and/or 31), wherein the position numbering is defined as that position which when aligned based on primary or tertiary structure corresponds to the same position of the enzyme shown herein as SEQ ID No. 6.

In a further aspect of the present invention there is provided a method for preparing a variant lipid acyltransferase enzyme comprising expressing in a host organism a nucleotide sequence which has at least 90% identity with a nucleotide sequence encoding a parent lipid acyltransferase and comprises at least one modification at a position(s) which corresponds in the encoded amino acid sequence to an amino acid(s) located at position 27 and/or 31 in combination with at least one further modification, wherein the position numbering is defined as that position which when aligned based on primary or tertiary structure corresponds to the same position of the enzyme shown herein as SEQ ID No. 6.

Suitably, the at least one further modification may be at one or more of the following positions 85, 86, 122, 119, 120, 201, 245, 23, 81, 82, 289, 227, 229, 233, 33, 207, 130, wherein the position numbering is defined as that position which when aligned based on primary or tertiary structure corresponds to the same position of the enzyme shown herein as SEQ ID No. 6.

In a further aspect the present invention provides a method of producing a variant lipid acyltransferase, said method comprising modifying a lipid acyltransferase amino acid sequence backbone such that at least one modification (suitably at least two modifications) is made at a position(s) which corresponds in the encoded amino acid sequence to an amino acid(s) located in a) the canyon region of the enzyme and/or b) insertion site 1 and/or c) insertion site 2, wherein the canyon region, insertion site 1 and/or insertion site 2 enzyme is defined as that region which when aligned based on primary or tertiary structure corresponds to the canyon region, insertion site 1 or insertion site 2, respectively, of the enzyme shown herein as SEQ ID No. 6 or SEQ ID No. 16.

In one embodiment preferably the modification(s) at a position located in the canyon and/or insertion site 1 and/or insertion site 2 is combined with at least one modification at a position which corresponds in the encoded amino acid sequence to an amino acid located outside of the canyon region and/or insertion site 1 and/or insertion site 2.

In another aspect of the present invention provides a method of producing a variant lipid acyltransferase, said method comprising modifying a lipid acyltransferase amino acid sequence backbone such that at least one modification (suitably at least two modifications) is made at a position(s) which corresponds in the encoded amino acid sequence to an amino acid(s) located in position 27, 31, 85, 86, 122, 119, 120, 201, 245, 232, 235 and/or 236 (preferably at position 27, 31, 85, 86 119 and/or 120, more preferably at position 27 and/or 31), wherein the position numbering is defined as that position which when aligned based on primary or tertiary structure corresponds to the same position of the enzyme shown herein as SEQ ID No. 6.

In a further aspect of the present invention there is provided a method of producing a variant lipid acyltransferase, said method comprising modifying a lipid acyltransferase amino acid sequence backbone such that at least one modification (suitably at least two modifications) is made at a position(s) which corresponds in the encoded amino acid sequence to an amino acid(s) located in position 27, 31 in combination with at least one further modification, wherein the position numbering is defined as that position which when aligned based on primary or tertiary structure corresponds to the same position of the enzyme shown herein as SEQ ID No. 6.

Suitably, the at least one further modification may be at one or more of the following positions 85, 86, 122, 119, 120, 201, 245, 23, 81, 82, 289, 227, 229, 233, 33, 207, 130, wherein the position numbering is defined as that position which when aligned based on primary or tertiary structure corresponds to the same position of the enzyme shown herein as SEQ ID No. 6.

A method comprising: altering the length of a substrate chain length specificity determining segment that lies immediately N-terminal to the catalytic triad (preferably the Asp residue of the catalytic triad) of a parent enzyme (e.g. a parent lipid acyltransferase) that has an amino acid sequence that is at least 70% identical to the lipid acyltransferase from *A. salmonicida* shown herein as SEQ ID No. 6 or 16, to produce an altered lipid acyltransferase enzyme that has an altered substrate specificity relative to said parent enzyme.

Preferably the altering comprises making an amino acid insertion or deletion in said substrate chain length specificity determining segment, such as substituting said substrate chain length specificity determining segment of said parent enzyme with the substrate chain length specificity determining segment of a different lipid acyltransferase to produce said altered lipid acyltransferase. Preferably, said altering increases the length of acyl chain that can be transferred by said lipid acyltransferase. In one embodiment preferably the method comprises testing said altered lipid acyltransferase enzyme for an altered substrate specificity.

Suitably, said testing may include evaluating the ability of said altered or variant lipid acyltransferase enzyme to transfer an acyl group from a substrate to a recipient molecule in an aqueous environment. In one embodiment said testing includes evaluating the ability of said variant lipid acyltransferase and said parent enzyme to transfer acyl chains of different lengths.

The present invention yet further provides an altered or variant lipid acyltransferase comprising an amino acid sequence that is at least 70% identical to the lipid acyltransferase from *Aeromonas salmonicida* shown herein as SEQ ID No. 6 or 16, wherein a substrate chain length specificity determining segment that lies immediately N-terminal of the Asp residue of the catalytic triad of said altered lipid acyltransferase has an altered length relative to said lipid acyltransferase from *Aeromonas salmonicida* shown herein as SEQ ID No. 6 or 16.

Preferably, the altered lipid acyltransferase comprises an amino acid sequence that is at least 90% identical to the lipid acyltransferase from *Aeromonas salmonicida* shown herein as SEQ ID No. 6 or 16.

In a further aspect the present invention provides a (variant) lipid acyltransferase polypeptide obtained by the method(s) according to the present invention.

In a yet further aspect there is provided a nucleic acid (preferably an isolated or recombinant nucleic acid) or a vector comprising a nucleotide sequence encoding a lipid acyltransferase enzyme and which nucleotide sequence comprises at least one modification at a position which corresponds in the encoded amino acid sequence to one or more of the following positions: 27, 31, 85, 86, 122, 119, 120, 201, 245, 232, 235 and/or 236 (preferably at position 27, 31, 85, 86 119 and/or 120, more preferably at position 27 and/or 31), wherein the position numbering is defined as that position which when aligned based on primary or tertiary structure corresponds to the same position of the enzyme shown herein as SEQ ID No. 6.

In a further aspect of the present invention there is provided a nucleic acid (preferably an isolated or recombinant nucleic acid) or a vector comprising a nucleotide sequence encoding a lipid acyltransferase enzyme and which nucleotide sequence comprises at least one modification at a position which corresponds in the encoded amino acid sequence to one or more of the following positions: 27 and/or 31, in combination with at least one further modification, wherein the position numbering is defined as that position which when aligned based on primary or tertiary structure corresponds to the same position of the enzyme shown herein as SEQ ID No. 6.

Suitably, the at least one further modification may be at one or more of the following positions 85, 86, 122, 119, 120, 201, 245, 23, 81, 82, 289, 227, 229, 233, 33, 207, 130, wherein the position numbering is defined as that position which when aligned based on primary or tertiary structure corresponds to the same position of the enzyme shown herein as SEQ ID No. 6.

Preferably the nucleotide sequence encoding the lipid acyltransferase enzyme in accordance with the present invention and before modification is a nucleotide sequence shown herein as SEQ ID No. 25, SEQ ID No. 10, SEQ ID No. 11, SEQ ID No. 12, SEQ ID No. 13, SEQ ID No. 14 or SEQ ID No. 15; or is a nucleotide sequence which has at least 70% identity (preferably at least 80%, more preferably at least 90%, even more preferably at least 95% identity) with a nucleotide sequence shown herein as SEQ ID No. 25, SEQ ID No. 10, SEQ ID No. 11, SEQ ID No. 12, SEQ ID No. 13, SEQ ID No. 14 or SEQ ID No. 15; or is a nucleotide sequence which is related to SEQ ID No. 25, SEQ ID No. 10, SEQ ID No. 11, SEQ ID No. 12, SEQ ID No. 13, SEQ ID No. 14, SEQ ID No. 15 by the degeneration of the genetic code; or is a nucleotide sequence which hybridizes under medium stringency or high stringency conditions to a nucleotide sequence shown herein as SEQ ID No. 25, SEQ ID No. 10, SEQ ID No. 11, SEQ ID No. 12, SEQ ID No. 13, SEQ ID No. 14 or SEQ ID No. 15.

The present invention provides in one aspect an isolated or recombinant nucleic acid encoding a polypeptide having lipid acyltransferase activity and comprising a sequence having at least 94% (preferably at least 98%) amino acid sequence identity to the mature region of SEQ ID No. 6 or 16 and which comprises at least one modification (preferably at least two modifications) at a position located at position 27, 31, 85, 86, 122, 119, 120, 201, 245, 232, 235 and/or 236 (preferably at position 27, 31, 85, 86, 119 and/or 120, more preferably at position 27 and/or 31) wherein the position numbering is defined as that position which when aligned based on primary or tertiary structure corresponds to the same position in the enzyme shown herein as SEQ ID No. 6.

The present invention provides in one aspect an isolated or recombinant nucleic acid encoding a polypeptide having lipid acyltransferase activity and comprising a sequence having at least 94% (preferably at least 98%) amino acid sequence identity to the mature region of SEQ ID No. 6 or 16 and which comprises at least one modification (suitably at least two modifications) at a position(s) which corresponds in the encoded amino acid sequence to an amino acid(s) located in position 27 and/or 31 in combination with at least one further modification, wherein the position numbering is defined as that position which when aligned based on primary or tertiary structure corresponds to the same position of the enzyme shown herein as SEQ ID No. 6.

Suitably, the at least one further modification may be at one or more of the following positions 85, 86, 122, 119, 120, 201, 245, 23, 81, 82, 289, 227, 229, 233, 33, 207, 130, wherein the position numbering is defined as that position which when aligned based on primary or tertiary structure corresponds to the same position of the enzyme shown herein as SEQ ID No. 6.

In one aspect there is provided a nucleic acid (preferably an isolated or recombinant nucleic acid) or a vector comprising a nucleotide sequence encoding a polypeptide having lipid acyltransferase activity, wherein the nucleotide sequence hybridizes under medium or high stringency conditions over substantially the entire length of SEQ ID No. 10 or SEQ ID No. 25 or a compliment of SEQ ID No. 10 or SEQ ID No. 25, wherein the encoded polypeptide comprising one or more amino acid residues selected from Q, H, N, T, F, Y or C at position 31; R, Y, S, V, I, A, T, M, F, C or L at position 86; R, G, H, K, Y, D, N, V, C, Q, L, E, S or F at position 27; H, R, D, E 85; T or I at position 119; K or E at position 120; S, L, A, F, W, Y, R, H, M or C at position 122; R at position 201; S as position 245; A or V at position 235; G or S at position 232; G or E at position 236, wherein the positions are equivalent amino acid positions with respect of SEQ ID No. 6.

In a further aspect the present invention provides a variant lipid acyltransferase polypeptide encoded by the nucleic acid or nucleotide sequence according to the present invention.

In one aspect the present invention provides a variant lipid acyltransferase polypeptide encoded by a nucleic acid or nucleotide sequence according to the present invention when expressed in a *Bacillus* expression host, in particular in a *B. licheniformis* expression host.

In another aspect the present invention provides a method of producing a polypeptide comprising introducing the nucleic acid or a vector into a host cell (preferably a *Bacillus* expression host, in particular in a *B. licheniformis* expression host), wherein said nucleic acid or vector comprising said nucleotide sequence encoding said polypeptide operably linked to a regulatory sequence capable of directing expression of a polypeptide encoded by the nucleic acid, culturing the host cell under conditions in which the regulatory sequence directs expression of the polypeptide encoded by the nucleic acid or vector.

In one aspect the present invention provides a pro-peptide or a polypeptide which has lipid acyltransferase activity and comprises an amino acid sequence which is at least 90% (preferably at least 95%, more preferably at least 98%, more preferably at least 99%) identical with the amino acid sequence shown as SEQ ID No. 6 or 16 and comprises one or more modifications at one or more of the following positions: 27, 31, 85, 86, 122, 119, 120, 201, 245, 232, 235 and/or 236 (preferably at position 27, 31, 85, 86, 119 and/or 120 more preferably at position 27 and/or 31).

In another aspect the present invention provides a pro-peptide or a polypeptide which has lipid acyltransferase activity and comprises an amino acid sequence shown as SEQ ID No. 6 or 16 except for one or more modifications at one or more of the following positions: 27, 31, 85, 86, 122, 119, 120, 201, 245, 232, 235 and/or 236 (preferably at position 27, 31, 85, 86, 119 and/or 120 more preferably at position 27 and/or 31).

In one aspect the present invention provides a pro-peptide or a polypeptide which has lipid acyltransferase activity and comprises an amino acid sequence which is at least 90% (preferably at least 95%, more preferably at least 98%, more preferably at least 99%) identical with the amino acid sequence shown as SEQ ID No. 6 or 16 and comprises one or more modifications at positions 27 and/or 31 in combination with at least one further modification, wherein the position numbering is defined as that position which when aligned based on primary or tertiary structure corresponds to the same position of the enzyme shown herein as SEQ ID No 6.

Suitably, the at least one further modification may be at one or more of the following positions 85, 86, 122, 119, 120, 201, 245, 23, 81, 82, 289, 227, 229, 233, 33, 207, 130, wherein the position numbering is defined as that position which when aligned based on primary or tertiary structure corresponds to the same position of the enzyme shown herein as SEQ ID No. 6.

In another aspect the present invention provides a pro-peptide or a polypeptide which has lipid acyltransferase activity and comprises an amino acid sequence shown as SEQ ID No. 6 or 16 except for one or more modifications at one or more of the following positions: 27 and/or 31 in combination with at least one further modification.

Suitably, the at least one further modification may be at one or more of the following positions 85, 86, 122, 119, 120, 201, 245, 23, 81, 82, 289, 227, 229, 233, 33, 207 and/or 130, wherein the position numbering is defined as that position which when aligned based on primary or tertiary structure corresponds to the same position of the enzyme shown herein as SEQ ID No. 6.

The polypeptide of the present invention may be a propeptide which undergoes further post-translational modification to a mature peptide, i.e. a polypeptide which has lipid acyltransferase activity. By way of example only SEQ ID No. 16 is the same as SEQ ID No. 6 except that SEQ ID No. 16 has undergone post-translational and/or post-transcriptional modification to remove some amino acids, more specifically 38 amino acids. Therefore the polypeptide shown herein as SEQ ID No. 6 could be considered in some circumstances (i.e. in some host cells) as a pro-peptide—which is further processed to a mature peptide by post-translational and/or post-transcriptional modification. The precise modifications, e.g. cleavage site(s), in respect of the post-translational and/or post-transcriptional modification may vary slightly depending on host species. In some host species there may be no post translational and/or post-transcriptional modification, hence the pro-peptide would then be equivalent to the mature peptide (i.e. a polypeptide which has lipid acyltransferase activity). Without wishing to be bound by theory, the cleavage site(s) may be shifted by a few residues (e.g. 1, 2 or 3 residues) in either direction compared with the cleavage site shown by reference to SEQ ID No. 16 compared with SEQ ID No. 6. In other words, rather than cleavage at position 235-ATR to position 273 (RRSAS) (SEQ ID NO: 47) for example, the cleavage may commence at residue 232, 233, 234, 235, 236, 237 or 238 for example. In addition or alternatively, the cleavage may end at residue 270, 271, 272, 273, 274, 275 or 276 for example. In addition or alternatively, the cleavage may result in the removal of about 38 amino acids, in some embodiments the cleavage may result in the removal of between 30-45 residues, such as 34-42 residues, such as 36-40 residues, preferably 38 residues.

The present invention further provides a method of making a foodstuff comprising adding a polypeptide according to the present invention to one or more ingredients of the foodstuff.

In another aspect the present invention provides a method of making a baked product comprising adding a polypeptide according to the present invention to a dough and baking the dough to make the baked product.

In another aspect, the present invention provides the use of a variant lipid acyltransferase enzyme of the present invention or obtainable (preferably, obtained) by the method according to the present invention in a process of treating egg or egg-based products to produce lysophospholipids.

The present invention further provides a method of preparing a lyso-phospholipid comprising treating a phospholipid with a polypeptide according to the present invention to produce the lyso-phospholipid.

In a yet further embodiment the present invention provides a method of preparing a lyso-glycolipid comprising treating a glycolipid with a polypeptide according to the present invention to produce a lyso-glycolipid.

The present invention further provides a process of enzymatic degumming of vegetable or edible oils, comprising treating the edible or vegetable oil with a polypeptide according to the present invention so as to hydrolyze a major part of the polar lipids present therein.

In another aspect of the present invention, there is provided the use of a variant lipid acyltransferase enzyme according to the present invention or obtainable (preferably, obtained) by the method according to the present invention in a process for reducing the content of a phospholipid in an edible oil, comprising treating the oil with said variant lipolytic enzyme so as to hydrolyze a major part of the phospholipid, and separating an aqueous phase containing the hydrolyzed phospholipid from the oil.

In another aspect the present invention provides a foodstuff or a baked product obtained by the method of the present invention.

In another aspect the present invention provides a cleaning composition or a detergent composition comprising a variant lipid acyltransferase according to the present invention.

In a further aspect there is provided a bread and/or dough improving composition comprising a variant lipid acyltransferase according to the present invention.

Other aspects concerning the nucleotide sequences which can be used in the present invention include: a construct comprising the sequences of the present invention; a vector comprising the sequences for use in the present invention; a plasmid comprising the sequences for use in the present invention; a transformed cell comprising the sequences for use in the present invention; a transformed tissue comprising the sequences for use in the present invention; a transformed organ comprising the sequences for use in the present invention; a transformed host comprising the sequences for use in the present invention; a transformed organism comprising the sequences for use in the present invention. The present invention also encompasses methods of expressing the nucleotide sequence for use in the present invention using the same, such as expression in a host cell; including methods for transferring same. The present invention further encompasses methods of isolating the nucleotide sequence, such as isolating from a host cell.

Other aspects concerning the amino acid sequence for use in the present invention include: a construct encoding the amino acid sequences for use in the present invention; a vector encoding the amino acid sequences for use in the present invention; a plasmid encoding the amino acid sequences for use in the present invention; a transformed cell expressing the amino acid sequences for use in the present invention; a transformed tissue expressing the amino acid sequences for use in the present invention; a transformed organ expressing the amino acid sequences for use in the present invention; a transformed host expressing the amino acid sequences for use in the present invention; a transformed organism expressing the amino acid sequences for use in the present invention. The present invention also encompasses methods of purifying the amino acid sequence for use in the present invention using the same, such as expression in a host cell; including methods of transferring same, and then purifying said sequence.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 shows the amino acid sequence of a mutant *Aeromonas salmonicida* mature lipid acyltransferase (GCAT) with a mutation of Asn80Asp (notably, amino acid 80 is in the mature sequence) (SEQ ID No. 6);

FIG. 2 shows an amino acid sequence (SEQ ID No. 1) a lipid acyl transferase from *Aeromonas hydrophila* (ATCC #7965);

FIG. 3 shows a pfam00657 consensus sequence from database version 6 (SEQ ID No. 2);

FIG. 4 shows an amino acid sequence (SEQ ID No. 3) obtained from the organism *Aeromonas hydrophila* (P10480; GI:121051);

FIG. 5 shows an amino acid sequence (SEQ ID No. 4) obtained from the organism *Aeromonas salmonicida* (AAG098404; GI:9964017);

FIG. 6 shows an amino acid sequence (SEQ ID No. 5) of a lipid acyltransferase from *Aeromonas salmonicida* subsp. *Salmonicida* (ATCC#14174);

FIG. 7 shows an amino acid sequence (SEQ ID No. 7) of the fusion construct used for mutagenesis of the *Aeromonas hydrophila* lipid acyltransferase gene. The underlined amino acids is a xylanase signal peptide;

FIG. 8 shows an amino acid sequence (SEQ ID No. 8) obtained from the organism *Aeromonas hydrophila* (P10480; GI:121051);

FIG. 9 shows the amino acid sequence (SEQ ID No. 9) of a mutant *Aeromonas salmonicida* mature lipid acyltransferase (GCAT);

Figure 13:
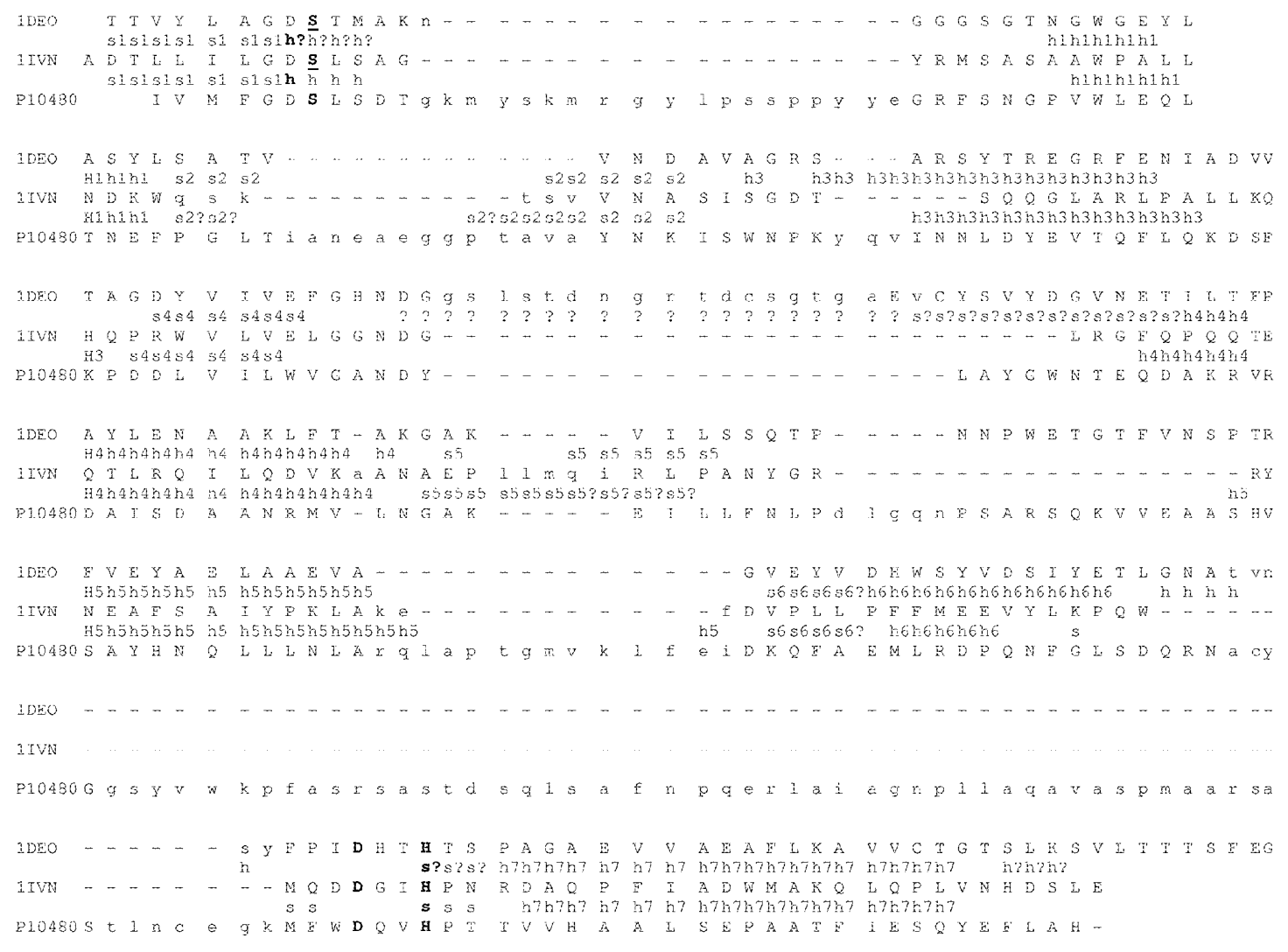

FIG. 13 shows alignment 1 (SEQ ID NOS 26-28, respectively, in order of appearance);

Figure 14:
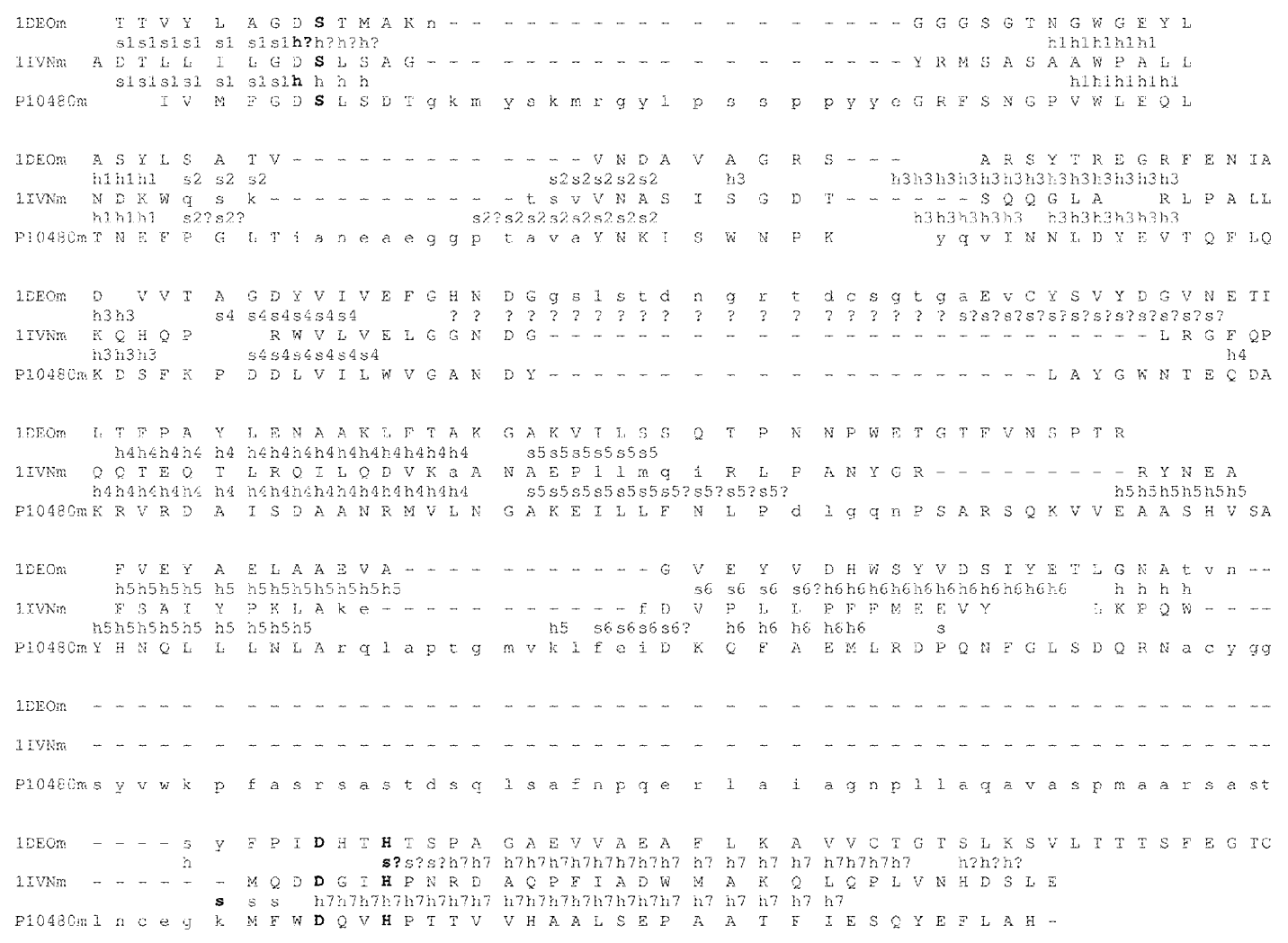

FIG. 14 shows alignment 2 (SEQ ID NOS 29 and 27-28, respectively, in order of appearance);

Figure 15A:
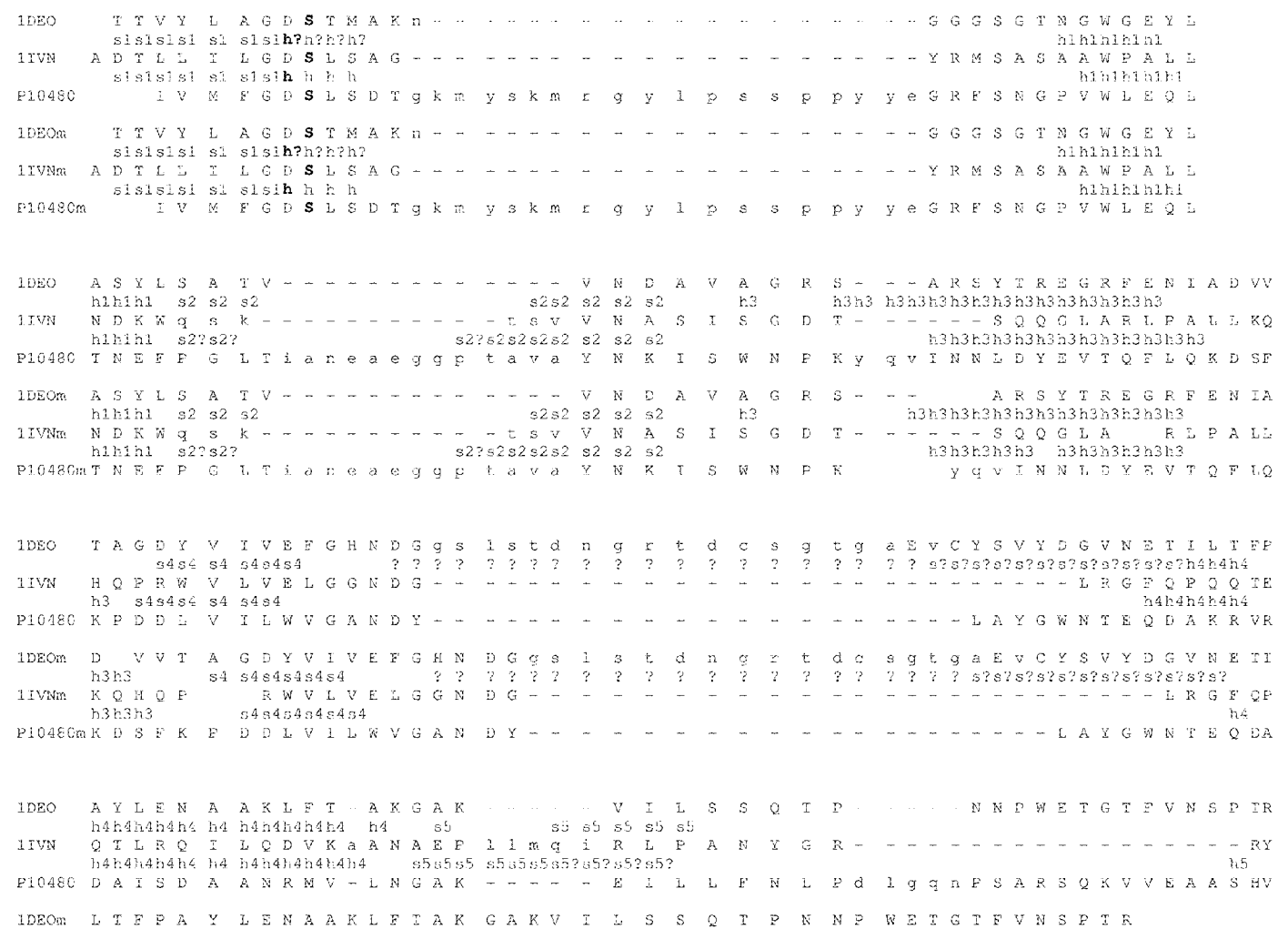
Figure 15B:
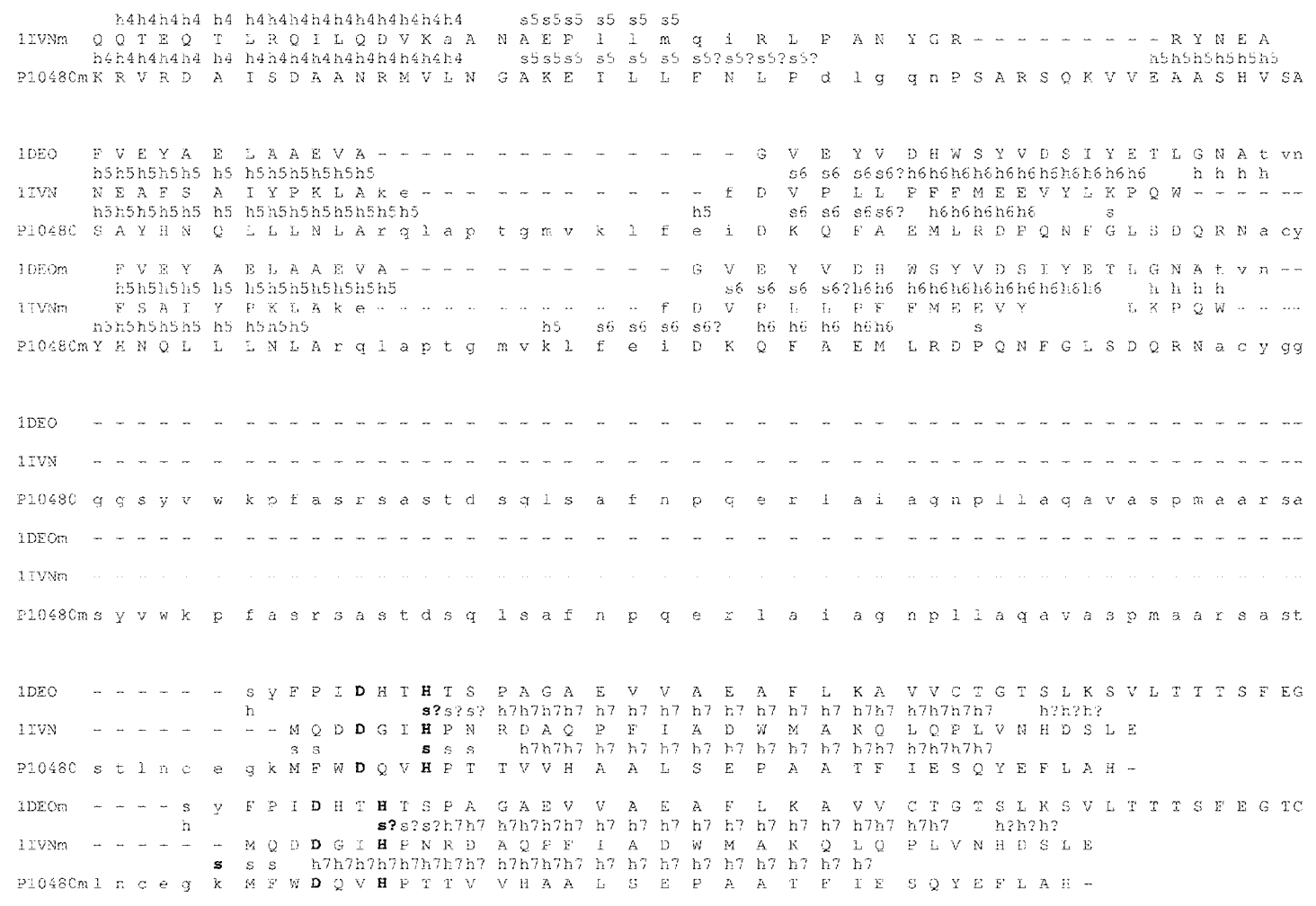

FIGS. 15 and 16 show an alignment of 1IVN to P10480 (P10480 is the database sequence for *A. hydrophila* enzyme), this alignment was obtained from the PFAM database and used in the model building process; FIGS. 15A and 15B disclose SEQ ID NOS 26-29 and 27-28, respectively, in order of appearance and FIG. 16 discloses SEQ ID NOS 30-31, respectively, in order of appearance;

FIG. 17 shows an alignment where P10480 is the database sequence for *Aeromonas hydrophila*. This sequence is used for the model construction and the site selection. Note that the full protein (SEQ ID No. 3) is depicted, the mature protein (equivalent to SEQ ID No. 50) starts at residue 19. *A. sal* is *Aeromonas salmonicida* (SEQ ID No. 9) GDSX (SEQ ID NO: 48) lipase, *A. hyd* is *Aeromonas hydrophila* (SEQ ID No. 50) GDSX (SEQ ID NO: 48) lipase. The consensus sequence (SEQ ID NO: 53) contains a * at the position of a difference between the listed sequences;

FIG. 18 shows a gene construct;

FIG. 20 shows the sequence of the XhoI insert containing the a lipid acyltransferase precursor gene, the −35 and −10 boxes are underlined; FIG. 20 discloses the DNA sequence as SEQ ID NO: 45 and the coded protein as SEQ ID NO: 46;

FIG. 22 shows a nucleotide sequence from *Aeromonas salmonicida* (SEQ ID No. 10) including the signal sequence (preLAT—positions 1 to 87);

FIG. 23 shows a nucleotide sequence (SEQ ID No. 11) encoding a lipid acyl transferase according to the present invention obtained from the organism *Aeromonas hydrophila*;

FIG. 24 shows a nucleotide sequence (SEQ ID No. 12) encoding a lipid acyl transferase according to the present invention obtained from the organism *Aeromonas salmonicida*;

FIG. 25 shows a nucleotide sequence (SEQ ID No. 13) encoding a lipid acyltransferase from *Aeromonas hydrophila* (ATCC #7965);

FIG. 26 shows a nucleotide sequence (SEQ ID No. 14) encoding a lipid acyltransferase from *Aeromonas salmonicida* subsp. *Salmonicida* (ATCC#14174);

FIG. 27 shows a nucleotide sequence (SEQ ID No. 15) encoding an enzyme from *Aeromonas hydrophila* including a xylanase signal peptide;

FIG. 28 shows the amino acid sequence of a mutant *Aeromonas salmonicida* mature lipid acyltransferase (GCAT) with a mutation of Asn80Asp (notably, amino acid 80 is in the mature sequence)—shown herein as SEQ ID No. 6—and after undergoing post-translational modification as SEQ ID No. 16—amino acid residues 235 and 236 of SEQ ID No. 16 are not covalently linked following post-translational modification. The two peptides formed are held together by one or more S—S bridges. Amino acid 236 in SEQ ID No. 16 corresponds with the amino acid residue number 274 in SEQ ID No. 6 shown herein [SEQ ID No. 16 is the same as SEQ ID No. 6 except SEQ ID No. 15 shows the sequence after post-translational clipping or cleavage to remove 38 amino acids];

FIG. 42 shows SEQ ID No. 25 a nucleotide sequence encoding a backbone lipid acyltransferase enzyme from *Aeromonas salmonicida* which was used in the preparation of the variant lipid acyltransferase enzyme in the examples hereinbelow;

DETAILED DESCRIPTION

Figure 10:
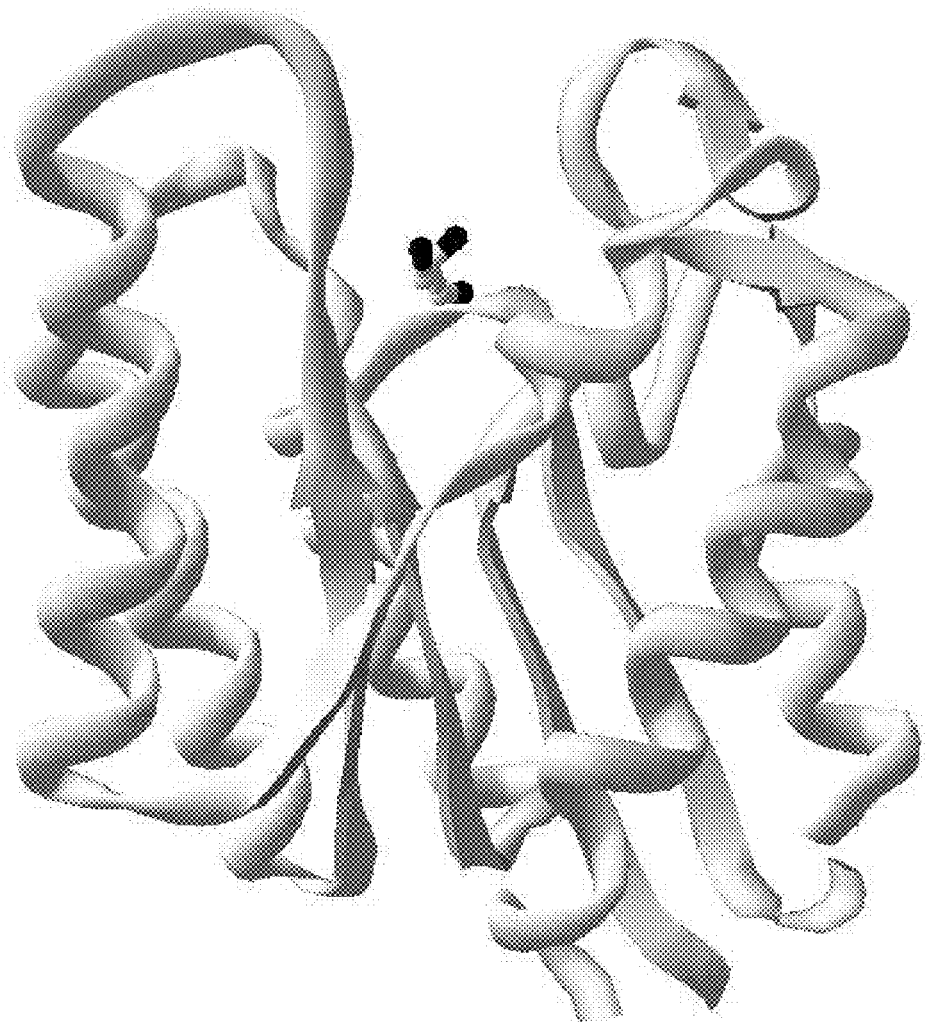
FIG. 10 shows a ribbon representation of the 1IVN.PDB crystal structure which has glycerol in the active site. The Figure was made using the Deep View Swiss-PDB viewer.
Figure 11:
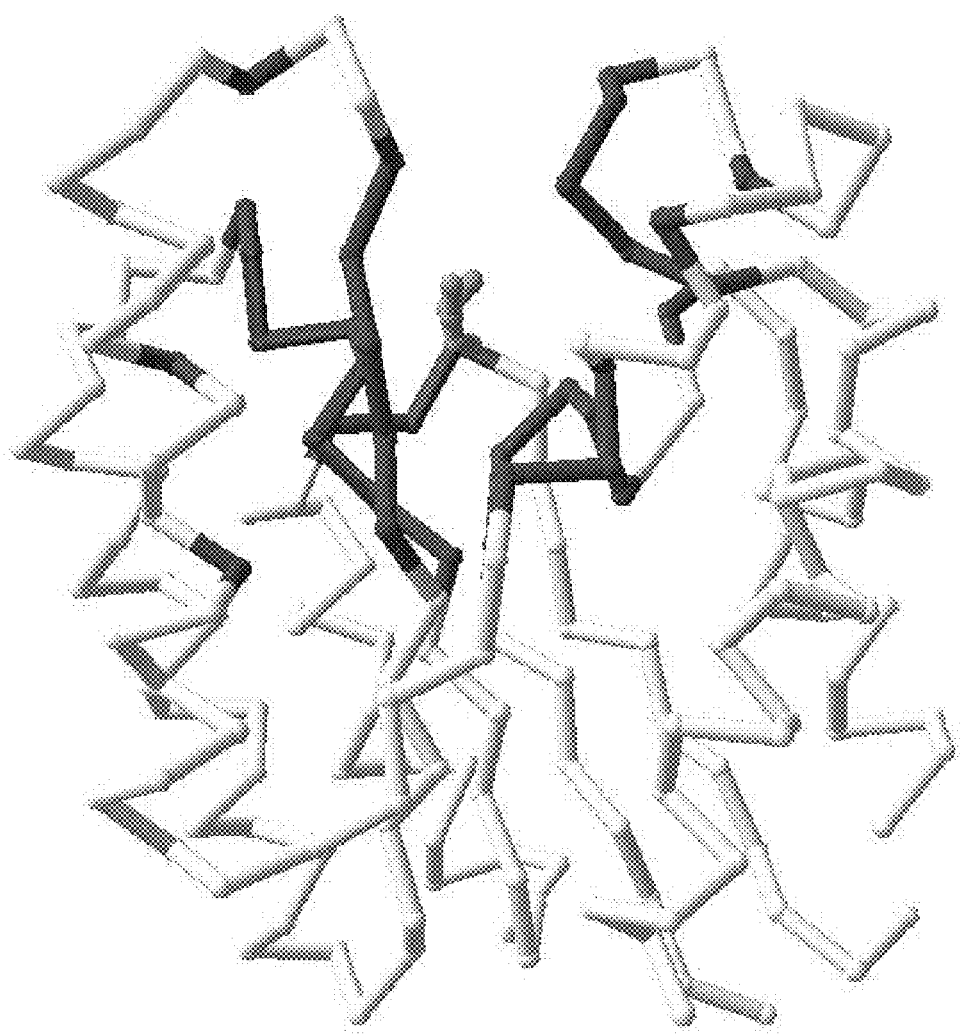
FIG. 11 shows 1IVN.PDB Crystal Structure—Side View using Deep View Swiss-PDB viewer, with glycerol in active site—residues within 101 of active site glycerol are coloured black.
Figure 12:
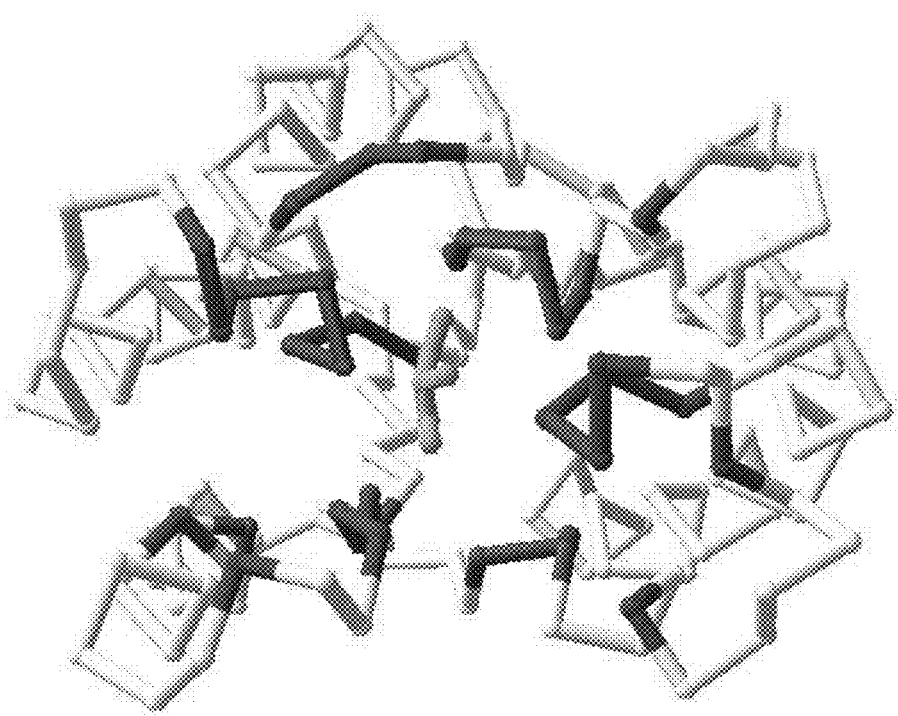
FIG. 12 shows 1IVN.PDB Crystal Structure—Top View using Deep View Swiss-PDB viewer, with glycerol in active site—residues within 101 of active site glycerol are coloured black.
Figure 19:
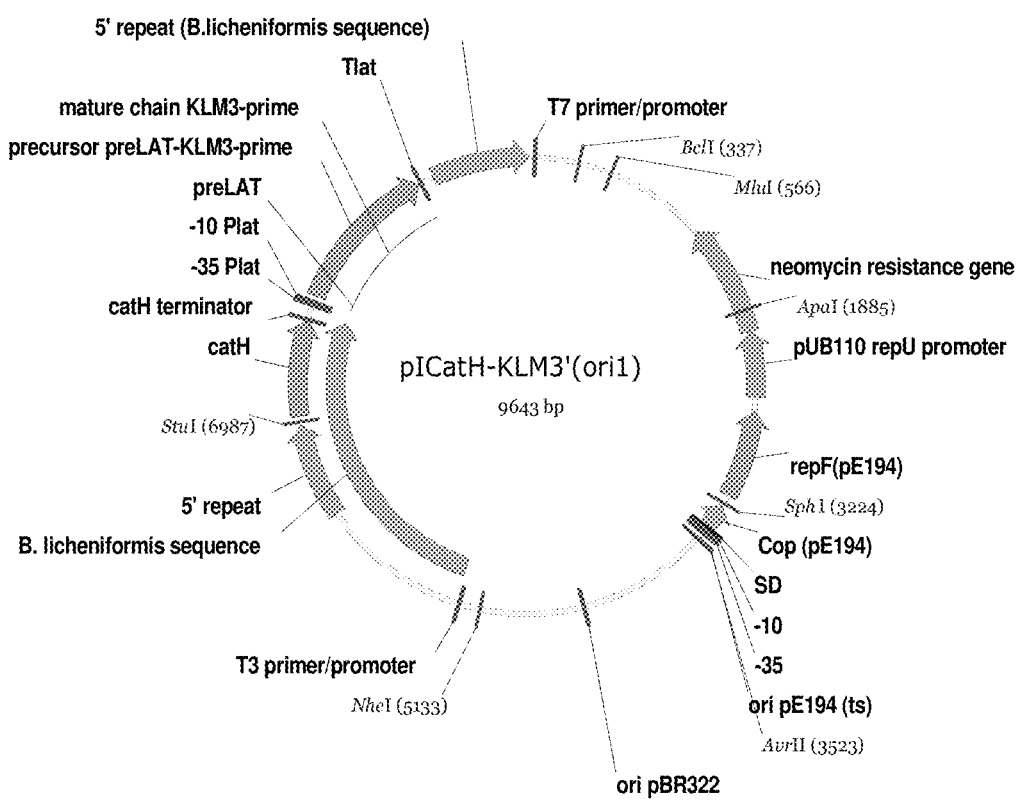
FIG. 19 shows a codon optimised gene construct (no. 052907)
Figure 21:
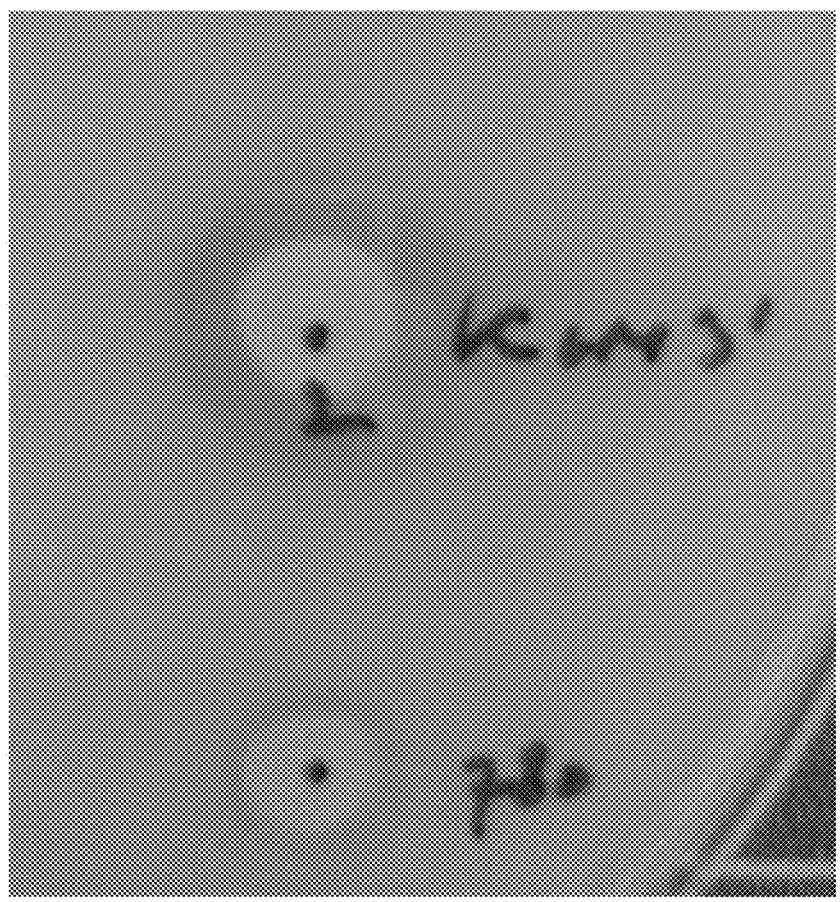
FIG. 21 shows BML780-KLM3'CAP50 (comprising SEQ ID No. 16—upper colony) and BML780 (the empty host strain—lower colony) after 48 h growth at 37° C. on 1% tributyrin agar.

All amino acid position numbering as used herein unless stated otherwise relates to the corresponding position when aligned based on primary and/or tertiary structure (preferably primary structure) to the enzyme shown herein as SEQ ID No. 6. In some embodiments however the amino acid position numbering as used herein may relate to the corresponding position when aligned based on tertiary structure to the enzyme shown herein as SEQ ID No. 16.

When analysing the 3-D (tertiary structure) of lipid acyltransferases it became possible to determine suitable modification sites in the enzyme to produce engineered lipid acyltransferase enzymes with improved properties.

In the present invention there is provided a means to identify regions suitable for modification in a lipid acyltransferase. In some preferred embodiments the modification(s) result in improved properties which may be include a) altering the substrate specificity of the lipid acyltransferase, for instance and by way of example only: i) altering the enzymes ability to use certain compounds as acceptors, for example improving the enzymes ability to utilise a carbohydrate (e.g. maltose) as an acceptor molecule thus improving the enzymes ability to produce a carbohydrate ester): or ii) altering the enzymes ability to use saturated or unsaturated fatty acids as a substrate: or iii) changing the enzymes specificity such that it preferentially utilises the fatty acid from the Sn1 or Sn2 position of the lipid: or iv) altering the substrate chain length specificity of the enzyme; b) altering the kinetics of the enzyme; and/or c) lowering the enzymes ability to carry out a hydrolysis reaction whilst maintaining or enhancing the enzymes ability to carry out an acyl transferase reaction.

The tertiary structure of the lipid acyltransferases has revealed an unusual and interesting structure which allows lipid acyltransferases to be engineered more successfully. In particular the lipid acyltransferase tertiary structure has revealed a cave and canyon structure.

Alterations in the cave region may (for example) alter the enzyme's substrate chain length specificity for example.

Alterations in the canyon (particularly some preferred key modifications) have been found to be important in for example enhancing or changing the enzyme's substrate specificity.

In particular it has been found by the present inventors that there are a number of modifications in the canyon which rank highly and produce interesting variants with improved properties—these can be found at positions 31, 27, 85, 86, 119 and 120. In some embodiments positions 31 and/or 27 are highly preferred.

In a broad concept of the present invention it is therefore envisaged to modify lipid acyltransferase enzymes in the cave and/or canyon region (preferably the canyon region) thereof to provide modified enzymes having altered activity/properties.

In some embodiments it is preferred to have at least one modification in the canyon region in combination with at least one modification either elsewhere in the canyon or outside of the canyon. In some embodiments preferably the alternations are not within the cave region.

In one broad aspect the present invention may provide a method of modifying a lipid acyltransferase (either by modifying the nucleotide sequence or the amino acid sequence) thus to result in one or modifications in the following residues: 27, 31, 85, 86, 122, 119, 120, 201, 245, 232, 235, 236, and nucleic acids and lipid acyltransferases having said modification(s).

In another broad aspect the present invention may provide a method for modifying a lipid acyltransferase (either by modifying the nucleotide sequence or the amino acid sequence) thus to result in one or modifications in the following residues: 27, 31, 85, 86, 122, 119, 120, 201, 245, this/these can be in some instances be in combination with one or more further modifications in one or more of the following residues 23, 81, 82, 289, 227, 229, 233, 33, 207 or 130. The present invention also provides nucleic acids and lipid acyltransferases having these modification(s).

The variant enzyme must comprise at least one amino acid modification compared with the parent enzyme. In some embodiments, the variant enzyme may comprise at least 2, preferably at least 3, preferably at least 4 amino acid modifications compared with the parent enzyme.

In some embodiments of the present invention, the DNA sequence encoding the lipid acyltransferase shown herein as SEQ ID No. 6 or 16 is modified.

Suitably the methods according to the present invention may comprise a further step of formulating the variant enzyme into an enzyme composition and/or a foodstuff composition, such as a bread improving composition. The present invention further provides for a bread improving composition comprising said variant lipid acyltransferase according to the present invention.

Preferably the method of producing a variant lipid acyltransferase enzyme further comprises one or more of the following steps:

1) structural homology mapping or
2) sequence homology alignment.

An amino acid residue of a lipid acyltransferase may be equivalent to a residue of the lipid acyltransferase shown herein as SEQ ID No. 16 or 6 if it is either homologous (i.e. having a corresponding position in either the primary and/or tertiary structure) or analogous to a specific residue or portion of that residue in the lipid acyltransferase shown in SEQ ID no. 6 or 16 (i.e. having the same or similar functional capacity to combine, react, and/or chemically interact).

In some embodiments, in order to establish homology to primary structure, the amino acid sequence of a lipid acyltransferase is directly compared to the lipid acyltransferase enzyme shown herein as SEQ ID No. 6 or 16 primary sequence and particularly to a set of residues known to be invariant in all or most lipid acyltransferases for which sequences are known. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of SEQ ID No. 6 or 16 are defined. In preferred embodiments, alignment of conserved residues conserves 100% of such residues. However, alignment of greater than 75% or as little as 50% of conserved residues are also adequate to define equivalent residues. In preferred embodiments, conservation of the catalytic serine and histidine residues are maintained. Conserved residues are used to define the corresponding equivalent amino acid residues of the lipid acyltransferase shown in SEQ ID No. 6 or 16 in other lipid acyltransferases, such as from other *Aeromonas* species, as well as any other organisms.

In order to align a parent lipid acyltransferase with SEQ ID No. 6 or SEQ ID No. 16 (the reference sequence), sequence alignment such as pairwise alignment can be used (eg. Pairwise Sequence Alignment website of the European Bioinformatics Institute). Thereby, the equivalent amino acids in alternative parental lipid acyltransferase polypeptides, which correspond to one or more of the amino acids defined with reference to SEQ ID No. 16 or SEQ ID No. 6 can be determined and modified. As the skilled person will readily appreciate, when using the emboss pairwise alignment, standard settings usually suffice. Corresponding residues can be identified using "needle" in order to make an alignment that covers the whole length of both sequences. However, it is also possible to find the best region of similarity between two sequences, using "water".

Alternatively, particularly in instances where parent lipid acyltransferase shares low primary sequence homology with SEQ ID No. 6 or SEQ ID No. 16, the corresponding amino acids in alternative parent lipid acyltransferase which correspond to one or more of the amino acids defined with reference to SEQ ID No. 6 or SEQ ID No. 16 can be determined by structural alignment to the structural model of SEQ ID No. 16 or SEQ ID No. 6, preferably SEQ ID No. 16.

Thus, equivalent residues may be defined by determining homology at the level of tertiary structure for a lipid acyltransferase whose tertiary structure has been determined by x-ray crystallography. In this context, "equivalent residues" are defined as those for which the atomic coordinates of two or more of the main chain atoms of a particular amino acid residue of the lipid acyltransferase shown herein as SEQ ID No. 6 or 16 (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the lipid acyltransferase in question to the lipid acyltransferase shown herein as SEQ ID No. 6 or 16. As known in the art, the best model is the crystallographic model giving the lowest R factor for experimental diffraction data at the highest resolution available. Equivalent residues which are functionally and/or structurally analogous to a specific residue of the lipid acyltransferase as shown herein as SEQ ID No. 6 or 16 are defined as those amino acids of the lipid acyltransferase that preferentially adopt a conformation such that they either alter, modify or modulate the protein structure, to effect changes in substrate specification, e.g. substrate binding and/or catalysis in a manner defined and attributed to a specific residue of the lipid acyltransferase shown herein as SEQ ID No. 6 or 16. Further, they are those residues of the lipid acyltransferase (in cases where a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of the lipid acyltransferase shown herein as SEQ ID No. 6 or 16.

The coordinates of the three dimensional structure of the lipid acyltransferase shown herein as SEQ ID No. 16 (which is a *Aeromonas salmonicida* lipid acyltransferase comprising an N80D mutation) were determined and are set forth in the Table below and find use in determining equivalent residues on the level of tertiary structure.

Crystallization

Crystals of the enzyme were obtained using hanging drop diffusion whereby a drop (5 μl protein solution (mg/ml in) was mixed with 5 μl of a reservoir solution 1.4 M ammonium phosphate, 0.10 M potassium phosphate, 44 mM sodium chloride, 94 mM ammonium chloride, 2 mM magnesium sulphate, 2 mM calcium chloride) was placed on a plastic coverslip and inverted over a well of a 6×4 Linbro plate containing 1 ml of a reservoir solution and allowed to reach equilibrium for a period lasting several days to 2 weeks. Crystals of the (NH4)2PtCl4 were obtained by soaking pre-grown crystals in the reservoir solution above containing 10 mM (NH4)2PtCl4.

X-Ray Data Collection.

Multiwavelength anomalous diffraction data were collected for the $(NH_4)_2PtCl4$ derivative at the Stanford Synchrotron Radiation Laboratory (SSRL, Menlo Park, USA) on beamline 11.1 at wavelengths corresponding to the inflection ($\lambda 1$), low energy remote ($\lambda 2$), and the peak ($\lambda 3$) of a platinum MAD experiment. Later, a data set ($\lambda 0$) was collected to 1.5 Å resolution. The data sets were collected at 100K using Quantum 315 CCD. Data were integrated using Mosflm (Leslie, A. G. W. (1999) Acta Crystallogr., D55, 1696-1702) and scaled with the SCALA program from the CCP4 suite (Collaborate computer project, Number 4 (1994) The CCP4 suite: programs for protein crystallography. Acta Chrystallogr., D50, 760-763). Data statistics are summarized in Table A.

X-Ray Data Collection.

Multiwavelength anomalous diffraction data were collected for the $(NH_4)_2PtCl_4$ derivative at the Stanford Synchrotron Radiation Laboratory (SSRL, Menlo Park, USA) on beamline 11.1 at wavelengths corresponding to the peak ($\lambda 1$) of a platinum SAD experiment. Later, a data set ($\lambda 0$) was collected to 1.5 Å resolution. The data sets were collected at 100K using Quantum 315 CCD. Data were integrated using Mosflm [supra] and scaled with the SCALA program from the CCP4 suite [supra]. Data statistics are summarized in the Table below (mod).

Structure Solution and Refinement.

The initial structure was determined using the 2.8 Å platinum SAD data ($\lambda_3$ or $\lambda_1$) using the CCP4 suite and SOLVE/RESOLVE programs (Terwilliger, T. C. and Berendzen, J. (1999) Acta Crystallogr., D55, 849-861). Model building was performed using $O^{10}$ and COOT (Jones, T. A., et al. (1991) Acta Crystallogr., A47, 110-119). The traced model was then refined with the 1.5 Å dataset ($\lambda 0$) using REFMAC (Collaborate computer project, Number 4 (1994) The CCP4 suite: programs for protein crystallography. Acta Chrystallogr., D50, 760-763). Refinement statistics are summarized in the Table below. The final model includes a protein dimer and 1198 water molecules in the asymmetric unit. No electron density was observed for the first methionine residue in any of the molecules. PROCHECK11 (Laskowski, G. N. et al. (1993) J. Appl. Chrystallogr., 26, 91-07.) indicates that 94% of the residues in all of the monomers are located in the core regions of the Ramachandran plot (Ramachandran, G. N. et al. (1968) Advan. Protein Chem., 23, 283-437) with no residues in the disallowed or generously allowed regions.

All graphics figures were prepared with PyMOL (Warren L. DeLano "The PyMOL Molecular Graphics System." DeLano Scientific, Belmont, Calif., USA. http://www.pymol.org).

TABLE A

Summary of crystal parameters, data collection and refinement statistics for the lipid acyltransferase enzyme shown herein as SEQ ID No. 16 (also known herein as a lipid acyltransferase enzyme from *Aeromonas salmonicida* having N80D mutation and being post-translationally modified (clipped)):

| | | | | |
|---|---|---|---|---|
| Space group | P41212 | | | |
| Unit cell parameters | a = 118.770 Å, b = 118.770 Å, c = 102.406 Å, $\alpha = \beta = \gamma = 90°$ | | | |
| Data Collection | $\lambda_0$Ref | $\lambda_1$MADPt | $\lambda_2$MADPt | $\lambda_3$MADPt |
| Wavelength (Å) | 0.9794 | 1.0723 | 0.9840 | 1.0717 |
| Resolution range (Å) | 50.0-1.49 | 50.0-2.55 | 50.0-2.55 | 50.0-2.50 |
| Number of observations | 748,006 | 136,900 | 134,056 | 222,260 |
| Number of reflections | 118,096 | 41,605 | 41,649 | 47,456 |
| Completeness (%) | 99.0 (93.8)+ | 89.9 (47.2) | 90.2 (48.2)+ | 99.0 (83.3)+ |
| Mean I/σ(I) | 17.5 (4.2)+ | 8.5 (0.9)+ | 8.7 (1.0)+ | 10.1 (2.4)+ |
| $R_{sym}$ on I | 0.058 (0.381)+ | 0.087 (0.701)+ | 0.088 (0.863)+ | 0.089 (0.580)+ |
| Sigma Cutoff | 0.0 | 0.0 | 0.0 | 0.0 |
| Highest resolution shell (Å) | 1.54-1.49 | 2.64-2.55 | 2.64-2.55 | 2.59-2.50 |

Model and refinement

| | | | |
|---|---|---|---|
| Resolution range (Å) | 30.00-1.50 | Data set used in refinement | $\lambda_0$MADSe |
| No. of reflections (total) | 110,653 | Cutoff criteria | \|F\| > 0 |

TABLE A-continued

Summary of crystal parameters, data collection and refinement statistics for the lipid acyltransferase enzyme shown herein as SEQ ID No. 16 (also known herein as a lipid acyltransferase enzyme from *Aeromonas salmonicida* having N80D mutation and being post-translationally modified (clipped)):

| | | |
|---|---|---|
| No. of reflections (test) | 5510 | $R_{cryst}$ 0.202 |
| Completeness (% total) | 99.21 | $R_{free}$ 0.213 |
| Deviation from ideal geometry (rms): | | |
| Bond length | 0.009 Å | |
| Bond angle | 1.23° | |
| Average B-value protein | 13.3 | |
| Average B-value water | Å$^2$ | |
| ESU based on R value | Å | |
| Protein residues/atoms | | |
| Solvent molecules | | |

†highest resolution shell

ESU = Estimated overall coordinate error (Tickle et al., 1998).

$R_{sym} = \Sigma |I_i - <I_i>|/\Sigma |I_i|$ where $I_i$ is the scaled intensity of the $i^{th}$ measurement, and $<I_i>$ is the mean intensity for that reflection.

$R_{cryst} = \Sigma |\ |F_{obs}| - |F_{calc}|\ |/\Sigma |F_{obs}|$ where $F_{calc}$ and $F_{obs}$ are the calculated and observed structure factor amplitudes, respectively.

$R_{free}$ = as for $R_{cryst}$, but for 5.0% of the total reflections chosen at random and omitted from refinement.

The crystal structure shows that the enzyme is an catalytic triad is composed of Ser 16, Asp 288 and His 291.

A structural-homology search may be performed using the program DALI (Holm and Sander, Trends Biochem. Sci., 478-480 [1995]), which is based on a distance criterion and does not use sequence information for the comparison to obtain closely related proteins.

In the present invention an *E. coli* thioesterase I (1IVN) was aligned structurally with the lipid acyltransferase enzyme shown herein as SEQ ID No. 16 using the program PyMOL to identify regions which may be interesting for engineering in the lipid acyltransferase. Notably the thioesterase I (1IVN) is an enzyme which has a very different activity and specificity compared with lipid acyltransferases and it has a completely different amino acid sequence when viewed on a primary level. However, the tertiary structure of thioesterase I (1IVN) can be compared with lipid acyltransferases. The fact that these enzymes have very different activities despite the structural similarities are useful when engineering lipid acyltransferases and selecting modifications as the small differences in the tertiary structure (e.g. the cave, canyon regions and the insertion regions must be contributing to the different activity of the lipid acyltransferase enzyme compared with the thioesterase I (1IVN).

This alignment revealed some interesting points in that the lipid acyltransferase was found to share a common structural motif, having the five-stranded parallel β-sheet structure sandwiched by α-helices on either side. The three-dimensional structure of the *Aeromonas salmonicida* lipid acyltransferase which has undergone post-translational modification (i.e. clipping) and which comprises the N80D mutation (SEQ ID No. 16) showed that lipid acyltransferases, in particular the lipid acyltransferase enzyme, contains large insertions between common elements of secondary structure.

For instance, there is a large insertion in the acyltransferase of *Aeromonas salmonicida* between the last beta strand and the ASP-X-X_HIS motif. This insertion creates a large cavity (hereinafter referred to as the "cave" that binds the aliphatic chain of the acyl enzyme intermediate. Modulating the sequence and size of this region results in a smaller or larger "cave" or cavity for the aliphatic chain of the acyl enzyme intermediate, i.e., the acyl chain that is transferred by the enzyme. Thus the enzymes of this family may be engineered to preferentially transfer acyl chains of different lengths.

Four insertions are found in the lipid acyltransferase relative to the *E. coli* thioesterase (PDB entry 1IVN) that link common secondary structural elements common to both structures.

The amino acids coordinates of these insertions in the lipid acyltransferase shown here as SEQ ID No. 16 are listed in the Table below: The insertions are also shown in the structure of FIG. 32, FIG. 33, FIG. 34 and FIG. 35.

TABLE

| Insertions in lipid acyltransferase: | |
|---|---|
| Insertion | Residues |
| Insertion 1 | 22-36 |
| Insertion 2 | 74-88 |
| Insertion 3 | 162-168 |
| Insertion 4 | 213-281 |

Figure 30:
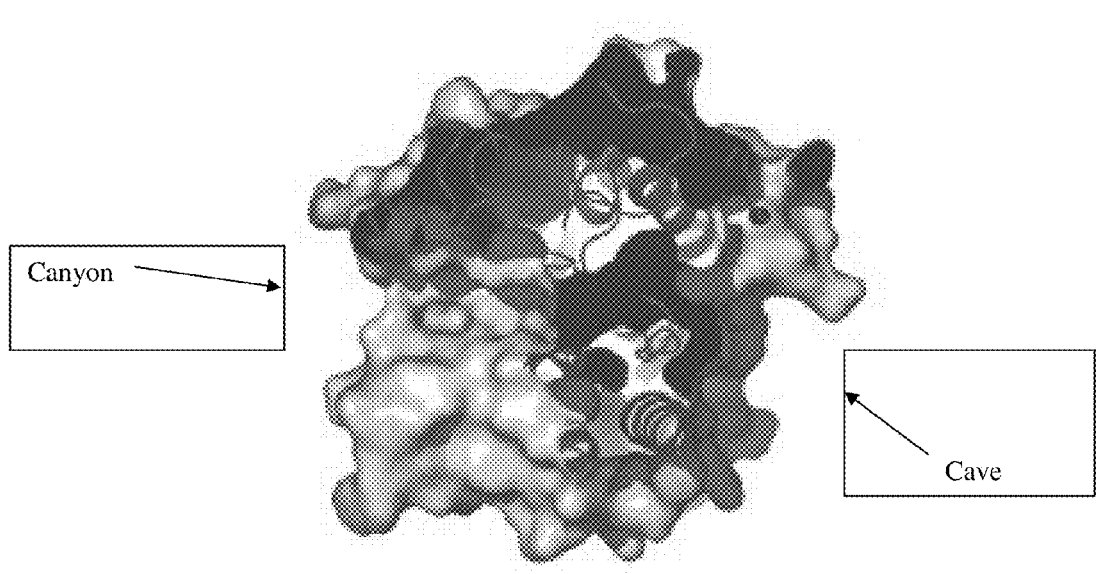
FIG. 30 shows the "canyon" and "cave" structure of lipid acyltransferases, in particular of the *Aeromonas salmonicida* lipid acyltransferase enzyme taught herein as SEQ ID No. 16.
Figure 31:
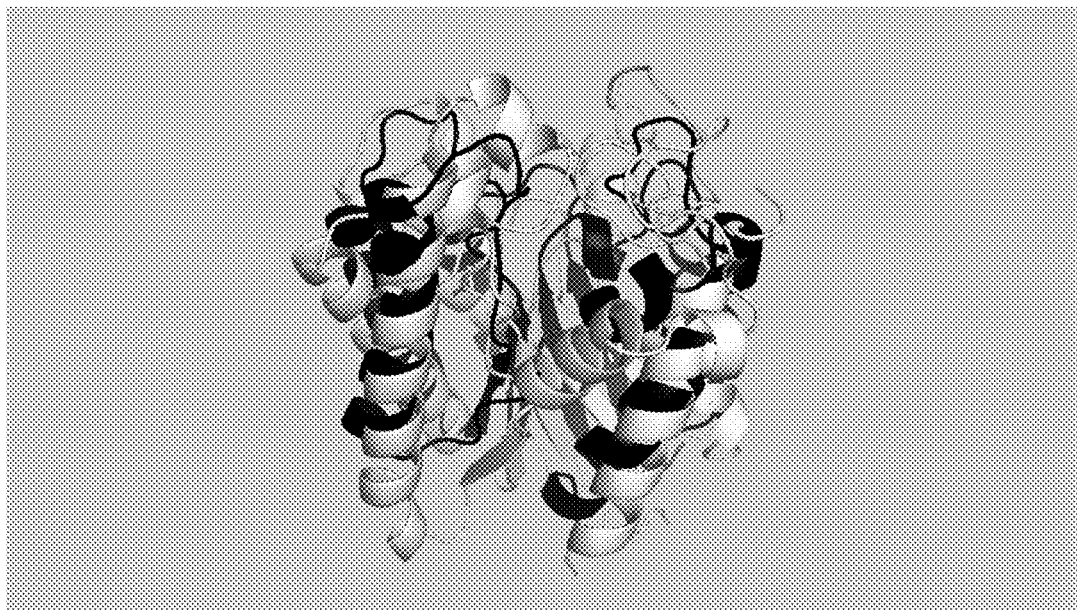
FIG. 31 shows the structural alignment between the lipid acyltransferase of *Aeromonas salmonicida* lipid acyltransferase comprising the N80D mutation and which is the mature sequence having undergone post-translational clipping [shown herein as SEQ ID No. 16] (white) and *E. coli* thioesterase (black) (PDB entry 1IVN)
Figure 32:
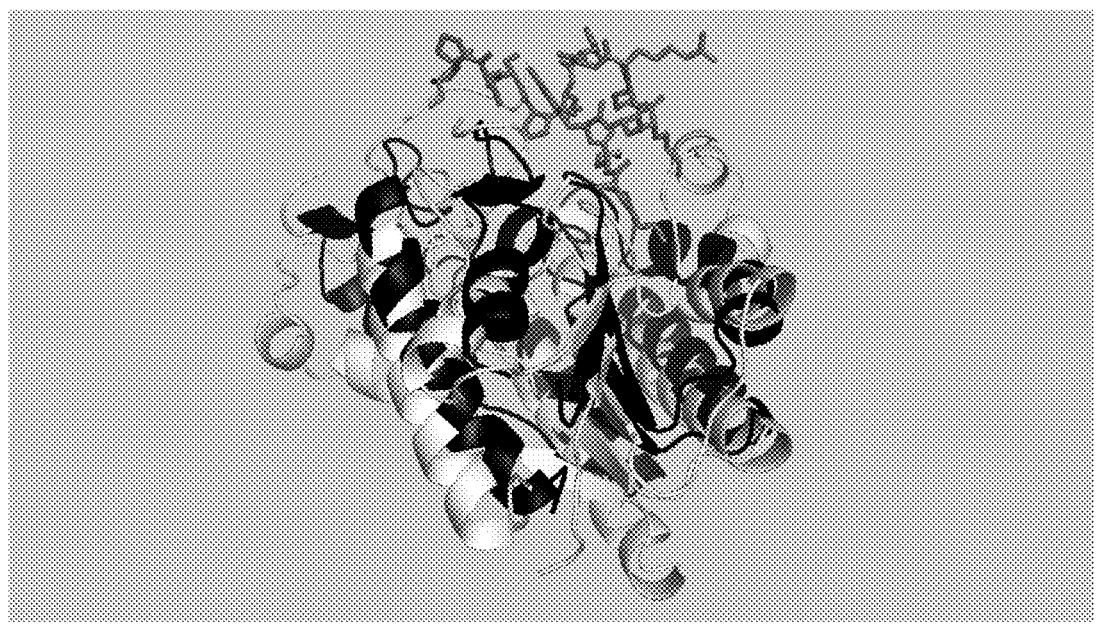
FIG. 32 shows the structural alignment between the lipid acyltransferase of *Aeromonas salmonicida* lipid acyltransferase comprising the N80D mutation and which is the mature sequence having undergone post-translational clipping [shown herein as SEQ ID No. 16] (white) and *E. coli* thioesterase (black) (PDB entry 1IVN) and identifies the residues of "insertion 1" (residues 22-36) as sticks.
Figure 33:
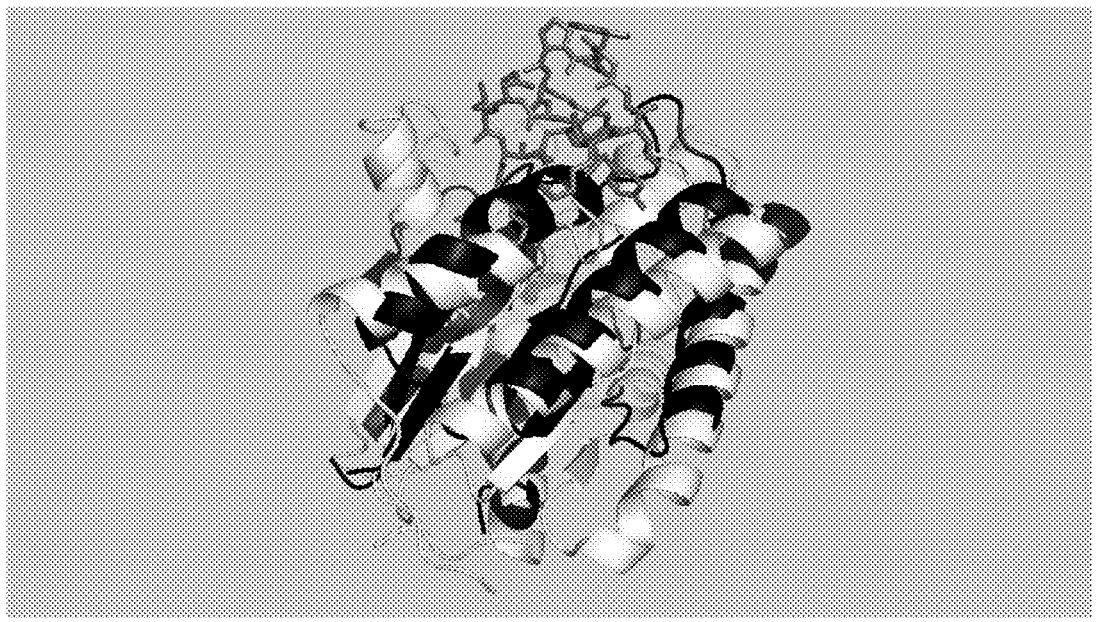
FIG. 33 shows the structural alignment between the lipid acyltransferase of *Aeromonas salmonicida* lipid acyltransferase comprising the N80D mutation and which is the mature sequence having undergone post-translational clipping [shown herein as SEQ ID No. 16] (white) and *E. coli* thioesterase (black) (PDB entry 1IVN) and identifies the residues of "insertion 2" (residues 74-88) as sticks.
Figure 34:
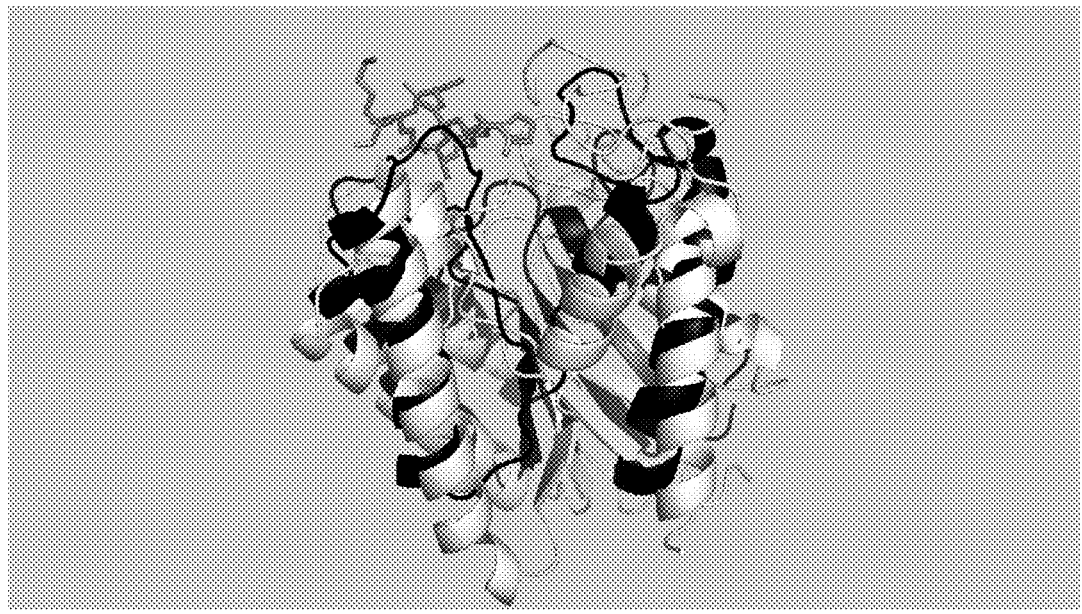
FIG. 34 shows the structural alignment between the lipid acyltransferase of *Aeromonas salmonicida* lipid acyltransferase comprising the N80D mutation and which is the mature sequence having undergone post-translational clipping [shown herein as SEQ ID No. 16] (white) and *E. coli* thioesterase (black) (PDB entry 1IVN) and identifies the residues of "insertion 3" (residues 162-168) as sticks.
Figure 35:
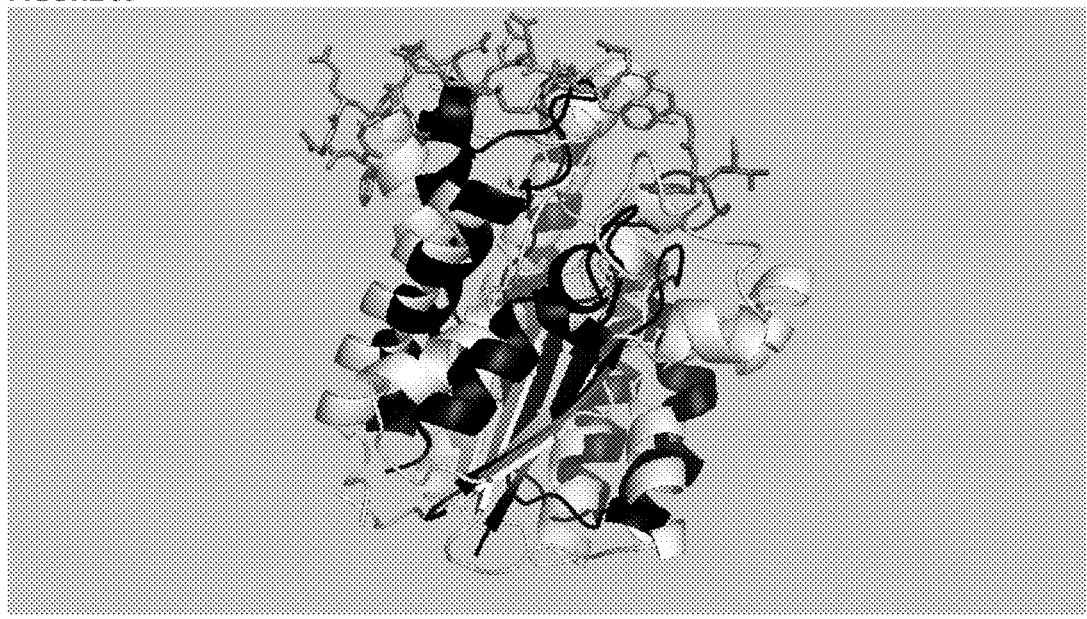
FIG. 35 shows the structural alignment between the lipid acyltransferase of *Aeromonas salmonicida* lipid acyltransferase comprising the N80D mutation and which is the mature sequence having undergone post-translational clipping [shown herein as SEQ ID No. 16] (white) and *E. coli* thioesterase (black) (PDB entry 1IVN) and identifies the residues of "insertion 4" (residues 213-281) as sticks.
Figure 36:
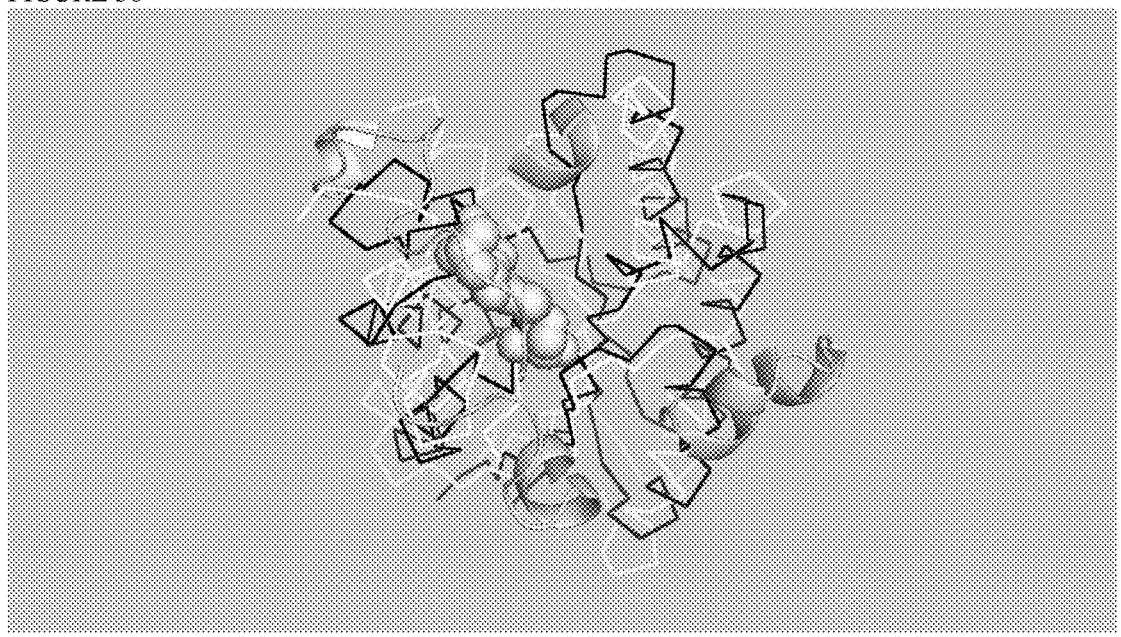
FIG. 36 shows the structural alignment between the lipid acyltransferase of *Aeromonas salmonicida* lipid acyltransferase comprising the N80D mutation and which is the mature sequence having undergone post-translational clipping [shown herein as SEQ ID No. 16] (white) and *E. coli* thioesterase (black) (PDB entry 1IVN) and shows insertion 4 (residues 213-381) in cartoon and the catalytic triad of the lipid acyltransferase (S16, D288, H291) is shown in space filling.
Figure 37:
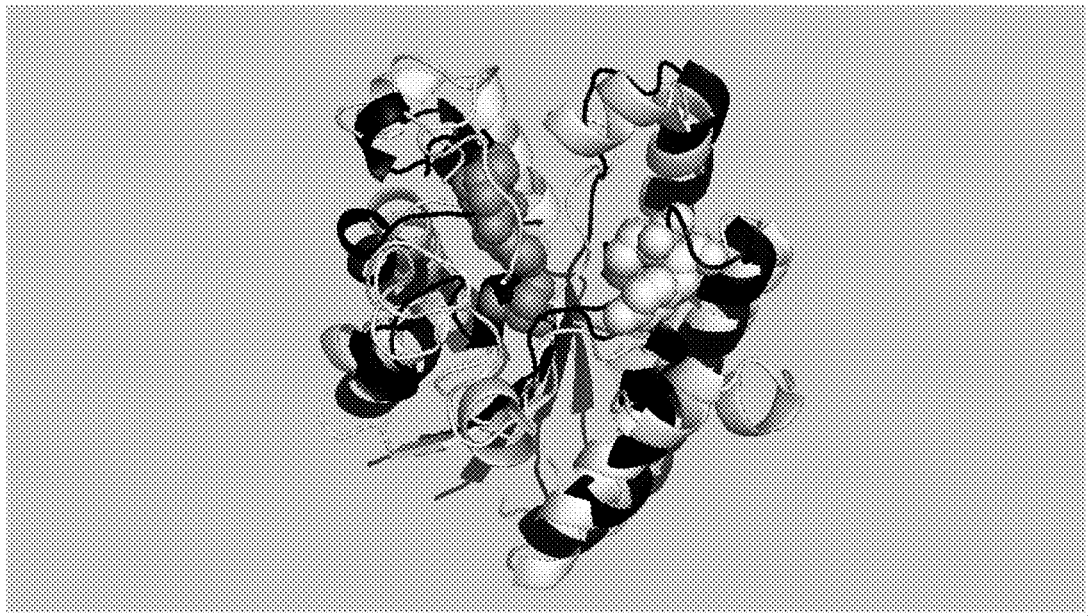
FIG. 37 shows the structural alignment between the lipid acyltransferase of *Aeromonas salmonicida* lipid acyltransferase comprising the N80D mutation and which is the mature sequence having undergone post-translational clipping [shown herein as SEQ ID No. 16] (white) and *E. coli* thioesterase (black) (PDB entry 1IVN) and shows the catalytic triad (S16, D288, H291) is shown in dark grey space filling and the residues forming the canyon (including Y117, A119 and Y120) shown in white space filling.

In the lipid acyltransferase, there is a large surface for substrate to bind that can be divided into two areas that are separated by Ser 16 and His 291, where Ser 16 and His 291 along with Asp288 form the characteristic catalytic triad. These two areas are shown in FIG. 30 and can be characterized as being a deep channel or "canyon" (marked with an arrow)—hereinafter referred to as the "canyon"—leading into an enclosed cavity or "cave" (marked with an arrow) running through the molecule.

The residues forming the canyon are listed in the Table below:

TABLE

| CANYON residues: | |
|---|---|
| Insertion 1 | M23, M27, Y30, L31 |
| Segment 1 | F42, G67, G68 |
| Insertion 2 | D80, P81, K82, Q84, V85, I86 |
| Segment 2a | Y117, A119, Y120 |
| Insertion 4 | G229, Y230, V231 |

The residues forming the cave are listed in table below.

TABLE

| CAVE residues: | |
|---|---|
| Segment 1 | D15, S16, L18 |
| Segment 2 | W111, A114, L115, L118 |
| Segment 3 | P156, D157, L158, Q160, N161 |
| Segment 4 | F206, A207, E208, M209, L210 |
| Segment 5 | M285, F286, V290, H291, P292 V295 |

Segments 3 and 4 precede insertions 3 and 4 respectively, and segment 5 immediately follows insertion 4. Insertions 4 and 5 also contribute to the over enclosure resulting in the cave, thus the cave is different to the canyon in that insertions 1 and 2 form the lining of the canyon while insertions 3 and 4 form the overlaying structure. Insertions 3 and insertion 4 cover the cave.

In one embodiment of the present invention a lipid acyltransferase may be altered by modifying the amino acid residues in one or more of the canyon, the cave, the insertion 1, the insertion 2, the insertion 3 or the insertion 4.

In one embodiment of the present invention a lipid acyltransferase may be altered by modifying the amino acid residues in one or more of the canyon, insertion 1 or insertion 2. In one embodiment, the dimensions of the acyl chain binding cavity of a lipid acyltransferase may be altered by making changes to the amino acid residues that form the larger cave. This may be done by modulating the size the regions that link the common features of secondary structure as discussed above. In particular, the size of the cave may be altered by changing the amino acids in the region between the last (fifth) beta strand of the enzyme and the Asp-X-X-His motif that forms part of the catalytic triad.

The substrate chain length specificity determining segment of a lipid acyltransferase is a region of contiguous amino acids that lies between the β5 β-strand of the enzyme and the Asp residue of the catalytic triad of that enzyme (the Asp residue being part of the Asp-Xaa-Xaa-His motif).

The tertiary structures of the *Aeromonas salmonicida* lipid acyltransferase and the *E. coli* thioesterase (deposited as NCBI's Genbank database as accession number 1IVN_A; GID:33357066) each showing a signature three-layer alpha/beta/alpha structure, where the beta-sheets are composed of five parallel strands allow the substrate chain length specificity determining segments of each of the lipid acyltransferase enzymes to be determined.

The substrate chain length specificity determining segment of the *Aeromonas salmonicida* lipid acyltransferase lies immediately N-terminal to the Asp residue of the catalytic triad of the enzyme. However, the length of the substrate chain length specificity determining segment may vary according to the distance between the Asp residue and the β5 β-strand of the enzyme. For example, the substrate chain length specificity determining segments of the lipid acyltransferase are about 13 amino, 19 amino acids and about 70 amino acids in length, respectively. As such, depending on the lipid acyltransferase, a substrate chain length specificity determining segment may be in the range of 10 to 70 amino acids in length, e.g., in the range of 10 to 30 amino acids in length, 30 to 50 amino acids in length, or 50 to 70 amino acids.

The Table below provides an exemplary sequence for the substrate chain length specificity determining segment of the lipid acyltransferase enzyme

| *A. salmonicida* lipid acyltransferase (GCAT) | |
|---|---|
| AEMLRDPQNFGLSDVENPCYDGGYVWKPFATRSV STDRQLSASPQERLAIAGNPLLAQAVASPMARRSA SPLNCEGKMF | SEQ ID No. 17 |

In certain embodiments, the amino acid sequence of a substrate chain length specificity determining segment may or may not be the amino acid sequence of a wild-type enzyme. In certain embodiments, the substrate chain length specificity determining segment may have an amino acid sequence that is at least 70%, e.g., at least 80%, at least 90% or at least 95% identical to the substrate chain length specificity determining segment of a wild type lipid acyltransferase.

Suitably the variant enzyme may be prepared using site directed mutagenesis.

Alternatively, the mutations may be prepared randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins (hereinafter referred to as "shuffling"). Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EPO 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded variant polypeptide by various means.

As a non-limiting example, in addition, mutations or natural variants of a polynucleotide sequence can be recombined with either the wild type or other mutations or natural variants to produce new variants. Such new variants can also be screened for improved functionality of the encoded polypeptide.

Preferred modifications are located at one or more of the following positions L031, 1086, M027, V085, A119, Y120, W122, E201, F235, W232, A236, and/or Q245.

In particular key modifications include one or more of the following modifications: L31Q, H, N, T, F, Y or C (preferably L31 Q); M27R, G, H, K, Y, D, N, V, C, Q, L, E, S or F (preferably M27V); V85H, R, D or E; I86R, Y, S, V, I, A, T, M, F, C or L (preferably I86S or A); A119T or I; Y120K or E; W122S, L or A (preferably W122L); E201R; Q245S; F235A or V; W232G or S; and/or A236G or E.

In one embodiment when the at least one modification is made in the canyon the modification(s) are made at one or more of the following positions: 31, 27, 85, 86, 119, 120.

In particular key modifications in the canyon include one or more of the following modifications: L31Q, H, N, T, F, Y or C (preferably L31 Q); M27R, G, H, K, Y, D, N, V, C, Q, L, E, S or F (preferably M27V); V85H, R, D or E; I86R, Y, S, V, I, A, T, M, F, C or L (preferably I86S or A); A119T or I; Y120K or E, which may be in combination with one another and/or in combination with a further modification.

In one embodiment preferably when the modification is made in insertion site 1 the modifications are made at one or more positions 31 and/or 27. Suitably the modifications may be L31Q, H, N, T, F, Y or C (preferably L31 Q) and/or M27R, G, H, K, Y, D, N, V, C, Q, L, E, S or F (preferably M27V).

In one embodiment preferably when the modification is made in insertion site 2 the modifications are made at positions are O85, O86. Suitably the modifications may be V85H, R, D or E and/or I86R, Y, S, V, I, A, T, M, F, C or L.

In one embodiment preferably when the modification is made in insertion site 4 the modifications are made at position 245. Suitably the modification may be Q245S.

In one embodiment preferably the modification is made in at least insertion site 1.

In another embodiment preferably a modification is made in at least insertion site 1 in combination with a further modification in insertion site 2 and/or 4 and/or at one or more of the following positions 119, 120, 122, 201, 77, 130, 82, 120, 207, 167, 227, 215, 230, 289.

In a further embodiment preferably a modification is made in at least the canyon region in combination with a further modification in insertion site 4 and/or at one or more of the following positions 122, 201, 77, 130, 82, 120, 207, 167, 227, 215, 230, 289.

Preferred modifications are given for particular site:
R130R, V, Q, H, A, D, L, I, K, N, C, Y, G, S, F, T or M;
K82R, N, H, S, L, E, T, M or G;
G121S, R, G, E, K, D, N, V, Q or A;
Y74Y or W;
Y83F or P;
I77T, M, H, Q, S, C, A, E, L, Y, F, R or V;
A207E;
Q167T, H, I, G, L or M;
D227L, C, S, E, F, V, I, T, Y, P, G, R, D, H or A;
N215G;
Y230A, G, V, R, I, T, S, N, H, E, D, Q, K; or
N289P.

In combination with one or more modifications at positions 31, 27, 85, 86, 119, 120, 122, 201, 245, 235, 232, and/or 236 (for example the modification may be one or more of the following: L31Q, H, N, T, F, Y or C (preferably L31 Q); M27R, G, H, K, Y, D, N, V, C, Q, L, E, S or F (preferably M27V); V85H, R, D or E; I86R, Y, S, V, I, A, T, M, F, C or L (preferably I86S or A); A119T or I; Y120K or E; W122S, L or A (preferably W122L); E201R; Q245S; F235A or V; W232G or S; and/or A236G or E) suitably the variant lipid acyltransferase may be additionally modified at one or more of the following positions 130, 82, 121, 74, 83, 77, 207, 167, 227, 215, 230, 289 (for example the additional modification may be one or more of the following: R130R, V, Q, H, A, D, L, I, K, N, C, Y, G, S, F, T or M; K82R, N, H, S, L, E, T, M or G; G121S, R, G, E, K, D, N, V, Q or A; Y74Y or W; Y83F or P; I77T, M, H, Q, S, C, A, E, L, Y, F, R or V; A207E; Q167T, H, I, G, L or M; D227L, C, S, E, F, V, I, T, Y, P, G, R, D, H or A; N215G; Y230A, G, V, R, I, T, S, N, H, E, D, Q, K; and/or N289P), preferably the variant lipid acyltransferase may be additionally modified at least one or more of the following positions: 130, 82, 77 or 227.

For the avoidance of doubt the lipid acyltransferase backbone when aligned (on a primary or tertiary basis) with the lipid acyltransferase enzyme shown herein as SEQ ID No. 6 preferably has D in position 80. We have therefore shown in many of the combinations taught herein N80D as a modification. If N80D is not mentioned as a suitable modification and the parent backbone does not comprise D in position 80, then an additional modification of N80D should be incorporated into the variant lipid acyltransferase to ensure that the variant comprises D in position 80.

When the backbone or parent lipid acyltransferase already contains the N80D modification, the other modifications can be expressed without referencing the N80D modification, i.e. L31Q, N80D, W122L could have been expressed as L31Q, W122L for example.

However, it is important to note that the N80D modification is a preferred modification and a backbone enzyme or parent enzyme is preferably used which already possesses amino acid D in position 80. If, however, a backbone is used which does not contain amino acid D in position (such as one more of the lipid acyltransferases shown here as SEQ ID No. 1, 3, 4, 5, 8, or 9 for instance) then preferably an additional modification of N80D is included.

In one embodiment the present invention relates to a method of producing a variant lipid acyltransferase, said method comprising:
(a) substituting at least one amino acid residue at at least position 27 or 31 of a parent lipid acyltransferase, which position is identified by alignment of the parent sequence with SEQ ID No. 16 or SEQ ID No. 6 to produce a variant lipid acyltransferase;
(b) measuring the ability of the variant lipid acyltransferase to transfer an acyl group to maltose compared with said parent lipid acyltransferase; and
(c) selecting a variant lipid acyltransferase having an improved ability to transfer an acyl group to maltose as compared with the parent lipid acyltransferase.

Suitably the substitution at position 27 or 31 is identified by alignment of the parent sequence with SEQ ID No. 16 or SEQ ID No. 6. In addition or alternatively, the substitution at position 31 may be a substitution to an amino acid residue selected from the group consisting of: Q, H, Y, N, T, F, Y and C, preferably Q. The substitution at position 27 may be a substitution to an amino acid residue selected from the group consisting of: R, G, H, K, Y, D, N, V, C, Q and L preferably V.

The present invention also relates to a method of preparing a variant lipid acyltransferase said method comprising:
(a) substituting at least one amino acid residue at at least position 31 of a parent lipid acyltransferase to glutamine, which position is identified by alignment of the parent sequence with SEQ ID No. 16 or SEQ ID No. 6;
(b) wherein the variant lipid acyltransferase has a maltose transferase activity of at least 0.0282% when using the maltose transferase assay provided in protocol 1.

The present invention further relates to a variant lipid acyltransferase obtainable (or obtained) by any of the methods of the present invention.

Suitably, the substitution at position 31 identified by alignment of the parent sequence with SEQ ID No. 16 or SEQ ID No. 6 may be a substitution to an amino acid residue selected from the group consisting of: Q, H, Y and F, preferably Q.

Suitably, the variant polypeptide comprises one or more further modification(s) at any one or more of amino acid residue positions: 27, 77, 80, 82, 85, 85, 86, 121, 122, 130, 167, 207, 227, 230 and 289, which position is identified by alignment of the parent sequence with SEQ ID No. 16. Suitably, at least one of the one or more further modification(s) may be at amino acid residue position: 86, 122 or 130, which position is identified by alignment of the parent sequence with SEQ ID No. 16.

Suitably, the variant lipid acyltransferase comprises one or more of the following further substitutions: I86 (A, C, F, L, M, S, T, V, R, I or Y); W122 (S, A, F, W, C, H, L, M, R or Y); R130A, C, D, G, H, I, K, L, M, N, Q, T, V, R, F or Y); or any combination thereof.

Suitably the variant lipid acyltransferase may comprises at least one mutation as taught in Tables 1 and/or 2 of the Examples presented herewith or a combination of modifications as taught in Tables 3 and/or 4 of the Examples presented herewith.

The variant lipid acyltransferase may comprise one of the following combinations of modifications (where the parent back bone already comprises amino acid D in position 80, the modification can be expressed without reference to N80D):

L31Q, N80D, I86S, W122F
L31Q, N80D, W122L
L31Q, N80D, I86V, W122L
L31Q, N80D, I86I, W122L
L31Q, N80D, I86S, R130R
L31Q, N80D, K82R, I86A
L31Q, N80D, I86S, W122W
L31Q, N80D, I86S, W122Y
M27V, L31Q, N80D
L31Q, N80D, I86A, W122L
L31Q, N80D, W122L
L31Q, N80D, I86S, G121S
L31Q, N80D, I86S
L31Q, N80D, K82R, I86S
L31Q, N80D, I86S, W122L, R130Y
L31Q, N80D, I86S, W122L, R130V
L31Q, N80D, I86S
L31Q, N80D, I86T, W122L
L31Q, N80D, I86S, W122L
L31Q, N80D, W122L, R130Q
L31Q, N80D, I86S, W122L, R130R
L31Q, N80D, I86S
L31Q, N80D, G121R
L31Q, N80D, I86A
M27C, L31Q, N80D
M27Q, L31Q, N80D
L31Q, N80D, G121S
L31Q, N80D, I86S, W122R
L31Q, N80D, R130Q
L31Q, N80D, I86S, W122H
L31Q, N80D, I86M, W122L
L31Q, N80D, R130N
L31Q, N80D, I86S, W122L
L31Q, N80D, K82N
L31Q, N80D, I86S, W122M
L31Q, N80D, W122L
L31Q, N80D, K82H
L31Q, N80D, R130H
L31Q, N80D, R130A
L31Q, N80D, G121S
L31Q, N80D, I86S, W122L, R130D
L31Q, N80D, I86M
L31Q, Y74Y, N80D
L31Q, N80D, R130L
L31Q, N80D, Y83F
L31Q, N80D, K82S
L31Q, I77T, N80D
L31Q, N80D, I86S, W122L, R130I
L31Q, N80D, I86S, W122L
L31Q, N80D, I86F, W122L
M27N, L31Q, N80D
L31Q, N80D, Y83P
L31Q, N80D, R130K
L31Q, N80D, K82R, I86S, W122L
L31Q, N80D, K82L
L31Q, N80D, I86S, G121G
L31Q, N80D, I86A, R130Q
M27H, L31Q, N80D
L31Q, N80D, W122L, A207E
L31Q, N80D, W122L, R130L
L31Q, N80D, K82E
L31Q, N80D, G121E
L31Q, N80D, W122L, R130R
L31Q, I77M, N80D
L31Q, N80D, K82T
L31Q, N80D, W122L
L31Q, N80D, W122H
L31Q, N80D, Q167T
L31Q, I77H, N80D
L31Q, N80D, G121K
L31Q, I77Q, N80D
L31Q, N80D, W122L, R130N
L31Q, N80D, W122L
L31Q, N80D, G121D
L31Q, N80D, R130T
L31Q, N80D, R130T
L31Q, N80D, K82M
L31Q, N80D, Q167H
L31Q, N80D, I86T
L31Q, N80D, Q167I
L31Q, N80D, I86C
L31Q, N80D, Q167G
M27L, L31Q, N80D
L31Q, N80D, I86S, G121R
L31Q, I77S, N80D
L31Q, I77C, N80D
L31Q, N80D, G121N
L31Q, I77A, N80D
L31Q, N80D, R130M
L31Q, N80D, W122F
M27G, L31Q, N80D
L31Q, N80D, K82G
L31Q, N80D, I86S, W122L, R130K
L31Q, N80D, R130A
L31Q, N80D, I86I
L31Q, I77E, N80D
L31Q, N80D, D227L
L31Q, N80D, V85H, N215G
L31Q, N80D, I86A, W122L, R130N
L31Q, I77R, N80D
L31Q, N80D, I86F
L31Q, N80D, I86Y, W122L
M27K, L31Q, N80D
L31Q, N80D, D227C
L31Q, N80D, R130L
L31Q, N80D, I86C, W122L
L31Q, N80D, Q167L
L31Q, N80D, V85H
L31Q, N80D, Q167M
M27D, L31Q, N80D
L31Q, N80D, I86L
L31Q, N80D, Y230A
L31Q, N80D, W122R
L31Q, N80D, Y230G
L31Q, N80D, D227S
L31Q, N80D, W122L, A207E, N289P
L31Q, N80D, W122Y
L31Q, N80D, I86L, W122L
L31Q, N80D, K82R, I86S, G121S, R130Q
L31Q, Y74W, N80D
L31Q, N80D, R130F
L31Q, N80D, G121V
L31Q, N80D, W122L, R130M
L31Q, N80D, R130V
L31Q, N80D, Y230V
L31Q, N80D, N215G
L31Q, N80D, I86S, W122L, R130N

L31Q, N80D, Y230R
M27E, L31Q, N80D
L31Q, N80D, Y230I
L31Q, N80D, I86S, W122L, R130S
L31Q, N80D, K82R
L31Q, N80D, D227E
L31Q, N80D, K82R, I86A, G121S
L31Q, N80D, R130G
L31Q, I77V, N80D
L31Q, N80D, G121G
L31Q, N80D, Y230T
L31Q, N80D, K82R, I86S, R130N
L31Q, N80D, D227F
L31Q, N80D, I86A, G121R
L31Q, N80D, I86S, R130N
L31Q, N80D, W122C
L31Q, N80D, Y230S
L31Q, N80D, R130Y
L31Q, N80D, R130C
L31Q, I77L, N80D
A119T, N80D
A199A, N80D
G67A, N80D, V85H wherein said positions are identified by alignment of the parent sequence with SEQ ID No. 16 or SEQ ID No. 6.

Suitably, the variant lipid acyltransferase may be identical to the parent lipid acyltransferase except for a modification at position 31 and, optionally, one or more further modification(s) at any one or more of amino acid residue positions: 27, 77, 80, 82, 85, 85, 86, 121, 122, 130, 167, 207, 227, 230 and 289, which position is identified by alignment of the parent sequence with SEQ ID No. 16 or SEQ ID No. 6.

Suitably, the variant lipid acyltransferase may be identical to the parent lipid acyltransferase except for a modification at position 31 and, optionally, one or more further modification(s) at any one or more of amino acid residue positions: 86, 122 or 130, which position is identified by alignment of the parent sequence with SEQ ID No. 16 or SEQ ID No. 6.

In one embodiment, where the parent sequence is SEQ ID No. 6 or SEQ ID No. 16 or where the parent sequence is encoded by SEQ ID No. 10 or SEQ ID No. 25, the variant polypeptide has any one of the modifications as detailed above, except for a modification at position 80. In this regard, SEQ ID No. 6, SEQ ID No. 16 or a polypeptide encoded by SEQ ID No. 10 or SEQ ID No. 25 will already have aspartic acid at position 80, when said positions are identified by alignment of the parent sequence with SEQ ID No. 6.

Suitably, the variant lipid acyltransferase or the variant lipid acyltransferase obtainable by a method according to the present invention may have at least 75% identity to the parent lipid acyltransferase, suitably the variant lipid acyltransferase may have at least 75% or at least 80% or at least 85% or at least 90% or at least 95% or at least 98% identity to the parent lipid acyltransferase.

The present invention also relates to a variant polypeptide having lipid acyltransferase activity, wherein the variant comprises a modification at at least position 31 compared to a parent lipid acyltransferase, wherein position 31 is identified by alignment with SEQ ID No. 16 or SEQ ID No. 6 and wherein the variant lipid acyltransferase has a maltose transferase activity of at least 0.0282% when using the maltose transferase assay provided in protocol 1.

In one embodiment preferably the variant lipid acyltransferase has the following modifications and/or the following modifications are made in the methods of the present invention:

L31Q, N80D, W122L (which can be expressed as L31Q, W122L where the backbone enzyme already has D in position 80);
M27V, L31Q, N80D (which can be expressed as N27V, L31Q where the backbone enzyme already has D in position 80);
L31Q, N80D, K82R, I86A (which can be expressed as L31Q, K82R, I86A where the backbone enzyme already has D in position 80); and/or
L31Q, N80D, I86S, W122F (which can be expressed as L31Q, I86S, W122F where the backbone enzyme already has D in position 80).

In another embodiment (particularly when the variant is to be used in degumming edible oils) preferably the variant lipid acyltransferase has the following modifications and/or the following modifications are made in the methods of the present invention:

A119T, N80D (which can be expressed as A119T where the backbone enzyme already has D in position 80);
A119A, N80D (which can be expressed as A119A where the backbone enzyme already has D in position 80);
G67A, V85H, N80D (which can be expressed as G67A, V85H where the backbone enzyme already has D in position 80).

In another aspect, the present invention provides a variant polypeptide having lipid acyltransferase activity, wherein the variant comprises a modification at at least position 31 compared to a parent lipid acyltransferase, wherein position 31 is identified by alignment with SEQ ID No. 16 and wherein the variant lipid acyltransferase has a carbohydrate (preferably maltose) transferase activity of at least 0.0282% when using the carbohydrate transferase assay provided in protocol 1 herein after disclosed.

Preferably when the improved property relates to an improved carbohydrate transferase activity (e.g. maltose transferase activity) the variant lipid acyltransferase has a carbohydrate transferase activity (e.g. maltose transferase activity) of at least 0.0282% when using the maltose transferase assay provided in protocol 1 herein defined below.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, NY (1991) provide those of skill in the art with a general dictionary of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a", "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The term "modifying" as used herein means adding, substituting and/or deleting. Preferably the term "modifying" means "substituting".

The term "lipid acyltransferase" as used herein means an enzyme which has acyltransferase activity (for example an enzyme classified as E.C. 2.3.1.x, in particular 2.3.1.43 in accordance with the Enzyme Nomenclature Recommendations (1992) of the Nomenclature Committee of the International Union of Biochemistry and Molecular Biology), whereby the enzyme is capable of transferring an acyl group from a lipid to one or more acceptor substrates, including, but not limited to, a sterol; a stanol; a carbohydrate (e.g. maltose and/or glucose); a protein; a protein subunit; cholesterol, an alcohol, and glycerol.

The term "galactolipid" as used herein means one or more of DGDG or DGMG.

The term "phospholipid" as used herein means lecithin, including phosphatidylcholine.

The term "lecithin" as used herein encompasses phosphatidylcholine, phosphatidylethanolamine, phosphatidylinositol, phosphatidylserine and phosphatidylglycerol.

The term "polar lipid" as used herein means a phospholipid and/or a galactolipid, preferably a phospholipid and a galactolipid.

The term "transferase" as used herein is interchangeable with the term "lipid acyltransferase".

The term "galactolipid transferase activity" as used herein means the ability of the enzyme to catalyse the transfer of an acyl group from a galactolipid donor to an acceptor molecule (other than water).

Likewise, the term "phospholipids transferase activity" as used herein means the ability of the enzyme to catalyse the transfer of an acyl group from a phospholipids donor to an acceptor molecule (other than water).

Suitably, the lipid acyltransferase as defined herein catalyses one or more of the following reactions: interesterification, transesterification, alcoholysis, hydrolysis. Preferably the lipid acyltransferase as defined herein catalyses one or more of the following reactions: transesterification, alcoholysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule. Acyl transfer which results from hydrolysis requires the separation of the water molecule.

The term "improved properties" or "improved activity" as used herein means that the variant enzyme has a property or activity which is more desired (i.e. it could be higher or lower) when compared with that property or activity of the parent (or backbone) enzyme.

The term "an increased ratio of transferase activity compared with hydrolysis activity" as used herein means the variant enzyme when compared with the parent enzyme is able to catalyse lipid transferase at a higher rate compared with lipid hydrolysis. This may mean that both lipid transferase activity and lipid hydrolysis activity are increased compared with the parent enzyme or that lipid transferase activity is increased whilst lipid hydrolysis activity is decreased compared with the parent enzyme. It is the final relation between the two activities which is important.

Preferably, the lipid substrate upon which the parent lipid acyltransferase and/or the variant lipid acyltransferase according to the present invention acts is one or more of the following lipids, including, but not limited to, a phospholipid, such as a lecithin, e.g. phosphatidylcholine, a triacylglyceride, a cardiolipin, a diglyceride, or a glycolipid, such as digalactosyldiglyceride (DGDG) or monogalactosyldiglyceride (MGDG) for example.

This lipid substrate may be referred to herein as the "lipid acyl donor".

For some aspects, preferably the lipid substrate upon which the parent lipid acyltransferase and/or the variant lipid acyltransferase acts is a phospholipid, such as lecithin, for example phosphatidylcholine.

In some embodiments, the lipid substrate may be a food lipid, that is to say a lipid component of a foodstuff.

Suitably, the lipid substrate or lipid acyl donor may be one or more lipids present in one or more of the following substrates, including, but not limited to, fats, including lard, tallow and butter fat; oils including oils extracted from or derived from palm oil, sunflower oil, soya bean oil, safflower oil, cotton seed oil, ground nut oil, corn oil, olive oil, peanut oil, coconut oil, and rape seed oil. Lecithin from soya, rape seed or egg yolk is also a suitable lipid substrate. The lipid substrate may be an oat lipid or other plant based material containing galactolipids.

In one aspect the lipid acyl donor is preferably lecithin (such as phosphatidylcholine) in egg yolk.

For some aspects of the present invention, the lipid may be selected from lipids having a fatty acid chain length of from 8 to 22 carbons.

For some aspects of the present invention, the lipid may be selected from lipids having a fatty acid chain length of from 16 to 22 carbons, more preferably of from 16 to 20 carbons.

For some aspects of the present invention, the lipid may be selected from lipids having a fatty acid chain length of no greater than 14 carbons, suitably from lipids having a fatty acid chain length of from 4 to 14 carbons, suitably 4 to 10 carbons, suitably 4 to 8 carbons.

For some aspects of the present invention, the variant lipid acyltransferase according to the present invention may utilize a protein as the acyl acceptor. Suitably, the protein may be one or more of the proteins found in a food product, for example in a dairy product and/or a meat product. By way of example only, suitable proteins may be those found in curd or whey, such as lactoglobulin. Other suitable proteins include ovalbumin from egg, gliadin, glutenin, puroindoline, lipid transfer proteins from grains, and myosin from meat.

Suitably the parent enzymes may include any enzyme with esterase or lipase activity—and therefore an esterase or a lipase could be used as a parent enzyme in the methods of the present invention in some instances.

However, preferably the parent enzyme is a lipid acyltransferase enzyme.

Preferably, the parent enzyme aligns to the pfam00657 consensus sequence.

The term a "parent lipid acyltransferase" and "parent sequence" is used interchangeably herein.

In relation to the method claims of the present invention the "parent lipid acyltransferase" may refer to the sequence that is modified (i.e. the sequence to which a modification is made).

The parent lipid acyl transferase for use in any one of the methods of the present invention may be a natural lipid acyl transferase or a variant lipid acyl transferase.

For instance, the nucleotide sequence encoding a parent lipid acyl transferase for use in the present invention may be one as described in WO2004/064537, WO2004/064987, WO2005/066347, or WO2006/008508. These documents are incorporated herein by reference.

The term "lipid acyltransferase" as used herein means an enzyme which has acyltransferase activity (for example an enzyme classified as E.C. 2.3.1.x, in particular 2.3.1.43 in accordance with the Enzyme Nomenclature Recommendations (1992) of the Nomenclature Committee of the International Union of Biochemistry and Molecular Biology), whereby the enzyme is capable of transferring an acyl group from a lipid to one or more acceptor substrates, such as one or more of the following, including, but not limited to, a sterol; a stanol; a carbohydrate (e.g. maltose and/or glucose); a protein; a protein subunit; cholesterol, an alcohol, and glycerol.

Preferably the parent and/or variant lipid acyltransferase is one classified under the Enzyme Nomenclature classification (E.C. 2.3.1.43).

Suitable lipid acyltransferases for use as parent enzymes in accordance with the present invention may be identified by use of the following assay entitled "Lipid acyltransferase assay". In addition, variant enzymes in accordance with the present invention also preferably are lipid acyltransferases when classified using the "Lipid acyltransferase assay" and/or the assay detailed in Protocol 1 and/or the assay detailed in Protocol 2 shown below.

"Lipid Acyltransferase Assay"

Substrate: 50 mg Cholesterol (Sigma C8503) and 450 mg Soya phosphatidylcholine(PC), Avanti #441601 is dissolved in chloroform, and chloroform is evaporated at 40° C. under vacuum.

300 mg PC:cholesterol 9:1 is dispersed at 40° C. in 10 ml 50 mM HEPES buffer pH 7.

Enzymation:
250 µl substrate is added in a glass with lid at 40° C.
25 µl enzyme solution is added and incubated during agitation for 10 minutes at 40° C.
The enzyme added should esterify 2-5% of the cholesterol in the assay.
Also a blank with 250 water instead of enzyme solution is analysed.
After 10 minutes 5 ml Hexan:Isopropanol 3:2 is added.
The amount of cholesterol ester is analysed by HPTLC using Cholesteryl stearate (Sigma C3549) standard for calibration.
Transferase activity is calculated as the amount of cholesterol ester formation per minute under assay conditions.

One Transferase Unit (TrU) is defined as µmol cholesterol ester produced per minute at 40° C. and pH 7 in accordance with the transferase assay given above.

If the enzyme exhibits a specific transferase unit (TrU) per mg enzyme of at least 25 TrU/mg enzyme protein then it would be considered a lipid acyltransferase suitable for use as a parent enzyme in the methods of the present invention.

In addition preferably the variant lipid acyltransferases of the present invention and for use in the present invention have a specific transferase unit (TrU) per mg enzyme of at least 25 TrU/mg enzyme protein when determined using the lipid acyltransferase assay given above.

Suitably the variant lipid acyltransferase for use in the present invention may be dosed in amount of 0.05 to 50 TrU per g oil, suitably in an amount of 0.5 to 5 TrU per g oil.

Preferably when aligned with the Pfam00657 consensus sequence the parent and/or variant lipid acyltransferase for use in the methods or uses of the invention may have at least one, preferably more than one, preferably more than two, of the following, a GDSx (SEQ ID NO: 48) block, a GANDY (SEQ ID NO: 49) block, a HPT block. Suitably, the lipid acyltransferase may have a GDSx (SEQ ID NO: 48) block and a GANDY (SEQ ID NO: 49) block. Alternatively, the enzyme may have a GDSx (SEQ ID NO: 48) block and a HPT block. Preferably the enzyme comprises at least a GDSx (SEQ ID NO: 48) block. See WO2004/064537 or WO2004/064987 for further details.

Preferably, residues of the GANDY (SEQ ID NO: 49) motif are selected from GANDY (SEQ ID NO: 49), GGNDA (SEQ ID NO: 51), GGNDL (SEQ ID NO: 52), most preferably GANDY (SEQ ID NO: 49).

Suitably, the parent and/or variant lipid acyltransferase may comprise a GDSx (SEQ ID NO: 48) motif and/or a GANDY (SEQ ID NO: 49) motif.

In some aspects, the parent lipid acyltransferase enzyme and/or the variant lipid acyltransferase may be characterised as an enzyme which possesses lipid acyltransferase activity and which comprises the amino acid sequence motif GDSX (SEQ ID NO: 48), wherein X is one or more of the following amino acid residues L, A, V, I, F, Y, H, Q, T, N, M or S.

Preferably the parent and/or the variant lipid acyltransferase comprises a GDSX (SEQ ID NO: 48) motif.

The GDSX (SEQ ID NO: 48) motif is comprised of four conserved amino acids. Preferably, the serine within the motif is a catalytic serine of the lipid acyltransferase enzyme. Suitably, the serine of the GDSX (SEQ ID NO: 48) motif may be in a position corresponding to Ser-16 in *Aeromonas hydrophila* lipolytic enzyme taught in Brumlik & Buckley (Journal of Bacteriology April 1996, Vol. 178, No. 7, p 2060-2064).

To determine if a protein has the GDSX (SEQ ID NO: 48) motif according to the present invention, the sequence is preferably compared with the hidden markov model profiles (HMM profiles) of the pfam database.

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft D H (2002) Brief Bioinform 3; 236-245 and Bateman A et al, Nucleic Acids Res. 2002 Jan. 1; 30(1):276-80.

For a detailed explanation of hidden Markov models and how they are applied in the Pfam database see Durbin R, Eddy S, and Krogh A (1998) Biological sequence analysis; probabilistic models of proteins and nucleic acids. Cambridge University Press, ISBN 0-521-62041-4. The Hammer software package can be obtained from Washington University, St Louis, USA.

Alternatively, the GDSX (SEQ ID NO: 48) motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

The PFAM database can be accessed, for example, through several servers which are currently located at the following websites.

Wellcome Trust Sanger Institute (UK)
Washington University in St. Louis
French National Institute for Agricultural Research (INRA)
Karolinska Institutet (KI)

The database offers a search facility where one can enter a protein sequence. Using the default parameters of the database the protein sequence will then be analysed for the presence of Pfam domains. The GDSX (SEQ ID NO: 48) domain is an established domain in the database and as such its presence in any query sequence will be recognised. The database will return the alignment of the Pfam00657 consensus sequence to the query sequence.

Suitably, the parent lipid acyltransferase may be obtainable, preferably obtained, from an organism from one of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*. Suitably, the lipid acyltransferase may be obtainable, suitably may be obtained, from an organism from the genus *Aeromonas*.

Suitably, the parent lipid acyltransferase enzyme may be encoded by one of the following nucleotide sequences:
(a) the nucleotide sequence shown as SEQ ID No. 25;
(b) the nucleotide sequence shown as SEQ ID No. 10;
(c) the nucleotide sequence shown as SEQ ID No. 11;
(d) the nucleotide sequence shown as SEQ ID No. 12;
(e) the nucleotide sequence shown as SEQ ID No. 13;
(f) the nucleotide sequence shown as SEQ ID No. 14;
(g) the nucleotide sequence shown as SEQ ID No. 15;
(h) a nucleotide sequence which has 70% or more (preferably 75% or more, 85% or more, 95% or more or 98% or more) identity with any one of the sequences shown as SEQ ID No. 25, SEQ ID No. 10, SEQ ID No. 11, SEQ ID No. 12, SEQ ID No. 13, SEQ ID No. 14 or SEQ ID No. 15;
(i) a nucleotide sequence which is related to SEQ ID No. 25, SEQ ID No. 10, SEQ ID No. 11, SEQ ID No. 12, SEQ ID No. 13, SEQ ID No. 14, SEQ ID No. 15 by the degeneration of the genetic code; or
(j) a nucleotide sequence which hybridizes under medium or high stringency conditions with any one of the sequences shown as SEQ ID No. 25, SEQ ID No. 10, SEQ ID No. 11, SEQ ID No. 12, SEQ ID No. 13, SEQ ID No. 14 or SEQ ID No. 15.

In one embodiment, the nucleotide sequence encoding a parent lipid acyltransferase enzyme in accordance with the present invention may be a nucleotide sequence which has 70% or more, 75% or more, 80% or more, preferably 85% or more, more preferably 90% or more, even more preferably 95% or more, such as 98 or 99% ore more, identity the sequence shown as SEQ ID No. 10 or SEQ ID No. 25.

Suitably, the parent lipid acyl transferase enzyme may comprise (or consist of) one of the following amino acid sequences:
(i) the amino acid sequence shown as SEQ ID No. 16
(ii) the amino acid sequence shown as SEQ ID No. 3
(iii) the amino acid sequence shown as SEQ ID No. 4
(iv) the amino acid sequence shown as SEQ ID No. 1
(v) the amino acid sequence shown as SEQ ID No. 5
(vi) the amino acid sequence shown as SEQ ID No. 6
(vii) the amino acid sequence shown as SEQ ID No. 8
(viii) the amino acid sequence shown as SEQ ID No. 9 or an amino acid sequence which has 75%, 80%, 85%, 90%, 95%, 98% or more identity with any one of the sequences shown as SEQ ID No. 16, SEQ ID No. 1, SEQ ID No. 3, SEQ ID No. 4, or SEQ ID No. 5, SEQ ID No. 6, SEQ ID No. 8 or SEQ ID No. 9.

Suitably, the parent lipid acyl transferase enzyme of the present invention may be a lipid acyltransferase that comprises (or consists of) either the amino acid sequence shown as SEQ ID No. 6 or 16, or comprises (or consists of) an amino acid sequence which has 75% or more, preferably 80% or more, preferably 85% or more, preferably 90% or more, preferably 95% or more, identity with the amino acid sequence shown as SEQ ID No. 16 or the amino acid sequence shown as SEQ ID No. 6.

Suitable parent lipid acyltransferases are known in the art. For example the lipid acyltransferases taught in WO2009/081094 (incorporated herein by reference) are suitable as parent lipid acyltransferases in accordance with the present invention.

The parent lipid acyltransferase enzyme may be a phospholipid glycerol acyl transferase. Phospholipid glycerol acyl transferases include those isolated from *Aeromonas* spp., preferably *Aeromonas hydrophila* or *A. salmonicida*, most preferably *A. salmonicida* or variants thereof.

It will be recognized by the skilled person that it is preferable that the signal peptides of the acyl transferase has been cleaved during expression of the transferase. The signal peptide of SEQ ID Nos. 1, 3, 4 and 5 are amino acids 1-18. Therefore the most preferred regions are amino acids 19-335 for SEQ ID No. 1 and SEQ ID No. 3 (*A. hydrophila*) and amino acids 19-336 for SEQ ID No. 4 and SEQ ID No. 5 (*A. salmonicida*). When used to determine the homology of identity of the amino acid sequences, it is preferred that the alignments as herein described use the mature sequence, i.e. without the signal peptide for instance.

In one embodiment, suitably the lipid acyl transferase for use in the present invention comprises (or consists of) the amino acid sequence shown in SEQ ID No. 16 or comprises (or consists of) an amino acid sequence which has at least 70%, at least 75%, at least 85%, at least 90%, at least 95%, at least 98% identity to SEQ ID No. 16.

Therefore the most preferred regions for determining homology (identity) are amino acids 19-335 for SEQ ID No. 1 and 3 (*A. hydrophila*) and amino acids 19-336 for SEQ ID Nos. 4, 15 and 16 (*A. salmonicida*). SEQ ID Nos. 8 and 9 are mature protein sequences of a lipid acyl transferase from *A. hydrophila* and *A. salmonicida* respectively which may or may not undergo further post-translational modification.

Suitable parent lipid acyltransferases for use in accordance with the present invention and/or in the methods of the present invention may comprise any one of the following amino acid sequences and/or be encoded by the following nucleotide sequences:
(a) a nucleic acid which encodes a polypeptide exhibiting lipid acyltransferase activity and is at least 70% identical (preferably at least 80%, more preferably at least 90%, even more preferably at least 95, such as at least 98%, identical) with the polypeptide sequence shown in SEQ ID No. 6 or with the polypeptide shown in SEQ ID No. 16;
(b) a (isolated) polypeptide comprising (or consisting of) an amino acid sequence as shown in SEQ ID No. 16 or SEQ ID No. 6 or an amino acid sequence which is at least 70% identical (preferably at least 80% identical, more preferably at least 90% identical, even more preferably at least 95, such as at least 98%,) with SEQ ID No. 6 or SEQ ID No. 16;
(c) a nucleic acid encoding a lipid acyltransferase, which nucleic acid comprises (or consists of) a nucleotide sequence shown as SEQ ID No. 10 or SEQ ID No. 25 or a nucleotide sequence which is at least 70% identical (preferably at least 80%, more preferably at least 90% identical) with the nucleotide sequence shown as SEQ ID No. 10 or SEQ ID No. 25;
(d) a nucleic acid which hybridizes under medium or high stringency conditions to a nucleic acid probe comprising the nucleotide sequence shown as SEQ ID No. 10 or SEQ ID No. 25 and encodes for a polypeptide exhibiting lipid acyltransferase activity;

(e) a nucleic acid which is a fragment of the nucleic acid sequences specified in a), c) or d); or (f) a polypeptide which is a fragment of the polypeptide specified in b).

Preferably, nucleotide sequences encoding a parent lipid acyltransferase for use in the present invention may be a polynucleotide encoding a lipid acyltransferase (such as SEQ ID No. 6 or SEQ ID No. 16).

In one embodiment preferably the nucleotide sequence is expressed in *Bacillus licheniformis* by transforming said *B. licheniformis* with a nucleotide sequence shown in SEQ ID No. 10 or SEQ ID No. 25 or a nucleotide sequence having at least 75% with SEQ ID No. 10 or SEQ ID No. 25 (more preferably at least 80%, more preferably at least 85%, more preferably at least 95%, more preferably at least 98% identity therewith) or with a modified nucleotide sequence in accordance with the present invention; culturing said *B. licheniformis* and isolating the lipid acyltransferase(s) produced thereby.

Preferably, the parent lipid acyltransferase enzyme according to the present invention comprises the following catalytic triad: Ser 16, Asp 288 and His 291 (these residue numbers refer to the mature sequences shown in SEQ ID No. 6 and 16 for example). Ser 16, Asp 288 and His 291 comprises a serine residue, an aspartic acid residue and a histidine residue, respectively, at positions corresponding to Ser-34, Asp-306 and His-309 in the *Aeromonas hydrophila* lipid acyl transferase enzyme shown in SEQ ID No. 3 or SEQ ID No. 1, i.e. the immature sequences which comprise a signal peptide—which forms the first 18 amino acid residues of these sequences. In the pfam00657 consensus sequence, as given in FIG. 3 (SEQ ID No. 2) the active site residues correspond to Ser-7, Asp-345 and His-348.

Suitably the variant lipid acyltransferase is one classified under the Enzyme Nomenclature classification (E.C. 2.3.1.43).

Suitably, the variant lipid acyltransferase according to the present invention may exhibit one or more of the following lipase activities: glycolipase activity (E.C. 3.1.1.26), triacylglycerol lipase activity (E.C. 3.1.1.3), phospholipase A2 activity (E.C. 3.1.1.4) or phospholipase A1 activity (E.C. 3.1.1.32). The term "glycolipase activity" as used herein encompasses "galactolipase activity".

Suitably, the variant lipid acyltransferase according to the present invention may have at least one or more of the following activities: glycolipase activity (E.C. 3.1.1.26) and/or phospholipase A1 activity (E.C. 3.1.1.32) and/or phospholipase A2 activity (E.C. 3.1.1.4). For some aspects, the variant lipid acyltransferase according to the present invention may have at least glycolipase activity (E.C. 3.1.1.26).

Suitably, for some aspects the variant lipid acyltransferase according to the present invention may be capable of transferring an acyl group from a glycolipid and/or a phospholipid to one or more of the following acceptor substrates: a sterol, a stanol, a carbohydrate (e.g. maltose, and/or glucose for example), a protein, glycerol.

For some aspects, preferably the variant lipid acyltransferase according to the present invention does not exhibit triacylglycerol lipase activity (E.C. 3.1.1.3).

The variant lipid acyltransferase may have one or more modifications as discussed in detail above and/or may be prepared by the methods of the present invention.

Suitably, the variant lipid acyltransferase according to the present invention retains at least 70%, preferably at least 80%, preferably at least 90%, preferably at least 95%, preferably at least 97%, preferably at least 99% homology with the parent enzyme.

Suitably, the variant lipid acyltransferase enzyme may comprise the amino acid sequence motif GDSX (SEQ ID NO: 48), wherein X is one or more of the following amino acid residues L, A, V, I, F, Y, H, Q, T, N, M or S. Preferably, X of the GDSX (SEQ ID NO: 48) motif is L.

For the avoidance of doubt, when an amino acid is substituted in the parent enzyme it is preferably substituted with an amino acid which is different from that originally found at that position in the parent enzyme thus to produce a variant enzyme. In other words, the term "substitution" is not intended to cover the replacement of an amino acid with the same amino acid.

In one embodiment of the method of the present invention, however, substitution of one or more amino acid residues at a position other than position 31, may cover the replacement of an amino acid with the same amino acid provided that this results in a change of codon at the nucleotide sequence level.

WO 2005/066347 discloses particular positions of a lipid acyltransferase that can be modified to enhance the ratio of transferase activity from galactolipids compared with phospholipids. Hence, the variant lipid acyltransferase of the present application may in addition to the modifications taught herein comprise one or more further modifications as disclosed in WO 2005/066347 (which is incorporated herein by reference).

In a preferable embodiment a variant lipid acyltransferase enzyme retains or incorporates at least one or more of the pfam00657 consensus sequence amino acid residues found in the GDSx (SEQ ID NO: 48), GANDY (SEQ ID NO: 49) and HPT blocks.

Enzymes, such as lipases with no or low lipid acyltransferase activity in an aqueous environment may be mutated using molecular evolution tools to introduce or enhance the transferase activity, thereby producing a variant lipid acyltransferase enzyme with significant transferase activity suitable for use in the compositions and methods of the present invention.

The variant lipid acyltransferase according to the present invention and produced by the methods of the present invention has at least one improved property compared with a parent (i.e. backbone) or unmodified lipid acyltransferase.

The term "improved property" as used herein may include a) an altered substrate specificity of the lipid acyltransferase, for instance and by way of example only i) an altered ability of the enzymes to use certain compounds as acceptors, for example an improved ability to utilise a carbohydrate (e.g. maltose) as an acceptor molecule thus improving the enzymes ability to produce a carbohydrate ester) or ii) an altering ability to use saturated or unsaturated fatty acids as a substrate or iii) a changed specificity such that the variant lipid acyltransferase preferentially utilises the fatty acid from the Sn1 or Sn2 position of a lipid substrate or iv) an altered substrate chain length specificity of in the variant enzyme; b) altered kinetics of the enzyme; and/or c) lowered ability of the variant lipid acyltransferase to carry out a hydrolysis reaction whilst maintaining or enhancing the enzymes ability to carry out an acyl transferase reaction.

Other improved properties may be for example related to improvements and/or changes in pH and/or temperature stability, and/or detergent and/or oxidative stability. Indeed, it is contemplated that enzymes having various degrees of stability in one or more of these characteristics (pH, temperature, proteolytic stability, detergent stability, and/or oxidative stability) can be prepared in accordance with the present invention.

Characterization of wild-type (e.g. parent lipid acyltransferase) and mutant (e.g. variant lipid acyltransferase) proteins is accomplished via any means suitable and is preferably based on the assessment of properties of interest.

Suitably, the variant lipid acyltransferase may have a carbohydrate (e.g. maltose) transferase activity of at least 0.02%, 0.03%, 0.04%, 0.05%, 0.06%, 0.07%, 0.08%, 0.1%, 0.15%, 0.2%, 0.25%, 0.3%, 0.35% or 0.4%, when using the assay provided in Protocol 1 detailed hereinbelow.

Suitably, the variant lipid acyltransferase may have a carbohydrate (e.g. maltose) transferase activity of at least 0.0059% when using the assay provided in protocol 2 detailed hereinbelow. Suitably, the variant lipid acyltransferase may have a maltose transferase activity of at least 0.009, 0.01, 0.02, 0.03, 0.035, 0.04, 0.045, 0.05, 0.055 or 0.06% when using the assay provided in Protocol 2.

Preferably the variant lipid acyltransferase may have a carbohydrate (e.g. maltose) transferase activity of at least 0.0282%+10-20%.

Suitably, the methods according to the present invention may comprise the steps of testing the variant lipid acyltransferase for one or more of the improved properties and/or selecting a variant enzyme, which when compared with the parent enzyme, which has the improved property.

By way of example only the methods according to the present invention may comprise the steps of measuring the ability of the variant lipid acyltransferase to transfer an acyl group to a carbohydrate (e.g. maltose and/or glucose) compared with the parent lipid acyltransferase; and selecting a variant lipid acyltransferase having an improved ability to transfer an acyl group to maltose as compared with the parent lipid acyltransferase.

In some embodiments the variant enzyme of the present invention, when compared with the parent enzyme, may have an increased transferase activity and either the same or less hydrolytic activity. In other words, suitably the variant enzyme may have a higher transferase activity to hydrolytic activity (e.g. transferase:hydrolysis activity) compared with the parent enzyme. Suitably, the variant enzyme may preferentially transfer an acyl group from a lipid (including phospholipid, galactolipid or triacylglycerol) to an acyl acceptor rather than simply hydrolysing the lipid.

Suitably, the lipid acyltransferase according to the present invention and for use in the invention may be a variant with enhanced enzyme activity on polar lipids, preferably phospholipids and/or glycolipids, when compared to the parent enzyme. Preferably, such variants also have low or no activity on lyso-polar lipids. The enhanced activity on polar lipids, preferably phospholipids and/or glycolipids, may be the result of hydrolysis and/or transferase activity or a combination of both. Preferably the enhanced activity on polar lipids in the result of transferase activity.

Variant lipid acyltransferases according to the present invention and for use in the invention may have decreased activity on triglycerides, and/or monoglycerides and/or diglycerides compared with the parent enzyme.

Suitably the variant enzyme may have no activity on triglycerides and/or monoglycerides and/or diglycerides. Low activity on triglycerides is preferred in variant enzymes which are to be used for bakery applications, for treatment of egg or egg-based products and/or for degumming oils.

Accordingly, the variant lipid acyltransferase of the present invention or composition comprising said variant lipid acyltransferase of the present invention may be used in combination with other components.

Examples of other components include one or more of: thickeners, gelling agents, emulsifiers, binders, crystal modifiers, sweeteners (including artificial sweeteners), rheology modifiers, stabilizers, anti-oxidants, dyes, enzymes, carriers, vehicles, excipients, diluents, lubricating agents, flavoring agents, colouring matter, suspending agents, disintegrants, granulation binders etc. These other components may be natural. These other components may be prepared by use of chemical and/or enzymatic techniques.

As used herein the term "thickener or gelling agent" as used herein refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilizing them.

The term "stabilizer" as used here is defined as an ingredient or combination of ingredients that keeps a product (e.g. a food product) from changing over time.

The term "emulsifier" as used herein refers to an ingredient (e.g. a food product ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilized through the use of emulsifiers. Aeration can occur in a three phase system where air is entrapped by liquid oil then stabilized by agglomerated fat crystals stabilized with an emulsifier. Emulsifiers have a polar group with an affinity for water (hydrophilic) and a non-polar group which is attracted to oil (lipophilic). They are absorbed at the interfaces of the two substances, providing an interfacial film acting to stabilize the emulsion. The hydrophilic/lipophilic properties of emulsifiers are affected by the structure of the molecule. These properties are identified by the hydrophilic/lipophilic balance (HLB) value. Low HLB values indicate greater lipophilic tendencies which are used to stabilize water-in-oil emulsions. High HLB values are assigned to hydrophilic emulsifiers, typically used in oil-in-water emulsions. These values are derived from simple systems. Because foods often contain other ingredients that affect the emulsification properties, the HLB values may not always be a reliable guide for emulsifier selection.

As used herein the term "binder" refers to an ingredient (e.g. a food ingredient) that binds the product together through a physical or chemical reaction. During "elation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

The term "crystal modifier" as used herein refers to an ingredient (e.g. a food ingredient) that affects the crystallisation of either fat or water. Stabilisation of ice crystals is important for two reasons. The first is directly related to the product stability from a separation standpoint. The more freeze/thaw cycles a product encounters, the larger the ice crystals become. These large crystals can break down product structure, either naturally occurring, as in the case of cell walls, or that which is created by "elation". Because the water is no longer held in place, the product may exhibit syneresis, or weeping, after thawing. Secondly, in the case of a product which is consumed frozen, these large crystals result in an undesirable, gritty mouth feel.

"Carriers" or "vehicles" mean materials suitable for compound administration and include any such material known in the art such as, for example, any liquid, gel, solvent, liquid diluent, solubilizer, or the like, which is non-toxic and which does not interact with any components of the composition in a deleterious manner.

Examples of nutritionally acceptable carriers include, but are not limited to, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Examples of excipients include, but are not limited to, one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include, but are not limited to, one or more of: starch (preferably corn, potato or tapioca starch), sodium starch glycollate, croscarmellose sodium and certain complex silicates.

Examples of granulation binders include, but are not limited to, one or more of: polyvinylpyrrolidone, hydroxypropylmethylcellulose (HPMC), hydroxypropylcellulose (HPC), sucrose, maltose, gelatin and acacia.

Examples of lubricating agents include, but are not limited to, one or more of: magnesium stearate, stearic acid, glyceryl behenate and talc.

Examples of diluents include, but are not limited to, one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

As used herein the term "component suitable for animal or human consumption" means a compound which is or can be added to the composition of the present invention as a supplement which may be of nutritional benefit, a fiber substitute or have a generally beneficial effect to the consumer. The ingredients can be used in a wide variety of products that require gelling, texturizing, stabilizing, suspending, film-forming and structuring, retention of juiciness, without adding unnecessary viscosity. Preferably, the ingredients will be able to improve the shelf live and stability of the viable culture.

By way of example, the components may include, but are not limited to, prebiotics such as alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

In one embodiment the variant lipid acyltransferase according to the present invention may be used in combination with the fungal lipolytic enzyme taught in WO2005/087918 (the teachings of which are incorporated herein by reference). This may be a particularly useful combination for use in baking.

In addition the variant lipid acyltransferases according to the present invention in some applications may be used in combination with one or more other enzymes, such as lipases, phospholipases, cellulases, hemicellulases, xylanases, starch degrading enzymes (including amylases, particularly maltogenic amylases), oxidoreductases and proteases.

When the lipid acyltransferase of the present invention is used in degumming applications it may be used in combination with a phospholipase A enzyme and/or a phospholipase C enzyme.

Suitably, the acyltransferase activity accounts for at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following protocol:

A foodstuff to which a lipid acyltransferase according to the present invention has been added may be extracted following the enzymatic reaction with $CHCl_3:CH_3OH$ 2:1 and the organic phase containing the lipid material is isolated and analysed by GLC according to the procedure detailed hereinbelow. From the GLC analysis (and if necessary HPLC analysis) the amount of free fatty acids and one or more of sterol/stanol esters; carbohydrate esters, protein esters; diglycerides; or monoglycerides are determined. A control foodstuff to which no enzyme according to the present invention has been added, is analysed in the same way.

From the results of the GLC (and optionally HPLC analyses) the increase in free fatty acids and sterol/stanol esters and/or carbohydrate esters and/or protein esters and/or diglycerides and/or monoglycerides can be calculated:

$\Delta$% fatty acid=% Fatty acid(enzyme)−% fatty acid(control); Mv fatty acid=average molecular weight of the fatty acids;

A=$\Delta$% sterol ester/Mv sterol ester (where $\Delta$% sterol ester=% sterol/stanol ester(enzyme)−% sterol/stanol ester(control) and Mv sterol ester=average molecular weight of the sterol/stanol esters)−applicable where the acyl acceptor is a sterol and/or stanol;

B=$\Delta$% carbohydrate ester/Mv carbohydrate ester (where $\Delta$% carbohydrate ester=% carbohydrate ester(enzyme)−% carbohydrate ester(control) and Mv carbohydrate ester=average molecular weight of the carbohydrate ester)−applicable where the acyl acceptor is a carbohydrate;

C=$\Delta$% protein ester/Mv protein ester (where $\Delta$% protein ester=% protein ester(enzyme)−% protein ester(control) and Mv protein ester=average molecular weight of the protein ester)−applicable where the acyl acceptor is a protein; and D=absolute value of diglyceride and/or monoglyceride/Mv di/monoglyceride (where $\Delta$% diglyceride and/or monoglyceride=% diglyceride and/or monoglyceride (enzyme)−% diglyceride and/or monoglyceride (control) and Mv di/monoglyceride=average molecular weight of the diglyceride and/or monoglyceride)−applicable where the acyl acceptor is glycerol.

The transferase activity is calculated as a percentage of the total enzymatic activity:

$$\% \text{ transferase activity} = \frac{A^* + B^* + C^* + D^* \times 100}{A^* + B^* + C^* + D^* + \Delta \% \text{ fatty acid}/(Mv \text{ fatty acid})}*$$

−delete as appropriate.

GLC Analysis

Perkin Elmer Autosystem 9000 Capillary Gas Chromatograph equipped with WCOT fused silica column 12.5 m×0.25 mm ID×0.1µ film thickness 5% phenyl-methyl-silicone (CP Sil 8 CB from Chrompack).

Carrier gas: Helium.

Injector. PSSI cold split injection (initial temp 50° C. heated to 385° C.), volume 1.00

Detector FID: 395° C.

Oven program:

|  | 1 | 2 | 3 |
| --- | --- | --- | --- |
| Oven temperature, °C. | 90 | 280 | 350 |
| Isothermal, time, min. | 1 | 0 | 10 |
| Temperature rate, °C./min. |  | 15 | 4 |

Sample preparation: 30 mg of sample was dissolved in 9 ml Heptane:Pyridin, 2:1 containing internal standard heptadecane, 0.5 mg/ml. 300 μl sample solution was transferred to a crimp vial, 300 μl MSTFA (N-Methyl-N-trimethylsilyl-trifluoraceamid) was added and reacted for 20 minutes at 60° C.

Calculation: Response factors for mono-di-triglycerides and free fatty acid were determined from Standard 2 (mono-di-triglyceride), for Cholesterol, Cholesteryl palmitate and Cholesteryl stearate the response factors were determined from pure reference material (weighing for pure material 10 mg).

A variety of assays may be employed to evaluate the substrate specificity of a variant lipid acyltransferase. In certain embodiments, an assay may contain the following components: a test acyl substrate (e.g., an acyl ester) having a carbon chain of a particular length, a recipient molecule, e.g., a carbohydrate, sterol/stanol or an alcohol, and a lipid acyltransferase enzyme, where the assay detects transfer of an acyl group from the acyl substrate to a recipient molecule in an aqueous environment.

In certain cases, a library of variant lipid acyltransferases may be made, and the members of the library tested for altered substrate specificity. Altered lipid acyltransferases having altered substrate specificity may be identified using such methods.

Protocol 1—Determination of Maltose Transferase Activity (20 h Protocol)

14 g egg yolk and 7 g carbohydrate monohydrate (e.g. maltose monohydrate, glucose monohydrate, lactose monohydrate and/or galactose monohydrate) 99% is stirred for 30 min. 1 g egg yolk/carbohydrate substrate (e.g. maltose substrate, glucose substrate, lactose substrate and/or galactose substrate) is then stirred with 100 μl enzyme solution (or control solution) for 20 hours at 40° C. 7.5 ml CHCl$_3$:MeOH 2;1 is added and mixed for 30 minutes before centrifuging at 1500 rpm (700 g) for 10 minutes. The organic phase is then transferred to a TLC vial. A TLC plate is activated by incubation at 160° C. for 10 minutes. 8 μl of each sample is then applied to a HPTLC Si-plate. As a standard, 0.1, 0.3, 0.5, 0.8 and 1.5 μl 0.1% carbohydrate-monooleate (e.g. maltose-monooleate, glucose-monooleate, lactose-monooleate, and/or galactose-monooleate) are applied. The TLC-plate is then eluted in solvent 4-1 (CHCl$_3$:Methanol:Water 64:26:4) for 20 minutes, before being dried in a fume cupboard for approximately 10 minutes and incubated at 160° C. for 10 minutes. The plate is then developed by submerging in 6% Cu-acetate in 16% H$_3$PO$_4$ for 10 seconds, then drying (with dry filter paper) and incubating at 160° C. for 8 minutes. The % carbohydrate transferase activity (e.g. maltose, glucose, lactose and/or galactose transferase activity) is defined as the % carbohydrate-ester (e.g. maltose-ester, glucose-ester, lactose-ester and/or galactose ester) determined using this protocol.

Protocol 2—Alternative Determination of Maltose Transferase Activity (1 h Protocol)

14 g egg yolk and 7 g carbohydrate monohydrate (e.g. maltose monohydrate, glucose monohydrate, lactose monohydrate and/or galactose monohydrate) 99% is stirred for 30 min. 1 g egg yolk/carbohydrate substrate (e.g. maltose substrate, glucose substrate, lactose substrate and/or galactose substrate) is then stirred with 100 μl enzyme solution (or control solution) for 1 hour at 40° C. 7.5 ml CHCl$_3$:MeOH 2;1 is added and mixed for 30 minutes before centrifuging at 1500 rpm (700 g) for 10 minutes. The organic phase is then transferred to a TLC vial. A TLC plate is activated by incubation at 160° C. for 10 minutes. 8 μl of each sample is then applied to a HPTLC Si-plate. As a standard, 0.1, 0.3, 0.5, 0.8 and 1.5 μl 0.1% carbohydrate-monooleate (e.g. maltose-monooleate, glucose-monooleate, lactose-monooleate, and/or galactose-monooleate) are applied. The TLC-plate is then eluted in solvent 4-1 (CHCl$_3$:Methanol:Water 64:26:4) for 20 minutes, before being dried in a fume cupboard for approximately 10 minutes and incubated at 160° C. for 10 minutes. The plate is then developed by submerging in 6% Cu-acetate in 16% H$_3$PO$_4$ for 10 seconds, then drying (with dry filter paper) and incubating at 160° C. for 8 minutes. The % carbohydrate transferase activity (e.g. maltose, glucose, lactose and/or galactose transferase activity) is defined as the % carbohydrate-ester (e.g. maltose-ester, glucose-ester, lactose-ester and/or galactose ester) determined using this protocol.

Compositions comprising an altered or variant lipid acyltransferase are also provided.

In certain embodiments the altered lipid acyltransferase comprises an amino acid sequence that is at least 70% identical with a wild-type lipid acyltransferase or a backbone lipid acyltransferase.

The composition may be a food product, e.g., an edible product for human or animal consumption, or an intermediate in the manufacture of an edible food product (e.g. a food supplement), or a cleaning and/or detergent composition, for example.

As noted above, a cleaning and/or detergent composition comprising a variant lipid acyltransferase enzyme is also encompassed within the present invention. In certain embodiments, the cleaning composition may comprise the following components: a) a subject variant lipid acyltransferase, as described herein, b) a long chain ester substrate which, in certain embodiments, may be of the formula R$_1$C(=O)OR$_2$, where R$_1$ comprises a substituted or unsubstituted carbon chain of at least 5 carbon atoms and R$_2$ is any organic moiety; and c) a source of hydrogen peroxide. A variety of other compounds may be present in a subject cleaning composition.

A subject cleaning composition may be employed for example, in laundry applications, hard surface cleaning, automatic dishwashing applications, as well as cosmetic applications such as dentures, teeth, hair and skin. However, due to their unique properties of increased effectiveness in lower temperature solutions and the superior colour-safety profile, the subject enzymes are ideally suited for laundry applications such as the bleaching of fabrics. Furthermore, the enzymes of the present invention find use in both granular and liquid compositions.

The subject enzyme also finds use in cleaning additive products. The subject cleaning additive products are ideally suited for inclusion in wash processes where additional bleaching effectiveness is desired. Such instances include, but are not limited to, low temperature solution cleaning applications. The additive product may be, in its simplest form, one or more of the enzymes of the present invention. Such additive may be packaged in dosage form for addition to a cleaning process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of such composition. Suitable filler or carrier materials include, but are not limited to, various salts of sulfate, carbonate and silicate as well as talc, clay and the like. Filler or carrier materials for liquid compositions may be water or low molecular weight primary and secondary alcohols including polyols and diols. Examples of such alcohols include, but are not limited to, methanol, ethanol, propanol and isopropanol. The compositions may contain from about 5% to about 90% of such materials. Acidic fillers can be used to reduce pH. Alternatively, the cleaning additive may include activated peroxygen source such as esters of alcohols, esters of diols, or esters of polyols or as defined below or the adjunct ingredients as also defined below.

The cleaning compositions and cleaning additives of the present invention require an effective amount of the enzyme provided by the present invention. Typically a cleaning composition of the present invention comprise at least 0.0001 weight percent, from about 0.0001 to about 1, from about 0.001 to about 0.5, or even from about 0.01 to about 0.1 weight percent of at least one enzyme of the present invention.

As used herein, "cleaning compositions" and "cleaning formulations" refer to compositions that find use in the removal of undesired compounds from items to be cleaned, including, but not limited to, fabric, dishes, contact lenses, other solid substrates, hair (shampoos), skin (soaps and creams), teeth (mouthwashes, toothpastes), etc. The term encompasses any materials/compounds selected for the particular type of cleaning composition desired and the form of the product (e.g., liquid, gel, granule, or spray composition), as long as the composition is compatible with the perhydrolase and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some preferred embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that in addition to perhydrolase, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein the term "hard surface cleaning composition," refers to detergent compositions for cleaning hard surfaces, including, but not limited to, floors, walls, tile, bath and kitchen fixtures, and the like. Such compositions are provided in any form, including but not limited to solids, liquids, emulsions, etc.

As used herein, "dishwashing composition" refers to all forms for compositions for cleaning dishes, including but not limited to granular and liquid forms.

As used herein, "fabric cleaning composition" refers to all forms of detergent compositions for cleaning fabrics, including but not limited to, granular, liquid and bar forms.

As used herein, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, "textile materials" is a general term for fibers, yarn intermediates, yarn, fabrics, and products made from fabrics (e.g., garments and other articles).

As used herein, "fabric" encompasses any textile material. Thus, it is intended that the term encompass garments, as well as fabrics, yarns, fibers, non-woven materials, natural materials, synthetic materials, and any other textile material.

As used herein, the term "compatible," means that the cleaning composition materials do not reduce the enzymatic activity of the perhydrolase to such an extent that the perhydrolase is not effective as desired during normal use situations. Specific cleaning composition materials are exemplified in detail hereinafter.

The above-described composition may be employed in a variety of methods or uses. In general terms, the method or use may include contacting a subject altered lipid acyltransferase with a substrate under conditions suitable for the lipid acyltransferase to transfer an acyl group from said substrate onto an acceptor molecule. The contacting may be done in aqueous conditions.

The methods may be employed in food manufacture, cleaning products, biocatalysis (e.g., to produce esters, which can act as emulsifying agents and/or surfactants, etc.) and a variety of other applications. Esters produced when the variant enzymes are used as biocatalysts can be used in cosmetics, in foodstuffs (including in baked products, in meat products, in egg based products and in dairy products), in pharmaceuticals, in soap, in candles, in oils, in lubricants, in varnishes, in linoleum, in inks, in prints, in textile dyes, and in or as surfactants.

Further uses for the above-described enzyme are described in, for example, the following published patent applications: US20070026106, US20060078648, US20050196766 and WO2005066347, which patent applications are incorporated by reference for disclosure of those uses.

In addition to the above-described applications, the above-described enzyme may be employed in a variety of food applications. For example, the enzyme may be present in, or may be used to make, a foodstuff, where a foodstuff is any substance which is suitable for human and/or animal consumption. By way of example, the term foodstuff encompasses both baked goods produced from dough as well as the dough used in the preparation of said baked goods. In certain cases, a foodstuff may be a water-containing foodstuff. An exemplary water-containing foodstuff comprise 10-98% water, e.g. 14-98%, 18-98%, 20-98%, 40-98%, 50-98%, 70-98%, 75-98% water, excluding solid components.

In certain embodiments, a foodstuff may be selected from one or more of the following: eggs, egg-based products, including but not limited to mayonnaise, salad dressings, sauces, ice creams, egg powder, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, cream, butter, milk, coffee cream, whipped cream, custard cream, milk drinks and yoghurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces. So-called "fine foods", including cakes, pastry, confectionery, chocolates, fudge and the like, are also types of foodstuff.

In one embodiment the foodstuff in accordance with the present invention may be a dough product or a baked product, such as a bread, a fried product, a snack, cakes, pies, brownies, cookies, noodles, snack items such as crackers, graham crackers, pretzels, and potato chips, and pasta. In other embodiments, a foodstuff may be a flour, pre-mix, oil, fat, cocoa butter, coffee whitener, salad dressing, margarine, spread, peanut butter, shortenings, ice cream or cooking oil.

In another aspect, the foodstuff in accordance with the present invention may be a dairy product, including butter, milk, cream, cheese such as natural, processed, and imitation cheeses in a variety of forms (including shredded, block, slices or grated), cream cheese, ice cream, frozen desserts, yoghurt, yoghurt drinks, butter fat, anhydrous milk fat, other dairy products. The enzyme according to the present invention may improve fat stability in dairy products.

In particular embodiments a method of preparing a foodstuff is provided. This method generally comprises adding an above-described enzyme to the foodstuff or an ingredient thereof.

In other embodiments, a foodstuff comprising a variant enzyme is provided. For example, enzyme may be employed in the following methods: in situ production of an emulsifier without an increase in free fatty acids; a reduction in the accumulation of free fatty acids in the foodstuff; a reduction in free cholesterol levels in the foodstuff; an increase in sterol esters and/or stanol esters; a reduction in blood serum cholesterol and/or low density lipoproteins; an increase in carbohydrate esters; a reduction in unwanted free carbohydrates.

In one example, the acyl acceptor molecule in the foodstuff may be any compound containing a hydroxy group (—OH), such as for example, polyvalent alcohols, including glycerol; sterol; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolyzed protein) for example; and mixtures and derivatives thereof. In certain cases, the acyl acceptor is not water.

A sterol and/or stanol may comprise one or more of the following structural features: i) a 3-beta hydroxy group or a 3-alpha hydroxy group; and/or ii) A:B rings in the cis position or A:B rings in the trans position or $C_5$-$C_6$ is unsaturated. Suitable sterol acyl acceptors include, but are not limited to, cholesterol and phytosterols, for example alpha-sitosterol, beta-sitosterol, stigmasterol, ergosterol, campesterol, 5,6-dihydrosterol, bras sicasterol, alpha-spinasterol, beta-spinasterol, gamma-spinasterol, deltaspinasterol, fucosterol, dimosterol, ascosterol, serebisterol, episterol, anasterol, hyposterol, chondrillasterol, desmosterol, chalinosterol, poriferasterol, clionasterol, sterol glycosides, and other natural or synthetic isomeric forms and derivatives.

In one aspect of the present invention suitably more than one sterol and/or stanol may act as the acyl acceptor, suitably more than two sterols and/or stanols may act as the acyl acceptor. In other words, in one aspect of the present invention, suitably more than one sterol ester and/or stanol ester may be produced. Suitably, when cholesterol is the acyl acceptor one or more further sterols or one or more stanols may also act as the acyl acceptor. Thus, in one aspect, the present invention provides a method for the in situ production of both a cholesterol ester and at least one sterol or stanol ester in combination. In other words, the lipid acyltransferase for some aspects of the present invention may transfer an acyl group from a lipid to both cholesterol and at least one further sterol and/or at least one stanol.

In one embodiment, the sterol acyl acceptor may be cholesterol. In these embodiments, the amount of free cholesterol in the foodstuff may be reduced as compared with the foodstuff prior to exposure to the enzyme and/or as compared with an equivalent foodstuff which has not been treated with the enzyme.

In other embodiment, a subject enzyme may be used in the production of an egg-based product. As such, a method that includes contacting a subject enzyme with an egg or egg-based product is provided. An egg-based product comprising a subject enzyme is also provided.

In particular, the presence of sugars, in particular glucose, in eggs and egg products is often seen as disadvantageous. Egg yolk may comprise up to 1% glucose and, egg or egg based products may be treated with glucose oxidase to remove some or all of this glucose. However, in accordance with certain aspects of the present invention this unwanted sugar can be readily removed by "esterifying" the sugar to form a sugar ester.

In particular cases, a carbohydrate ester can function as an emulsifier in foodstuffs. Thus, in certain cases, the enzyme can be employed to transfer an acyl group to a sugar, the invention encompasses the production of an emulsifier, in situ, in the foodstuff. In these cases, a subject enzyme may utilize a sterol and/or stanol and a carbohydrate as an acyl acceptor, which method is particularly useful for the production of foodstuffs containing eggs or egg products. In other embodiments the ester produced (e.g., stanol ester or the sterol ester) may be a flavoring and/or texturiser agent.

In another embodiment, a subject enzyme may be added to dough, for example, as part of a baking method. The method may also include baking dough containing the enzyme to make a baked product from the dough. When used in preparation of a dough or baked product a subject enzyme may result in one or more of the following technical effects in dough and/or baked products: an improved specific volume of either the dough or the baked products (for example of bread and/or of cake); an improved dough stability; an improved crust score (for example a thinner and/or crispier bread crust), an improved crumb score (for example a more homogenous crumb distribution and/or a finer crumb structure and/or a softer crumb); an improved appearance (for example a smooth surface without blisters or holes or substantially without blisters or holes); a reduced staling; an enhanced softness; an improved odour; an improved taste.

Flour used in dough and baked products typically contains about 2% maltose. Maltose unlike other sugars is not used by yeast. Therefore in one embodiment of the present invention it may be pertinent to increase the maltose utilization of the enzyme, i.e. to increase the ability of the enzyme to transfer an acyl group from a lipid to maltose to form a maltose ester. This can be particularly important and lead to substantial advantages in baked products, such as a bread, a fried product, a snack, cakes, pies, brownies, cookies, noodles, snack items such as crackers, graham crackers, pretzels, and potato chips, and pasta. By use of variant lipid acyltransferases of the present invention it is possible to replace the commonly used emulsifier "DATEM™" in baked products. Preferably at least 0.1% of carbohydrate ester, e.g. maltose ester, is produced in the baked product (or the dough thereof) by using the variant lipid acyltransferase of the present invention.

In other embodiments, a subject enzyme may be employed to degum (i.e., reduce the amount of polar lipid, e.g., phospholipids and/or glycolipid such as lecithin, i.e., phosphatidylcholine and cephalin) in vegetable or edible oils. In these embodiments, a subject variant lipid acyltransferase may be contacted with the oil so as to hydrolyze a polar lipid(s) in the oil.

In particular embodiments a variant lipid acyltransferase in accordance with the present invention may be employed to reduce phospholipid in an edible oil, comprising treating the oil with a subject enzyme so as to hydrolyze a major part of the phospholipid, and separating an aqueous phase containing the hydrolyzed phospholipid from the oil.

In other embodiments, a subject enzyme may be employed to convert polar lipids (e.g. glycolipids and/or phospholipids) into a higher value product, such as carbohydrate esters, protein esters (e.g., via reaction with a serine, threonine, tyrosine, or cysteine residue), and a hydroxy acid ester. Thus, a subject enzyme may be employed to transfer any acyl chain onto a sterol, a stanol, a carbohydrate, a protein, or glycerol, for example.

In certain embodiments, an emulsifier may be prepared in situ in the foodstuff without an increase in the free fatty acid content of the foodstuff. In certain cases, the production of free fatty acids can be detrimental to foodstuffs. In particular, free fatty acids have been linked with off-odours and/or off-flavors in foodstuffs, as well other detrimental effects, including a soapy taste in cheese for instance. In certain case, this method results in the in situ preparation of an emulsifier(s) (preferably two emulsifiers) wherein the accumulation of free fatty acids is reduced and/or eliminated. In cases, the fatty acid that is removed from the lipid is transferred by the enzyme to an acyl acceptor, for example a sterol and/or a stanol. Thus, unlike similar methods that might employ other lipases (e.g., those having an activity defined by E.C. 3.1.1.x such as a lipase (E.C. 3.1.1.3) or a phospholipase A enzyme [E.C. 3.1.1.32 or 3.1.1.4]), the instant method may result in no significant increase in the level of free fatty acids in the foodstuff. Such methods may be particularly employed on foodstuffs containing eggs.

For some aspects of the present invention, the variant lipid acyltransferase according to the present invention may utilize a protein as the acyl acceptor. Suitably, the protein may be one or more of the proteins found in a food product, for example in a dairy product and/or a meat product. By way of example only, suitable proteins may be those found in curd or whey, such as lactoglobulin. Other suitable proteins include ovalbumin from egg, gliadin, glutenin, puroindoline, lipid transfer proteins from grains, and myosin from meat.

In addition to its applications in detergents, the present invention provides methods and compositions for the use of peracids in textile bleaching and in various other applications. In some embodiments, the present invention provides one-step methods for textile processing applications, including but not limited to one-step desizing, scouring and bleaching processes (See e.g., EP WO 03002810, EP 1255888, WO 0164993, and US 20020007516, all of which are hereby incorporated by reference). As described in greater detail herein, in some embodiments, bleaching involves processing textile material before it is dyed and/or after it is incorporated into textile goods. However, it is not intended that the present invention be limited to any particular regimen of use nor any particular textile material.

Suitably the lipid acyltransferase in accordance with the present invention may be encoded by any one of the nucleotide sequences taught herein.

Depending upon the host cell used post-transcriptional and/or post-translational modifications may be made. It is envisaged that the lipid acyltransferase for use in the present methods and/or uses encompasses lipid acyltransferases which have undergone post-transcriptional and/or post-translational modification.

By way of example only, the expression of the nucleotide sequence shown herein as SEQ ID No. 10 (see FIG. 22) or SEQ ID No. 25 (see FIG. 42) in a host cell (such as Bacillus licheniformis for example) results in post-transcriptional and/or post-translational modifications which leads to the amino acid sequence shown herein as SEQ ID No. 16.

SEQ ID No. 16 is the same as SEQ ID No. 6 except that SEQ ID No. 16 has undergone post-translational and/or post-transcriptional modification to remove some amino acids, more specifically 38 amino acids. Notably the N-terminal and C-terminal part of the molecule are covalently linked by an S—S bridge between two cysteines. Amino residues 236 and 236 of SEQ ID No. 16 are not covalently linked following post-translational modification. The two peptides formed are held together by one or more S—S bridges.

The precise cleavage site(s) in respect of the post-translational and/or post-transcriptional modification may vary slightly such that by way of example only the 38 amino acids removed (as shown in SEQ ID No. 16 compared with SEQ ID No. 6) may vary slightly. Without wishing to be bound by theory, the cleavage site may be shifted by a few residues (e.g. 1, 2 or 3 residues) in either direction compared with the cleavage site shown by reference to SEQ ID No. 16 compared with SEQ ID No. 6. In other words, rather than cleavage at position 235-ATR to position 273 (RRSAS) (SEQ ID NO: 47) for example, the cleavage may commence at residue 232, 233, 234, 235, 236, 237 or 238 for example. In addition or alternatively, the cleavage may result in the removal of about 38 amino acids, in some embodiments the cleavage may result in the removal of between 30-45 residues, such as 34-42 residues, such as 36-40 residues, preferably 38 residues.

In one aspect, the lipid acyltransferase is a recovered/isolated lipid acyltransferase. Thus, the parent or variant lipid acyltransferase produced may be in an isolated form.

In another aspect, the nucleotide sequence encoding a parent or variant lipid acyltransferase for use in the present invention may be in an isolated form.

The term "isolated" means that the sequence or protein is at least substantially free from at least one other component with which the sequence or protein is naturally associated in nature and as found in nature.

In one aspect, the lipid acyltransferase may be in a purified form.

In another aspect, the nucleotide sequence encoding a lipid acyltransferase for use in the present invention may be in a purified form.

The term "purified" means that the sequence is in a relatively pure state—e.g. at least about 51% pure, or at least about 75%, or at least about 80%, or at least about 90% pure, or at least about 95% pure or at least about 98% pure.

A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labelled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984)2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, in addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate As will be apparent to a person skilled in the art, using molecular evolution tools an enzyme may be altered to improve the functionality of the enzyme.

Suitably, the nucleotide sequence encoding a lipid acyltransferase used in the invention may encode a variant lipid acyltransferase, i.e. the lipid acyltransferase may contain at least one amino acid substitution, deletion or addition, when compared to a parental enzyme. Preferably, the variant enzymes retain at least 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

The present invention also encompasses the use of amino acid sequences encoded by a nucleotide sequence which encodes a lipid acyltransferase for use in any one of the methods and/or uses of the present invention.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 μg of the freeze-dried material may be dissolved in 50 μl of a mixture of 8 M urea and 0.4 M ammonium hydrogen carbonate, pH 8.4. The dissolved protein may be denatured and reduced for 15 minutes at 50° C. following overlay with nitrogen and addition of 5 μl of 45 mM dithiothreitol. After cooling to room temperature, 5 μl of 100 mM iodoacetamide may be added for the cysteine residues to be derivatized for 15 minutes at room temperature in the dark under nitrogen.

135 μl of water and 5 μg of endoproteinase Lys-C in 5 μl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 μm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of other software that can perform sequence comparisons include, but are not limited to, the BLAST package (see Ausubel et al 1999 Short Protocols in Molecular Biology, 4$^{th}$ Ed—Chapter 18), and FASTA (Altschul et al 1990 J. Mol. Biol. 403-410). Both BLAST and FASTA are available for offline and online searching (see Ausubel et al 1999, pages 7-58 to 7-60). However, for some applications, it is preferred to use the Vector NTI program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and the website of the National Center for Biotechnology Information, National Library of Medicine, National Institutes of Health).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
|---|---|
| GAP OPEN | 0 |
| GAP EXTENSION | 0 |

| FOR CLUSTAL | | | |
|---|---|---|---|
| | DNA | PROTEIN | |
| WORD SIZE | 2 | 1 | K triple |
| GAP PENALTY | 15 | 10 | |
| GAP EXTENSION | 6.66 | 0.1 | |

In one embodiment, preferably the sequence identity for the nucleotide sequences is determined using CLUSTAL with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

In one embodiment the degree of amino acid sequence identity in accordance with the present invention may be suitably determined by means of computer programs known in the art, such as Vector NTI 10 (Invitrogen Corp.). For pairwise alignment the matrix used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

The present invention also encompasses the use of sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses the use of sequences that are complementary to sequences that are capable of hybridising under high stringency conditions or intermediate stringency conditions to nucleotide sequences encoding polypeptides having the specific properties as defined herein.

More preferably, the present invention encompasses the use of sequences that are complementary to sequences that are capable of hybridising under high stringency conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to the use of nucleotide sequences that can hybridize to the nucleotide sequences discussed herein (including complementary sequences of those discussed herein).

The present invention also relates to the use of nucleotide sequences that are complementary to sequences that can hybridize to the nucleotide sequences discussed herein (including complementary sequences of those discussed herein).

Also included within the scope of the present invention are the use of polynucleotide sequences that are capable of hybridising to the nucleotide sequences discussed herein under conditions of intermediate to maximal stringency.

In a preferred aspect, the present invention covers the use of nucleotide sequences that can hybridize to the nucleotide sequences discussed herein, or the complement thereof, under stringent conditions (e.g. 50° C. and 0.2×SSC).

In a more preferred aspect, the present invention covers the use of nucleotide sequences that can hybridize to the nucleotide sequences discussed herein, or the complement thereof, under high stringency conditions (e.g. 65° C. and 0.1×SSC).

For the production of libraries of variants microbial eukaryotic or prokaryotic expression hosts may be used. In order to ensure uniform expression within a library of variants, low copy number, preferably single event chromosomal expression systems may be preferred. Expression systems with high transformation frequencies are also preferred, particularly for the expression of large variant libraries (>1000 colonies), such as those prepared using random mutagenesis and/or shuffling technologies.

Suitable methods for the use of a eukaryotic expression host, namely yeast, in the production of enzymes are described in EP1131416. Microbial eukaryotic expression hosts, such as yeast, may be preferred for the expression of variant libraries produced using a eukaryotic acyltransferase parent gene.

Suitable methods using Bacillus, i.e. Bacillus subtilis, as an expression host in the production of enzymes are described in WO02/14490. Microbial prokaryotic expression hosts, such as Bacillus, may be preferred for the expression of variant libraries produced using a prokaryotic acyltransferase parent gene.

In one preferred embodiment the expression host is Bacillus licheniformis. Expression of lipid acyltransferases in Bacillus licheniformis is taught in WO2008/090395 (the teachings of which are incorporated herein by reference).

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

The term "organism" in relation to the present invention includes any organism that could comprise a nucleotide sequence according to the present invention or a nucleotide sequence encoding for a polypeptide having the specific properties as defined herein and/or products obtained therefrom.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a promoter not associated with a sequence encoding a lipid acyltransferase in nature.

The host organism can be a prokaryotic or a eukaryotic organism.

Examples of suitable prokaryotic hosts include bacteria such as *E. coli* and *Bacillus licheniformis*, preferably *B. licheniformis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of secretion leader sequences not associated with a nucleotide sequence encoding a lipid acyltransferase in nature are those originating from the fungal amyloglucosidase (AG) gene (glaA—both 18 and 24 amino acid versions e.g. from *Aspergillus*), the a-factor gene (yeasts e.g. *Saccharomyces*, *Kluyveromyces* and *Hansenula*) or the α-amylase gene (*Bacillus*).

The lipid acyltransferase for use in the present invention may be produced as a fusion protein, for example to aid in extraction and purification thereof. Examples of fusion protein partners include glutathione-S-transferase (GST), 6xHis (SEQ ID NO: 54), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

The amino acid sequence of a polypeptide having the specific properties as defined herein may be ligated to a non-native sequence to encode a fusion protein. For example, for screening of peptide libraries for agents capable of affecting the substance activity, it may be useful to encode a chimeric substance expressing a non-native epitope that is recognised by a commercially available antibody.

The invention will now be further described by way of the following non-limiting examples.

EXAMPLE 1

Generation of Variant Lipid Acyltransferases

Certain positions of a lipid acyltransferase comprising the sequence shown as SEQ ID No. 6 (*Aeromonas salmonicida* phosphatidylcholine cholesterol acyltransferase (=lipid acyltransferase)) were selected for site evaluation and screening for improved properties, such as an altered substrate specificity, e.g. an improved ability to generate certain esters (such as carbohydrate esters, e.g. maltose esters) or altered chain length specificity, or an improved transferase activity and/or a reduced hydrolysis activity.

The results shown herein demonstrate that modifying position one or more of positions 31, 27, 85, 86, 122, 119, 120, 201, 245, 232, 235 and 236 of SEQ ID No. 16 results in a lipid acyltransferase with improved properties compared with the backbone enzyme (i.e. a enzyme expressed from the nucleotide sequence SEQ ID No. 25), for example the lipid acyltransferase may have an altered substrate specificity, e.g. an improved ability to generate carbohydrate esters (e.g. a maltose-ester) and/or may have a reduced hydrolysis activity.

Sixty-six amino acid positions in and around the "cave and canyon" of the *Aeromonas salmonicida* lipid acyltransferase molecule (*Aeromonas salmonicida* phosphatidylcholine cholesterol acyltransferase) were selected for site evaluation and screening for improved transferase activity and the generation of maltose ester. The generation of 66 site evaluation libraries resulted in 1223 codon variants, with an average of 19 different codon variants and 14 different amino acid variants per library. Winner mutations identified by screening of the variants from the site evaluation libraries for formation of maltose ester were evaluated further in combination libraries. A total of more than 70 different combination variant clones with up to six mutations were isolated and characterized from the combination libraries.

Vector Construction

The vector used for the site evaluation libraries was pCS32new N80D, also named pLA52, containing the *Aeromonas salmonicida* GCAT gene with an Asn to Asp substitution at position 80 (the nucleotide sequence for this gene is provided herein as SEQ ID No. 25). The N80D mutation enhances the expression of the enzyme in *Bacillus subtilis*. The gene is under control of the p32 promoter and expressed with a *bacillus* Cyclodextrin glucanotransferase (CGTase) signal sequence. All variants were screened in the *Bacillus subtilis* expression host OS21DAprE.

Figure 29:
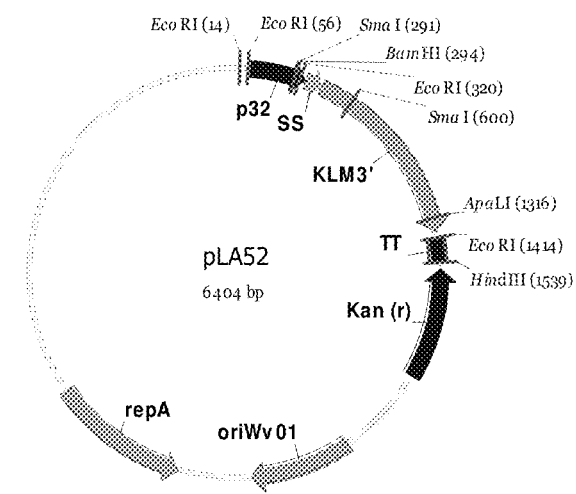
FIG. 29 shows the plasmid pLA52, containing the nucleotide sequence (SEQ ID No. 25) encoding lipid acyltransferase enzyme, used for generation of site evaluation libraries.

FIG. 29 shows the plasmid pLA52, containing the *Aeromonas salmonicida* GCAT gene with an Asn to Asp substitution at position 80 (the nucleotide sequence for this gene is provided herein as SEQ ID No. 25) lipid acyltransferase enzyme, used for generation of site evaluation libraries.

Site Evaluation Library Construction

Site evaluation libraries containing "all possible amino acids" at specific sites were generated by using a QuikChange Multi Site Directed Mutagenesis (MSDM) Kit (Stratagene) according to the manufacturer's protocol. Phosphorylated primers with degenerate codons (NNK or NNS) for random substitution of amino acids were used. The libraries were transformed into E. coli XL10-Gold Ultracompetent cells (Stratagene). Total library plasmid DNA was isolated from E. coli cultures and transformed into the Bacillus subtilis OS21DAprE expression host.

Combination Library Construction

Combination libraries were generated in the same way as site evaluation libraries except that up to four different primers containing specific mutations were used in the same MSDM reaction and the combination variants were identified by sequencing of E. coli colonies and subsequently transformed into Bacillus subtilis OS21DAprE.

Supplementation of Sites

Some site evaluation libraries that contained very few amino acid mutations were supplemented with the missing amino acids. These mutants were generated in the same way as site evaluation libraries except that specific primers for one or a few mutations were used in the MSDM reaction and the variants were identified by sequencing of E. coli colonies subsequently transformed into Bacillus subtilis OS21DAprE.

Transformation of Bacillus subtilis OS21DAprE

Library plasmid DNA, single mutant plasmid DNA or combination variant DNA were transformed into the Bacillus subtilis OS21DAprE comK strain, which has been made competent using xylose. Briefly, fresh colonies of the strain were cultured in LB at 37° C. until OD600 was about 1.0. Xylose was added to 0.3% and cultivation was continued for 2 hours. 5 µl of DNA (1 ug/ml) was added to 150 µl of competent cells, incubated in round bottom falcon tubes at 37° C. at 200 rpm for 1 hour and plated on LB agar with the recommended antibiotic (Kanamycin 25 µg/ml).

Selection of Variants

To identify the different amino acid variants in site evaluation libraries, the bacillus libraries were plated on LB plates and 96 colonies were picked at random from each library into 96-well plates. A replica of each 96-well plate was sent to AGOWA Gmbh, Berlin, Germany, for nucleic acid sequencing. The sequences of the 96 colonies were analysed at the mutated site and all available individual mutants representing each codon were selected for screening.

Selection of Combination Variants

To identify the different combination variants, 10-40 E. coli colonies, dependent on the number of primers used, were picked at random, and for sequencing colony PCR was used to amplify the gene. Each PCR reaction was sent to DNA Technology A/S, Aarhus, Denmark, for sequencing. The sequences were analysed at the mutated sites and all available variants representing the possible combination were selected. Each of the variants was transformed into the Bacillus subtilis expression host OS21DAprE for screening.

Analysis Protocol for Maltose-Ester Determination:

Application: This method was developed for analysis of maltose ester formation by transferase of fatty acids from lecithin to maltose.

Substrate: Pasteurized egg yolk
  Maltose monohydrate 99%
  Egg yolk with 33% maltose:
  Weigh 14 g egg yolk and 7 g maltose into a beaker and stir at 40° C. until the maltose is diluted (app. 30 min)
Enzymation: Weigh 1 g egg yolk/maltose substrate into a 12 mL glass vial with screw lid.

Add 100 µl enzyme solution (or corresponding control solution).
Place sample on a heater with magnetic stifling for 20 hrs at 40° C.
Extraction: After 1 and/or 20 hrs reaction, add 7.5 ml CHCl3:MeOH 2:1.
Mix sample 15 sec on a Whirley mixer.
Place on a Rotamix for 30 min.
Centrifuge the vial at 1500 rpm (700 g) for 10 min.
Transfer part of the organic phase to a TLC vial.
TLC: Activate the TLC-plate by incubation at 160° C. for 10 min
Sample application: Apply 8 µl of each sample to a HPTLC Si-plate. As a standard, 0.1-0.3-0.5-0.8 and 1.5 µl 0.1% maltose-monooleate are applied. Elute the TLC-plate in solvent 4-1 ($CHCl_3$:Methanol:Vand 64:26:4) for 20 min.
Dry the plate in a fume cupboard for app. 10 min, then incubate at 160° C. for 10 min.
Development with Cu— Submerge the plate in the development reagent for 10 sec, then dry acetate: (wipe with dry filter paper) and incubate at 160° for 8 min.
Reagents:
Running buffer: Nr. 4-1: Chloroform:Methanol:$H_2O$ (64:26:4)
Development reagent: 6% $Cu(Ac)_2$ in 16% $H_3PO_4$
  A 500 ml measuring flask is half filled with water. Add powder and acid, and adjust with water. Place on magnetic stirrer for 2-3 hours.

Most of the libraries were generated with pLA52 (the Aeromonas salmonicida lipid acyltransferase comprising the N80D variation and encoded by the nucleotide sequence SEQ ID No. 25) as backbone; however, 12 libraries were generated with L31Q, a combination clone, (L31Q, N80D), as backbone. Three libraries were generated with the combination clone M957 (L31Q, N80D, W122L), three libraries were generated with the combination clone M970 (L31Q, N80D, I86S), and one library was generated with the combination clone pLA487 (L31Q, N80D, I86S, W122L).

Table 1 shows the maltose transferase activity as % maltose-ester after 20 hours, for each of the mutant variant lipid acyltransferases (with single point mutations as taught herein). The backbone is the Aeromonas salmonicida lipid acyltransferase comprising the N80D variation and encoded by the nucleotide sequence SEQ ID No. 25 (sometimes referred to herein as the N80D backbone) produced in Bacillus licheniformis production strain.

| Fermentation No. AxxxP) | Mutation No. | Mutation | (N80D)—Backbone MALTOSE TRANSFERASE 33% Maltose 20 h Maltose-ester % |
|---|---|---|---|
| R7254P | M57 | I086R | 0.2808 |
| R7255P | M61 | I086Y | 0.2638 |
| A746P | M777 | M027R | 0.1945 |
| R7231P | M19 | M027G | 0.1843 |
| A740P | M772 | M027H | 0.1701 |
| R7233P | M776 | M027R | 0.1550 |
| A745P | M776 | M027R | 0.1527 |
| A039P | M39 | L031Q | 0.1430 |
| A737P | M17 | M027K | 0.1379 |
| R7234P | M777 | M027R | 0.1320 |
| A041P | M41 | L031H | 0.1264 |
| R7213P | M17 | M027K | 0.1205 |
| R7382P | M17 | M027K | 0.1110 |
| R7230P | M772 | M027H | 0.1084 |
| R7212P | M16 | M027R | 0.1034 |

| Fermentation No. AxxxP) | Mutation No. | Mutation | MALTOSE TRANSFERASE 33% Maltose 20 h Maltose-ester % |
|---|---|---|---|
| A744P | M775 | M027Y | 0.1032 |
| A749P | M14 | M027D | 0.0649 |
| R7232P | M775 | M027Y | 0.0634 |
| A017P | M17 | M027K | 0.0627 |
| A013P | M13 | M027N | 0.0618 |
| R7215P | M19 | M027G | 0.0612 |
| A016P | M16 | M027R | 0.0567 |
| A742P | M19 | M027G | 0.0521 |
| R7211P | M14 | M027D | 0.0506 |
| R7210P | M13 | M027N | 0.0397 |
| R4067P | M39 | L031Q | 0.0935 |
| R4068P | M41 | L031H | 0.0668 |
| A038P | M38 | L031N | 0.0591 |
| R7217P | M38 | L031N | 0.0563 |
| A033P | M33 | L031T | 0.0403 |
| R7236P | M39 | L031Q | 0.0331 |
| R7253P | M48 | V085R | 0.1023 |
| R7256P | M360 | A119T | 0.0312 |
| R7282P | M735 | Y120K | 0.0682 |
| R7261P | M241 | W122S | 0.0755 |
| F1227P | M241 | W122S | 0.0549 |
| F1223P | M239 | W122L | 0.0530 |
| R7378P | M866 | W122L | 0.0287 |
| R7284P | M244 | E201R | 0.0433 |
| R7285P | M767 | E201R | 0.0325 |
| R7400P | M268 | Q245S | 0.0350 |
| N80D Backbone | M549 | N80D | 0.0282 |

Therefore when determining 1$^{st}$ round winners after 20 h in a ranked order the following sites were identified as being key sites for use when engineering lipid acyltransferases: I086, M027, L031, V085, A119, Y120, W122, E201 and/or Q245.

In particular key modifications include I86R, Y; M27R, G, H, K, Y, D, N; L31Q, H, N, T; V85R; A119T; Y120K, W122S, L, E201R, Q245S.

Table 2 shows the maltose transferase activity as % maltose-ester after 1 hour, for each of the mutant variant lipid acyltransferases (with single point mutations as taught herein). The backbone is the *Aeromonas salmonicida* lipid acyltransferase comprising the N80D variation and encoded by the nucleotide sequence SEQ ID No. 25)—produced in *Bacillus licheniformis* production strain:

| Fermentation No. AxxxP) | Mutation No. | Mutation | MALTOSE TRANSFERASE 33% Maltose 1 h Maltose-ester % |
|---|---|---|---|
| R7377P | M39 | L031Q | 0.1382 |
| R7387P | M240 | W122A | 0.1202 |
| R7218P | M39 | L031Q | 0.1061 |
| R7236P | M39 | L031Q | 0.0988 |
| R7253P | M48 | V085R | 0.0891 |
| R7378P | M866 | W122L | 0.0814 |
| R7224P | M650 | L031F | 0.0725 |
| R7269P | M649 | V085D | 0.0694 |
| R7220P | M41 | L031H | 0.0681 |
| R7268P | M647 | V085E | 0.0672 |
| R7254P | M57 | I086R | 0.0650 |
| R7260P | M239 | W122L | 0.0576 |
| R7255P | M61 | I086Y | 0.0572 |
| R7210P | M13 | M027N | 0.0494 |
| R7261P | M241 | W122S | 0.0420 |
| R7216P | M33 | L031T | 0.0417 |
| R7283P | M736 | Y120E | 0.0395 |
| R7230P | M772 | M027H | 0.0316 |
| R7232P | M775 | M027Y | 0.0314 |
| R7382P | M17 | M027K | 0.0310 |
| R7225P | M651 | L031Y | 0.0294 |
| R7212P | M16 | M027R | 0.0235 |
| R7213P | M17 | M027K | 0.0107 |
| R7233P | M776 | M027R | 0.0101 |
| R7234P | M777 | M027R | 0.0085 |
| R7221P | M42 | L031C | 0.0231 |
| R7256P | M360 | A119T | 0.0096 |
| R7285P | M767 | E201R | 0.0105 |
| R7284P | M244 | E201R | 0.0076 |
| R7262P | M244 | E201R | 0.0067 |
| R7391P | M250 | W232G | 0.0154 |
| R7390P | M249 | W232S | 0.0154 |
| R7396P | M256 | F235A | 0.0254 |
| R7397P | M257 | F235V | 0.0212 |
| R7399P | M260 | A236G | 0.0131 |
| R7398P | M259 | A236E | 0.0116 |
| N80D backbone | M549 | N80D | 0.0059 |

Therefore when determining 1$^{st}$ round winners after 1 h in a ranked order the following sites were identified as being key sites for use when engineering lipid acyltransferases: L031, W122, V085, I086, M027, F235, W232, A236, E201, A119, Y120.

In particular key modifications include L031Q, F, H, T, Y, C; W122A, L, S; V85R, D, E; I86R, Y; M27N, H, Y, K, R; F235A, V; W232G, S; A236G, E; E201R, A119T, Y120E.

Tables 3 and 4 show the combination winners when analysing maltose transferase activity as % maltose-ester after 20 hours and 1 hour respectively, for each of the mutant variant lipid acyltransferases.

TABLE 3

(N80D)—Backbone

| Fermentation No. (RxxxxP) | Mutation No. | All Mutations | MALTOSE TRANSFERASE 33% Maltose 20 h Maltose-ester % |
|---|---|---|---|
| R7709P | M1169 | L31Q, N80D, I86S, W122F | 0.4020 |
| R7469P | M957 | L31Q, N80D, W122L | 0.3702 |
| R7703P | M1163 | L31Q, N80D, I86V, W122L | 0.3314 |
| R7695P | M1155 | L31Q, N80D, I86I, W122L | 0.3198 |
| R7739P | M1199 | L31Q, N80D, I86S, R130R | 0.2843 |
| R7818P | M1274 | L31Q, N80D, K82R, I86A | 0.2746 |
| R7706P | M1166 | L31Q, N80D, I86S, W122W | 0.2665 |
| R7712P | M1172 | L31Q, N80D, I86S, W122Y | 0.2567 |
| R7848P | M1304 | M27V, L31Q, N80D | 0.2490 |
| R7704P | M1164 | L31Q, N80D, I86A, W122L | 0.2476 |

TABLE 3-continued

| | | (N80D)—Backbone | |
|---|---|---|---|
| Fermentation No. (RxxxxP) | Mutation No. | All Mutations | MALTOSE TRANSFERASE 33% Maltose 20 h Maltose-ester % |
| R7470P | M958 | L31Q, N80D, W122L | 0.2474 |
| R7817P | M1273 | L31Q, N80D, I86S, G121S | 0.2446 |
| R7482P | M970 | L31Q, N80D, I86S | 0.2409 |
| R7799P | M1258 | L31Q, N80D, K82R, I86S | 0.2399 |
| R7775P | M1235 | L31Q, N80D, I86S, W122L, R130Y | 0.2288 |
| R7783P | M1243 | L31Q, N80D, I86S, W122L, R130V | 0.2226 |
| R7490P | M976 | L31Q, N80D, I86S | 0.2220 |
| R7702P | M1162 | L31Q, N80D, I86T, W122L | 0.2204 |
| R7708P | M1168 | L31Q, N80D, I86S, W122L | 0.2044 |
| R7734P | M1194 | L31Q, N80D, W122L, R130Q | 0.1954 |
| R7771P | M1231 | L31Q, N80D, I86S, W122L, R130R | 0.1784 |
| R7692P | M1152 | L31Q, N80D, I86S | 0.1745 |
| R7608P | M1094 | L31Q, N80D, G121R | 0.1728 |
| R7496P | M982 | L31Q, N80D, I86A | 0.1653 |
| R7847P | M1303 | M27C, L31Q, N80D | 0.1575 |
| R7844P | M1300 | M27Q, L31Q, N80D | 0.1534 |
| R7606P | M1092 | L31Q, N80D, G121S | 0.1502 |
| R7707P | M1167 | L31Q, N80D, I86S, W122R | 0.1488 |
| R7657P | M1143 | L31Q, N80D, R130Q | 0.1478 |
| R7715P | M1175 | L31Q, N80D, I86S, W122H | 0.1453 |
| R7697P | M1157 | L31Q, N80D, I86M, W122L | 0.1452 |
| R7654P | M1140 | L31Q, N80D, R130N | 0.1407 |
| R7705P | M1165 | L31Q, N80D, I86S, W122L | 0.1387 |
| R7537P | M1023 | L31Q, N80D, K82N | 0.1351 |
| R7798P | M1178 | L31Q, N80D, I86S, W122M | 0.1340 |
| R7477P | M965 | L31Q, N80D, W122L | 0.1323 |
| R7532P | M1018 | L31Q, N80D, K82H | 0.1313 |
| R7663P | M1149 | L31Q, N80D, R130H | 0.1308 |
| R7656P | M1142 | L31Q, N80D, R130A | 0.1280 |
| R7612P | M1098 | L31Q, N80D, G121S | 0.1259 |
| R7770P | M1230 | L31Q, N80D, I86S, W122L, R130D | 0.1244 |
| R7485P | M973 | L31Q, N80D, I86M | 0.1234 |
| R7562P | M1048 | L31Q, Y74Y, N80D | 0.1224 |
| R7653P | M1139 | L31Q, N80D, R130L | 0.1119 |
| R7673P | M1034 | L31Q, N80D, Y83F | 0.1097 |
| R7533P | M1019 | L31Q, N80D, K82S | 0.1063 |
| R7580P | M1066 | L31Q, I77T, N80D | 0.1061 |
| R7772P | M1232 | L31Q, N80D, I86S, W122L, R130I | 0.1036 |
| R7800P | M1152 | L31Q, N80D, I86S, W122L | 0.1012 |
| R7694P | M1154 | L31Q, N80D, I86F, W122L | 0.0965 |
| R7839P | M1295 | M27N, L31Q, N80D | 0.0964 |
| R7539P | M1025 | L31Q, N80D, Y83P | 0.0963 |
| R7648P | M1134 | L31Q, N80D, R130K | 0.0960 |
| R7802P | M1259 | L31Q, N80D, K82R, I86S, W122L | 0.0950 |
| R7536P | M1022 | L31Q, N80D, K82L | 0.0947 |
| R7756P | M1216 | L31Q, N80D, I86S, G121G | 0.0946 |
| R7820P | M1276 | L31Q, N80D, I86A, R130Q | 0.0932 |
| R7840P | M1296 | M27H, L31Q, N80D | 0.0901 |
| R7369P | M858 | L31Q, N80D, W122L, A207E | 0.0897 |
| R7735P | M1195 | L31Q, N80D, W122L, R130L | 0.0857 |
| R7531P | M1017 | L31Q, N80D, K82E | 0.0839 |
| R7609P | M1095 | L31Q, N80D, G121E | 0.0830 |
| R7721P | M1181 | L31Q, N80D, W122L, R130R | 0.0827 |
| R7582P | M1068 | L31Q, I77M, N80D | 0.0826 |
| R7529P | M1015 | L31Q, N80D, K82T | 0.0826 |
| R7372P | M861 | L31Q, N80D, W122L | 0.0807 |
| R7476P | M964 | L31Q, N80D, W122H | 0.0806 |
| R7601P | M1087 | L31Q, N80D, Q167T | 0.0803 |
| R7588P | M1074 | L31Q, I77H, N80D | 0.0801 |
| R7603P | M1089 | L31Q, N80D, G121K | 0.0791 |
| R7575P | M1061 | L31Q, I77Q, N80D | 0.0784 |
| R7731P | M1191 | L31Q, N80D, W122L, R130N | 0.0773 |
| R7381P | M861 | L31Q, N80D, W122L | 0.0760 |
| R7611P | M1097 | L31Q, N80D, G121D | 0.0715 |
| R7661P | M1147 | L31Q, N80D, R130T | 0.0699 |
| R7655P | M1141 | L31Q, N80D, R130T | 0.0697 |
| R7535P | M1021 | L31Q, N80D, K82M | 0.0695 |
| R7598P | M1084 | L31Q, N80D, Q167H | 0.0691 |
| R7498P | M984 | L31Q, N80D, I86T | 0.0674 |
| R7600P | M1086 | L31Q, N80D, Q167I | 0.0659 |
| R7497P | M983 | L31Q, N80D, I86C | 0.0657 |
| R7593P | M1079 | L31Q, N80D, Q167G | 0.0652 |
| R7843P | M1299 | M27L, L31Q, N80D | 0.0649 |

TABLE 3-continued

| | (N80D)—Backbone | | |
|---|---|---|---|
| Fermentation No. (RxxxxP) | Mutation No. | All Mutations | MALTOSE TRANSFERASE 33% Maltose 20 h Maltose-ester % |
| R7809P | M1265 | L31Q, N80D, I86S, G121R | 0.0644 |
| R7576P | M1062 | L31Q, I77S, N80D | 0.0642 |
| R7579P | M1065 | L31Q, I77C, N80D | 0.0640 |
| R7610P | M1096 | L31Q, N80D, G121N | 0.0628 |
| R7585P | M1071 | L31Q, I77A, N80D | 0.0621 |
| R7646P | M1132 | L31Q, N80D, R130M | 0.0604 |
| R7464P | M952 | L31Q, N80D, W122F | 0.0577 |
| R7846P | M1302 | M27G, L31Q, N80D | 0.0575 |
| R7538P | M1024 | L31Q, N80D, K82G | 0.0564 |
| R7778P | M1238 | L31Q, N80D, I86S, W122L, R130K | 0.0547 |
| R7642P | M1128 | L31Q, N80D, R130A | 0.0546 |
| R7492P | M978 | L31Q, N80D, I86I | 0.0541 |
| R7589P | M1075 | L31Q, I77E, N80D | 0.0510 |
| R7503P | M989 | L31Q, N80D, D227L | 0.0497 |
| R7450P | M939 | L31Q, N80D, V85H, N215G | 0.0494 |
| R7826P | M1282 | L31Q, N80D, I86A, W122L, R130N | 0.0484 |
| R7590P | M1076 | L31Q, I77R, N80D | 0.0477 |
| R7493P | M979 | L31Q, N80D, I86F | 0.0475 |
| R7698P | M1158 | L31Q, N80D, I86Y, W122L | 0.0465 |
| R7838P | M1294 | M27K, L31Q, N80D | 0.0463 |
| R7502P | M988 | L31Q, N80D, D227C | 0.0462 |
| R7664P | M1150 | L31Q, N80D, R130L | 0.0458 |
| R7701P | M1161 | L31Q, N80D, I86C, W122L | 0.0457 |
| R7592P | M1078 | L31Q, N80D, Q167L | 0.0452 |
| R7452P | M941 | L31Q, N80D, V85H | 0.0449 |
| R7596P | M1082 | L31Q, N80D, Q167M | 0.0447 |
| R7841P | M1297 | M27D, L31Q, N80D | 0.0439 |
| R7495P | M981 | L31Q, N80D, I86L | 0.0435 |
| R7528P | M1014 | L31Q, N80D, Y230A | 0.0428 |
| R7468P | M956 | L31Q, N80D, W122R | 0.0426 |
| R7525P | M1011 | L31Q, N80D, Y230G | 0.0419 |
| R7513P | M999 | L31Q, N80D, D227S | 0.0404 |
| R7368P | M857 | L31Q, N80D, W122L, A207E, N289P | 0.0404 |
| R7465P | M953 | L31Q, N80D, W122Y | 0.0396 |
| R7700P | M1160 | L31Q, N80D, I86L, W122L | 0.0395 |
| R7814P | M1270 | L31Q, N80D, K82R, I86S, G121S, R130Q | 0.0376 |
| R7681P | M1042 | L31Q, Y74W, N80D | 0.0375 |
| R7660P | M1146 | L31Q, N80D, R130F | 0.0370 |
| R7613P | M1099 | L31Q, N80D, G121V | 0.0367 |
| R7732P | M1192 | L31Q, N80D, W122L, R130M | 0.0366 |
| R7643P | M1129 | L31Q, N80D, R130V | 0.0365 |
| R7517P | M1003 | L31Q, N80D, Y230V | 0.0362 |
| R7451P | M940 | L31Q, N80D, N215G | 0.0357 |
| R7777P | M1237 | L31Q, N80D, I86S, W122L, R130N | 0.0356 |
| R7519P | M1005 | L31Q, N80D, Y230R | 0.0353 |
| R7845P | M1301 | M27E, L31Q, N80D | 0.0347 |
| R7526P | M1012 | L31Q, N80D, Y230I | 0.0345 |
| R7782P | M1242 | L31Q, N80D, I86S, W122L, R130S | 0.0343 |
| R7530P | M1016 | L31Q, N80D, K82R | 0.0342 |
| R7514P | M1000 | L31Q, N80D, D227E | 0.0336 |
| R7832P | M1288 | L31Q, N80D, K82R, I86A, G121S | 0.0331 |
| R7659P | M1145 | L31Q, N80D, R130G | 0.0329 |
| R7587P | M1073 | L31Q, I77V, N80D | 0.0329 |
| R7604P | M1090 | L31Q, N80D, G121G | 0.0328 |
| R7521P | M1007 | L31Q, N80D, Y230T | 0.0327 |
| R7807P | M1263 | L31Q, N80D, K82R, I86S, R130N | 0.0326 |
| R7504P | M990 | L31Q, N80D, D227F | 0.0322 |
| R7827P | M1283 | L31Q, N80D, I86A, G121R | 0.0318 |
| R7806P | M1262 | L31Q, N80D, I86S, R130N | 0.0303 |
| R7475P | M963 | L31Q, N80D, W122C | 0.0301 |
| R7518P | M1004 | L31Q, N80D, Y230S | 0.0293 |
| R7658P | M1144 | L31Q, N80D, R130Y | 0.0291 |
| R7665P | M1151 | L31Q, N80D, R130C | 0.0286 |
| R7591P | M1077 | L31Q, I77L, N80D | 0.0284 |
| N80D backbone | M549 | N80D | 0.0282 |

TABLE 4

| | | (N80D)—Backbone | |
|---|---|---|---|
| Fermentation No. (RxxxxP) | Mutation No. | All Mutations | MALTOSE TRANSFERASE 33% Maltose 1 h Maltose-ester % |
| R7843P | M1299 | M27L, L31Q, N80D | 0.2126 |
| R7849P | M1305 | M27S, L31Q, N80D | 0.1753 |
| R7507P | M993 | L31Q, N80D, D227V | 0.1667 |
| R7837P | M1293 | M27Y, L31Q, N80D | 0.1634 |
| R7500P | M986 | L31Q, N80D, D227I | 0.1626 |
| R7505P | M991 | L31Q, N80D, D227T | 0.1609 |
| R7509P | M995 | L31Q, N80D, D227Y | 0.1528 |
| R7530P | M1016 | L31Q, N80D, K82R | 0.1507 |
| R7491P | M977 | L31Q, N80D, I86L | 0.1505 |
| R7465P | M953 | L31Q, N80D, W122Y | 0.1491 |
| R7499P | M985 | L31Q, N80D, D227D | 0.1488 |
| R7501P | M987 | L31Q, N80D, D227H | 0.1485 |
| R7508P | M994 | L31Q, N80D, D227A | 0.1462 |
| R7835P | M1291 | M27F, L31Q, N80D | 0.1408 |
| R7481P | M969 | L31Q, N80D, I86I | 0.1402 |
| R7462P | M950 | L31Q, N80D, W122W | 0.1359 |
| R7836P | M1292 | M27T, L31Q, N80D | 0.1340 |
| R7373P | M862 | L31Q, N80D, A207E | 0.1334 |
| R7494P | M980 | L31Q, N80D, I86V | 0.1332 |
| R7498P | M984 | L31Q, N80D, I86T | 0.1315 |
| R7497P | M983 | L31Q, N80D, I86C | 0.1313 |
| R7511P | M997 | L31Q, N80D, D227R | 0.1312 |
| R7496P | M982 | L31Q, N80D, I86A | 0.1266 |
| R7703P | M1163 | L31Q, N80D, I86V, W122L | 0.1250 |
| R7687P | M1048 | L31Q, Y74Y, N80D | 0.1229 |
| R7512P | M998 | L31Q, N80D, D227G | 0.1227 |
| R7581P | M1067 | L31Q, I77I, N80D | 0.1224 |
| R7792P | M1252 | L31Q, N80D, G121E, 122L | 0.1217 |
| R7839P | M1295 | M27N, L31Q, N80D | 0.1206 |
| R7370P | M859 | L31Q, N80D, A207E, N289P | 0.1204 |
| R7644P | M1130 | L31Q, N80D, R130R | 0.1202 |
| R7476P | M964 | L31Q, N80D, W122H | 0.1198 |
| R7583P | M1069 | L31Q, I77F, N80D | 0.1180 |
| R7464P | M952 | L31Q, N80D, W122F | 0.1179 |
| R7369P | M858 | L31Q, N80D, W122L, A207E | 0.1165 |
| R7640P | M1126 | L31Q, N80D, R130R | 0.1137 |
| R7504P | M990 | L31Q, N80D, D227F | 0.1125 |
| R7650P | M1136 | L31Q, N80D, R130R | 0.1121 |
| R7592P | M1078 | L31Q, N80D, Q167L | 0.1107 |
| R7584P | M1070 | L31Q, I77Y, N80D | 0.1078 |
| R7709P | M1169 | L31Q, N80D, I86S, W122F | 0.1072 |
| R7610P | M1096 | L31Q, N80D, G121N | 0.1058 |
| R7605P | M1091 | L31Q, N80D, G121G | 0.1054 |
| R7594P | M1080 | L31Q, N80D, Q167L | 0.1054 |
| R7591P | M1077 | L31Q, I77L, N80D | 0.0987 |
| R7514P | M1000 | L31Q, N80D, D227E | 0.0982 |
| R7502P | M988 | L31Q, N80D, D227C | 0.0975 |
| R7587P | M1073 | L31Q, I77V, N80D | 0.0965 |
| R7817P | M1273 | L31Q, N80D, I86S, G121S | 0.0918 |
| R7468P | M956 | L31Q, N80D, W122R | 0.0911 |
| R7784P | M1244 | L31Q, N80D, G121G, 122L | 0.0889 |
| R7840P | M1296 | M27H, L31Q, N80D | 0.0888 |
| R7375P | M864 | N80D, W122L, A207E | 0.0872 |
| R7503P | M989 | L31Q, N80D, D227L | 0.0857 |
| R7374P | M863 | L31Q, N80D, N289P | 0.0843 |
| R7535P | M1021 | L31Q, N80D, K82M | 0.0822 |
| R7598P | M1084 | L31Q, N80D, Q167H | 0.0813 |
| R7513P | M999 | L31Q, N80D, D227S | 0.0811 |
| R7604P | M1090 | L31Q, N80D, G121G | 0.0796 |
| R7695P | M1155 | L31Q, N80D, I86I, W122L | 0.0793 |
| R7510P | M996 | L31Q, N80D, D227P | 0.0781 |
| R7451P | M940 | L31Q, N80D, N215G | 0.0769 |
| R7588P | M1074 | L31Q, I77H, N80D | 0.0769 |
| R7818P | M1274 | L31Q, N80D, K82R, I86A | 0.0716 |
| R7371P | M860 | N80D, W122L, A207E, N289P | 0.0704 |
| R7516P | M1002 | L31Q, N80D, Y230N | 0.0694 |
| R7582P | M1068 | L31Q, I77M, N80D | 0.0693 |
| R7608P | M1094 | L31Q, N80D, G121R | 0.0692 |
| R7673P | M1034 | L31Q, N80D, Y83F | 0.0632 |
| R7490P | M976 | L31Q, N80D, I86S | 0.0616 |
| R7704P | M1164 | L31Q, N80D, I86A, W122L | 0.0611 |
| R7596P | M1082 | L31Q, N80D, Q167M | 0.0591 |
| R7580P | M1066 | L31Q, I77T, N80D | 0.0567 |

TABLE 4-continued (N80D)—Backbone

| Fermentation No. (RxxxxP) | Mutation No. | All Mutations | MALTOSE TRANSFERASE 33% Maltose 1 h Maltose-ester % |
|---|---|---|---|
| R7612P | M1098 | L31Q, N80D, G121S | 0.0565 |
| R7372P | M861 | L31Q, N80D, W122L | 0.0556 |
| R7712P | M1172 | L31Q, N80D, I86S, W122Y | 0.0549 |
| R7495P | M981 | L31Q, N80D, I86L | 0.0541 |
| R7606P | M1092 | L31Q, N80D, G121S | 0.0532 |
| R7706P | M1166 | L31Q, N80D, I86S, W122W | 0.0522 |
| R7708P | M1168 | L31Q, N80D, I86S, W122L | 0.0521 |
| R7601P | M1087 | L31Q, N80D, Q167T | 0.0497 |
| R7562P | M1048 | L31Q, Y74Y, N80D | 0.0488 |
| R7795P | M1255 | L31Q, N80D, G121Q, 122L | 0.0473 |
| R7739P | M1199 | L31Q, N80D, I86S, R130R | 0.0459 |
| R7469P | M957 | L31Q, N80D, W122L | 0.0457 |
| R7654P | M1140 | L31Q, N80D, R130N | 0.0456 |
| R7518P | M1004 | L31Q, N80D, Y230S | 0.0446 |
| R7702P | M1162 | L31Q, N80D, I86T, W122L | 0.0440 |
| R7527P | M1013 | L31Q, N80D, Y230H | 0.0427 |
| R7492P | M978 | L31Q, N80D, I86I | 0.0397 |
| R7681P | M1042 | L31Q, Y74W, N80D | 0.0390 |
| R7663P | M1149 | L31Q, N80D, R130H | 0.0389 |
| R7482P | M970 | L31Q, N80D, I86S | 0.0388 |
| R7536P | M1022 | L31Q, N80D, K82L | 0.0383 |
| R7603P | M1089 | L31Q, N80D, G121K | 0.0377 |
| R7848P | M1304 | M27V, L31Q, N80D | 0.0369 |
| R7532P | M1018 | L31Q, N80D, K82H | 0.0362 |
| R7376P | M865 | N80D, A207E, N289P | 0.0361 |
| R7657P | M1143 | L31Q, N80D, R130Q | 0.0349 |
| R7705P | M1165 | L31Q, N80D, I86S, W122L | 0.0344 |
| R7697P | M1157 | L31Q, N80D, I86M, W122L | 0.0331 |
| R7734P | M1194 | L31Q, N80D, W122L, R130Q | 0.0329 |
| R7844P | M1300 | M27Q, L31Q, N80D | 0.0324 |
| R7756P | M1216 | L31Q, N80D, I86S, G121G | 0.0318 |
| R7524P | M1010 | L31Q, N80D, Y230Q | 0.0306 |
| R7799P | M1258 | L31Q, N80D, K82R, I86S | 0.0306 |
| R7600P | M1086 | L31Q, N80D, Q167I | 0.0303 |
| R7820P | M1276 | L31Q, N80D, I86A, R130Q | 0.0302 |
| R7537P | M1023 | L31Q, N80D, K82N | 0.0301 |
| R7593P | M1079 | L31Q, N80D, Q167G | 0.0293 |
| R7707P | M1167 | L31Q, N80D, I86S, W122R | 0.0286 |
| R7692P | M1152 | L31Q, N80D, I86S | 0.0274 |
| R7381P | M861 | L31Q, N80D, W122L | 0.0270 |
| R7450P | M939 | L31Q, N80D, V85H, N215G | 0.0269 |
| R7847P | M1303 | M27C, L31Q, N80D | 0.0268 |
| R7528P | M1014 | L31Q, N80D, Y230A | 0.0261 |
| R7525P | M1011 | L31Q, N80D, Y230G | 0.0256 |
| R7715P | M1175 | L31Q, N80D, I86S, W122H | 0.0252 |
| R7519P | M1005 | L31Q, N80D, Y230R | 0.0247 |
| R7585P | M1071 | L31Q, I77A, N80D | 0.0247 |
| R7452P | M941 | L31Q, N80D, V85H | 0.0247 |
| R7477P | M965 | L31Q, N80D, W122L | 0.0246 |
| R7520P | M1006 | L31Q, N80D, Y230K | 0.0246 |
| R7470P | M958 | L31Q, N80D, W122L | 0.0234 |
| R7609P | M1095 | L31Q, N80D, G121E | 0.0227 |
| R7694P | M1154 | L31Q, N80D, I86F, W122L | 0.0227 |
| R7656P | M1142 | L31Q, N80D, R130A | 0.0220 |
| R7368P | M857 | L31Q, N80D, W122L, A207E, N289P | 0.0219 |
| R7539P | M1025 | L31Q, N80D, Y83P | 0.0217 |
| R7611P | M1097 | L31Q, N80D, G121D | 0.0217 |
| R7789P | M1249 | L31Q, N80D, G121R, 122L | 0.0209 |
| R7533P | M1019 | L31Q, N80D, K82S | 0.0204 |
| R7485P | M973 | L31Q, N80D, I86M | 0.0200 |
| R7575P | M1061 | L31Q, I77Q, N80D | 0.0191 |
| R7653P | M1139 | L31Q, N80D, R130L | 0.0191 |
| R7771P | M1231 | L31Q, N80D, I86S, W122L, R130R | 0.0183 |
| R7531P | M1017 | L31Q, N80D, K82E | 0.0178 |
| R7522P | M1008 | L31Q, N80D, Y230D | 0.0171 |
| R7589P | M1075 | L31Q, I77E, N80D | 0.0167 |
| R7790P | M1250 | L31Q, N80D, G121S, 122L | 0.0167 |
| R7529P | M1015 | L31Q, N80D, K82T | 0.0166 |
| R7590P | M1076 | L31Q, I77R, N80D | 0.0164 |
| R7579P | M1065 | L31Q, I77C, N80D | 0.0164 |
| R7576P | M1062 | L31Q, I77S, N80D | 0.0159 |
| R7735P | M1195 | L31Q, N80D, W122L, R130L | 0.0158 |
| R7648P | M1134 | L31Q, N80D, R130K | 0.0153 |

TABLE 4-continued

(N80D)—Backbone

| Fermentation No. (RxxxxP) | Mutation No. | All Mutations | MALTOSE TRANSFERASE 33% Maltose 1 h Maltose-ester % |
|---|---|---|---|
| R7731P | M1191 | L31Q, N80D, W122L, R130N | 0.0148 |
| R7785P | M1245 | L31Q, N80D, G121A, 122L | 0.0138 |
| R7538P | M1024 | L31Q, N80D, K82G | 0.0136 |
| R7721P | M1181 | L31Q, N80D, W122L, R130R | 0.0132 |
| R7798P | M1178 | L31Q, N80D, I86S, W122M | 0.0129 |
| R7613P | M1099 | L31Q, N80D, G121V | 0.0123 |
| R7517P | M1003 | L31Q, N80D, Y230V | 0.0119 |
| R7526P | M1012 | L31Q, N80D, Y230I | 0.0114 |
| R7661P | M1147 | L31Q, N80D, R130T | 0.0110 |
| R7493P | M979 | L31Q, N80D, I86F | 0.0103 |
| R7698P | M1158 | L31Q, N80D, I86Y, W122L | 0.0097 |
| R7846P | M1302 | M27G, L31Q, N80D | 0.0095 |
| R7521P | M1007 | L31Q, N80D, Y230T | 0.0088 |
| R7655P | M1141 | L31Q, N80D, R130T | 0.0087 |
| R7777P | M1237 | L31Q, N80D, I86S, W122L, R130N | 0.0084 |
| R7732P | M1192 | L31Q, N80D, W122L, R130M | 0.0077 |
| R7814P | M1270 | L31Q, N80D, K82R, I86S, G121S, R130Q | 0.0076 |
| R7660P | M1146 | L31Q, N80D, R130F | 0.0074 |
| R7783P | M1243 | L31Q, N80D, I86S, W122L, R130V | 0.0074 |
| R7816P | M1272 | L31Q, N80D, K82R, I86S, G121S, R130N | 0.0069 |
| R7456P | M945 | L31Q, N80D, I86Y | 0.0069 |
| R7646P | M1132 | L31Q, N80D, R130M | 0.0066 |
| R7722P | M1182 | L31Q, N80D, W122L, R130T | 0.0066 |
| R7515P | M1001 | L31Q, N80D, Y230E | 0.0065 |
| R7664P | M1150 | L31Q, N80D, R130L | 0.0064 |
| R7659P | M1145 | L31Q, N80D, R130G | 0.0063 |
| R7725P | M1185 | L31Q, N80D, W122L, R130H | 0.0062 |
| R7665P | M1151 | L31Q, N80D, R130C | 0.0060 |
| R7802P | M1259 | L31Q, N80D, K82R, I86S, W122L | 0.0060 |
| N80D backbone | M549 | N80D | 0.0059 |

For the avoidance of doubt the lipid acyltransferase backbone when aligned (on a primary or tertiary basis) with the lipid acyltransferase enzyme shown herein as SEQ ID No. 16 or 6 preferably has D in position 80. We have therefore shown in the above tables N80D as a modification. However, in reality the backbone used in the above experiments already contained the N80D modification and therefore the other modifications could have been expressed without referencing the N80D modification, i.e. L31Q, N80D, W122L could have been expressed as L31Q, W122L.

However, it is important to note that the N80D modification is a preferred modification and a backbone enzyme is preferably used which already possesses amino acid D in position 80. If, however, a backbone is used which does not contain amino acid D in position (such as one more of the lipid acyltransferases shown here as SEQ ID No. 1, 3, 4, 5, 8, or 9 for instance) then preferably an additional modification of N80D is included.

EXAMPLE 2

Lipid Acyltransferase Variants in Baking

The enzymes which showed the most promise were tested in baking.

Hydrolytic Activity Protocol:
Substrate:
1.75% L-α Plant Phosphatidylcholin 95% (Avanti Polar Lipids, USA), 6.3% Triton X-100 and 5 mM CaCl$_2$ dissolved in 50 mm Hepes pH 7.0.
Assay Procedure:
Samples, calibration, and control were diluted in 10 mM HEPES pH 7.0, 0.1% Triton X-100. Analysis was carried out using a Konelab Autoanalyzer (Thermo, Finland). The assay was run at 30° C. 34 µL substrate was thermostatted for 180 seconds, before 4 µL sample was added. Enzymation lasted 600 sec. The amount of free fatty acid liberated during enzymation was measured using the NEFA C kit (WAKO, Germany). 56 µL NEFA A was added and the mixture was incubated for 300 sec. Afterwards 113 µL NEFA B was added and the mixture was incubated for 300 sec. OD 520 nm was then measured. Enzyme activity (µmol FFA/min·mL) was calculated based on a standard enzyme preparation.

Dough Slurry Protocol:
Enzymatic Incubation:
4.0 g flour (Reform flour DK 200700021) was weighed into a wheaton glass tube. Enzyme was dosed at 10 mg/kg flour. For substrate spiked dough slurry PC (L-α Plant Phosphatidylcholin 95% (Avanti Polar Lipids) solution and maltose (D-(+)-Maltose monohydrate, Sigma) solution was added to the appropriate concentrations. Total volume added was adjusted to 1.5 mL with 0.1% NaCl. A blind sample (0.1% NaCl) was included for every PC-maltose concentration setup. Enzymation was run at 40° C. with stifling (400 rpm) in a heating block (Block: Variomag Multitherm. Temperature control unit: Variomag Thermomodul 40 ST). 2.3 g samples were withdrawn at time t=30, 60 and 180 min, for blind samples a sample was also taken at time t=0 min.

Lipid Extraction
6.0 mL Butanol:Ethanol (85:15 (v/v)) was immediately added to the 2.3 g sample withdrawn and then mixed for 15 sec. on a vortex before being placed on a rotormixer at 35 rpm for 5 min. Afterwards the sample was placed in a water bath at 97° C. for 10 minutes, followed by mixing on a rotormixer at 35 rpm for one hour. The sample was then centrifuged at 1370 g for ten minutes. The supernatant being the organic phase containing the extracted lipid was then transferred to new glass tube. For HPTLC 1.5 mL of the extracted lipid was evaporated at 70° C. under nitrogen cover and then redispersed in 400 µL hexane:isopropanol (3:2 (v/v)). 3 µL redispersed extracted lipid was applied to the TLC plate, see below.

HPTLC:

High Performance Thin Layer Chromatography was used for analysis of maltose ester (ME) in dough slurry assay.

Procedure:

HPTLC plates (20×10 cm, Merck no. 1.05641) were activated by drying (160° C., 20-30 minutes) and standard and samples were applied using an Automatic HPTLC Applicator (ATS4, CAMAG). Plate elution was performed using an Automatic Developing Chamber (ADC2, CAMAG) (7 cm). After elution, plates were dried (160° C., 10 minutes), cooled, and immersed (10 seconds) in developing fluid (6% cupric acetate in 16% $H_3PO_4$). After drying (160° C., 6 minutes) plates were evaluated visually using a TLC scanner (TLC Scanner 3, CAMAG).

Four particularly interesting combinations were identified as:

L31Q, N80D, W122L (which can be expressed as L31Q, W122L where the backbone enzyme already has D in position 80);

M27V, L31Q, N80D (which can be expressed as N27V, L31Q where the backbone enzyme already has D in position 80);

L31Q, N80D, K82R, I86A (which can be expressed as L31Q, K82R, I86A where the backbone enzyme already has D in position 80); and/or L31Q, N80D, I86S, W122F (which can be expressed as L31Q, I86S, W122F where the backbone enzyme already has D in position 80).

Figure 38:
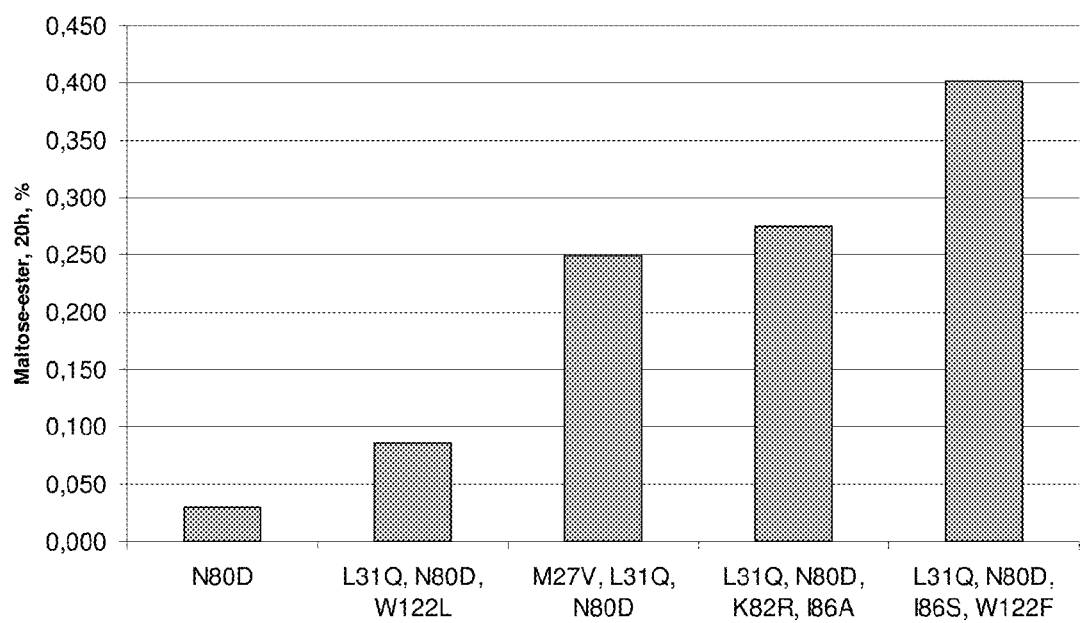
FIG. 38 shows a graph of the screening results in vitro which evaluated maltose-ester generation=f(100 µl/g egg yolk, 20 h) with the backbone lipid acyltransferase enzyme from *Aeromonas salmonicida* (comprising the N80D variation); and 4 variant enzymes.
Figure 39:
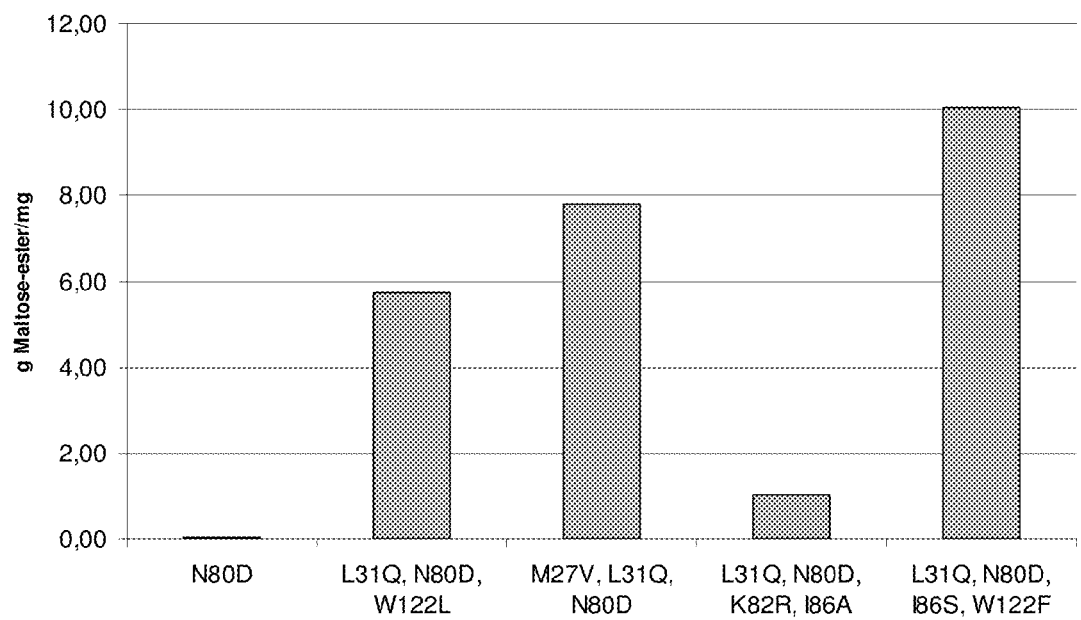
FIG. 39 shows a graph of the screening results in vitro which evaluated maltose-ester generation g methyl ester (ME)/mg enzyme protein with the backbone lipid acyltransferase enzyme from *Aeromonas salmonicida* (comprising the N80D variation); and 4 variant enzymes.
Figure 40:
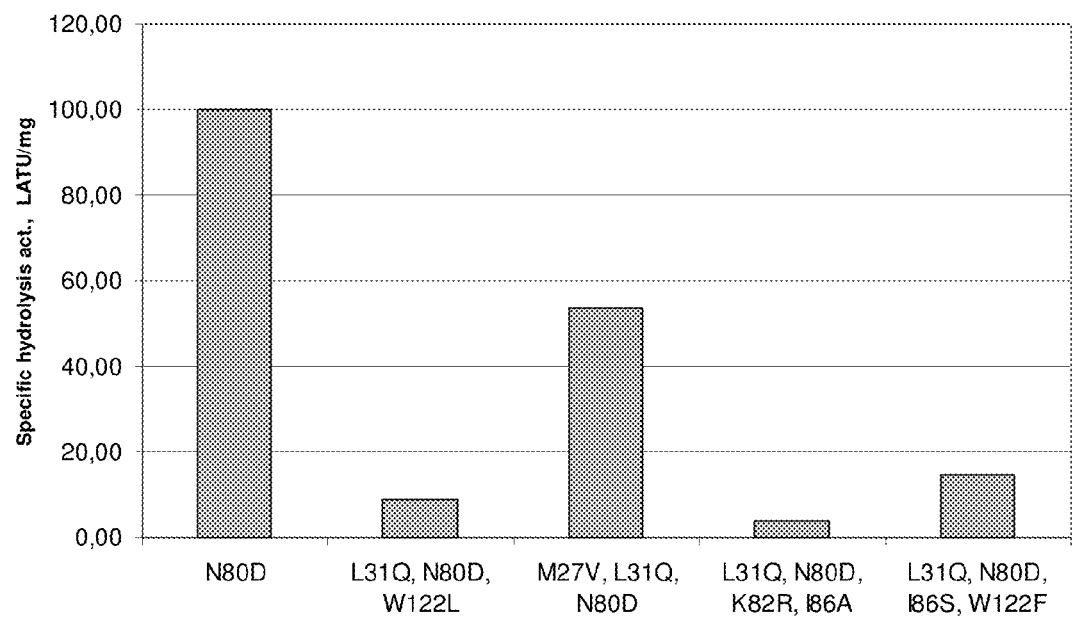
FIG. 40 shows a graph from $3^{rd}$ round screening in vitro which evaluates the hydrolysis activity of the enzyme (LATU/mg enzyme protein) with the backbone lipid acyltransferase enzyme from *Aeromonas salmonicida* (comprising the N80D variation); and 4 variant enzymes.

These specific combinations (as well as other combinations) were found to have an improved activity compared with the backbone lipid acyltransferase for a number of reasons:

(a) they were able to change the acceptor preference of the enzyme significantly. By way of example the variant enzymes were able use carbohydrate (particularly maltose) as an acyl acceptor more effectively than the backbone lipid acyltransferase (N80D) enzyme in this regard we direct you to the data shown in FIG. 38 and FIG. 39; and/or (b) they were able to change the specificity of the lipid acyltransferase enzyme significantly. By way of example the variant enzymes has a significantly reduced hydrolysis activity (see the data shown in FIG. 40). In fact, the variant enzymes had very little hydrolysis activity left.

Figure 41:
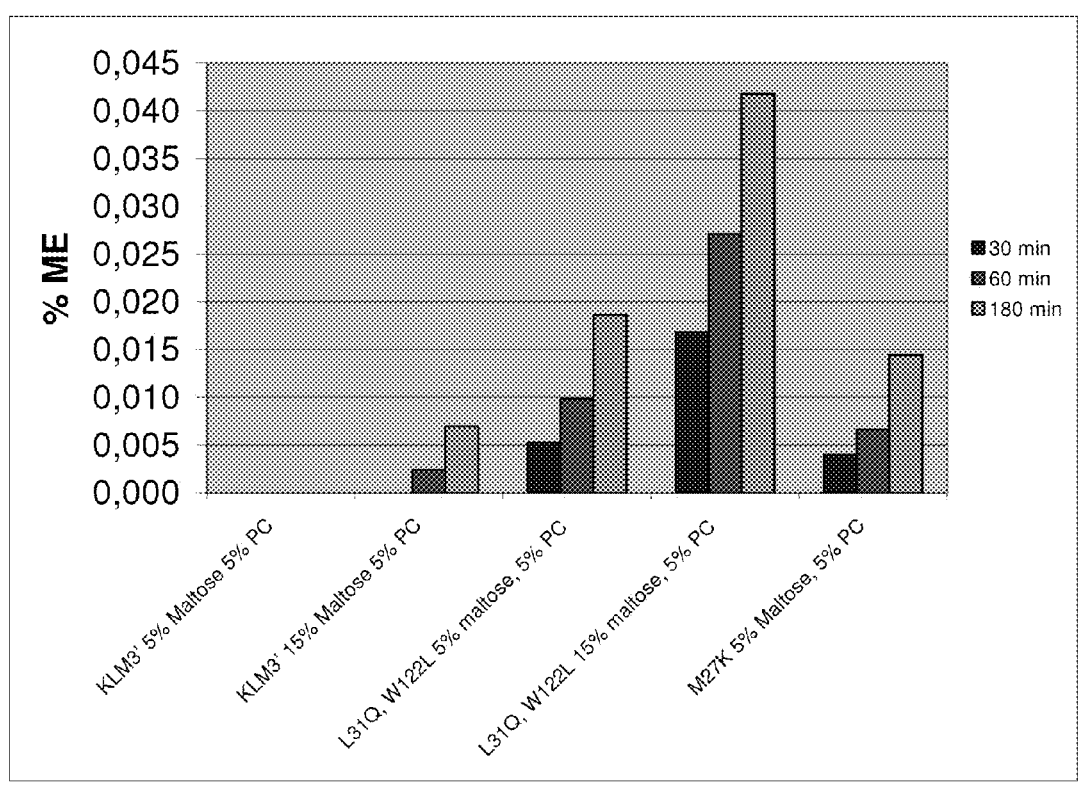
FIG. 41 shows a graph in a dough slurry showing % maltose ester generation using the backbone lipid acyltransferase enzyme from *Aeromonas salmonicida* (comprising the N80D variation), and two variants M27K and L31Q, W122L when dosed at 10 mg/kg flour.

In a dough slurry test the following variants were shown to improve maltose ester production: M27K, N80D (otherwise known as a single point mutation M27K—where the backbone enzyme has amino acid D at position 80) and L31Q, N80D, W122L (otherwise known as L31Q, W122L where the backbone enzyme has amino acid D at position 80). The results are shown in FIG. 41. The variants showed a significantly changed acceptor preference. By way of example the variant enzymes were able use carbohydrate (particularly maltose) as an acyl acceptor more effectively than the backbone lipid acyltransferase (N80D)—referred to therein as KLM3'.

EXAMPLE 3

Lipid Acyltransferase Variants in Degumming

The aim of the present experiment was to analyse the performance of three lipid acyltransferase variants according to the present invention (designated EDS 226 [having N80D, A119I mutation], K710 [having N80D, A119T mutation] and K916 [having N80D, G67A, V85H mutations]) in water degumming of crude soy bean oil. The results are compared with previous water degumming experiments with the backbone lipid acyltransferase (sometimes referred to herein as KLM3'), namely the lipid acyltransferase from *Aeromonas salmonicida* with an N80D mutation and which is post-translationally clipped when expressed in *Bacillus licheniformis* (the sequence for which is shown herein as SEQ ID No. 16). The evaluated mutants are variants of the *Aeromonas Salmonicida* glycerophospholipid cholesterol acyltransferase (lipid acyltransferase), being expressed in *Bacillus lichiniformis*.

K710 proved to be highly hydrolytic, as observed from the total phosphor content of the oil, being reduced to approximately 32 ppm compared to 42 and 56 ppm in oils degummed with EDS 226 and K916. Furthermore K710 attributed to a higher content of phytosterol esters and free fatty acids (FFA's) in the oil than EDS 226 and K916.

Water degumming with the lipid acyltransferase mutants in highest concentrations attributed to a higher oil yield increase than normally observed with the backbone lipid acyltransferase. Generally, K710 proved to be more hydrolytic than the backbone lipid acyltransferase, while EDS 226 and K916 were comparable to the backbone lipid acyltransferase.

The performance of the three mutants (EDS 226, K710 and K916) in water degumming of crude soya bean oil was analysed. The mutants share the same backbone as the backbone lipid acyltransferase (i.e. all with mutation N80D), but have one or two additional mutation sites. It is of interest to compare the hydrolytic activity of the mutants with the backbone lipid acyltransferase in order to evaluate the possibility for application of other enzymes in the water degumming process.

Materials and Methods

Materials

Enzymes

Three lipid acyltransferase mutants (EDS 226, K710 and K916) originating from *Aeromonas salmonicida* were tested. The enzymes are glycerophospholipid cholesterol acyltransferases (GCAT) with mutations, other than N80D, as indicated in the Table below:

TABLE

Specifications of the lipid acyltransferase mutants: mutation site, activity, formulation media and enzyme solutions.

| Mutant | Mutations site(s) | Enzyme activity LATU-K/g | Formulation media | Solubility (3% NaCl dilution) |
|---|---|---|---|---|
| EDS 226 | A119I | 69 | Starch | 0.25 g in 2.5 ml |
| K710 | A119T | 1069 | Starch | 0.25 g in 2.5 ml |
| K916 | G67A, V85H | 42 | maltodextrin | 1 g in 5 ml |

Definition of Enzyme Activity

The activity of the backbone lipid acyltransferase is defined in Lipid Acyl Transferase Unit (LATU). 1 LATU is defined according to a standard enzyme. The assay is based on the enzyme's ability to hydrolyze lecithin and liberate free fatty acids (µmol FFA/min*ml). Assays conditions: (substrate: phosphatidylcholine, temperature 30° C., pH 7.0). LATU-K assays denote that the enzyme is diluted in 3% NaCl and is carried out to avoid precipitation of the enzyme.

Oil

Crude soya bean oil from The Solae Company (January 2008) was applied in the degumming trials.

Samples for Degumming

Samples (control and enzymatic) for water degumming trials are shown in the Table below:

TABLE

Samples for water degumming trials: Sample 1: control, 2: EDS 226 (0.1 LATU-K/g), 3: K710 (0.2 LATU-K/g), 4: K710 (0.4 LATU-K/g), 5: K710 (0.9 LATU-K/g) 6: K916 (0.04 LATU-K/g), 7: K916 (0.1 LATU-K/g) and 8: K916 (0.2 LATU-K/g).

| | | Samples | | | | | | | |
|---|---|---|---|---|---|---|---|---|---|
| | | Control | EDS 226 | K710 | K710 | K710 | K916 | K916 | K916 |
| Oil | g | 100 | 100 | 100 | 100 | 100 | 100 | 100 | 100 |
| EDS 226 | ml | 0 | 2 | | | | | | |
| K710 | ml | | | 0.16 | 0.41 | 0.82 | | | |
| K916 | ml | | | | | | 0.42 | 1.05 | 2 |
| Extra 3%-NaCl | ml | 2.00 | 0.00 | 1.84 | 1.59 | 1.18 | 1.58 | 0.95 | 0.00 |
| LATU-K/g oil | | 0.00 | 0.1 | 0.2 | 0.4 | 0.9 | 0.04 | 0.1 | 0.2 |
| 3%-NaCl water | % | 2 | 2 | 2 | 2 | 2 | 2 | 2 | 2 |

Methods

Water Degumming Lab Procedure 100 g crude soya oil was scaled into a 250 ml blue cap flask with lid and placed on a heating plate (55° C.). Water was immediately added to the oil followed by enzyme addition and the solution was homogenised, using an Ultra Turrax mixer for 30 seconds. The oil was placed on the heating plate for 30 minutes under magnetic stirring (450 rpm). After 30 minutes of activity, approximately 10 ml oil was transferred to a 12 ml centrifuge tube (previously scaled). The oil was heated to 97° C. in a boiling water bath for 10 minutes to inactivate the enzyme.

Preparation of Gum Samples for HPTLC Analysis

After heating, the oil was centrifuged at 3000 rcf for 3 minutes. The oil was decanted off and the tubes were drained for 15 minutes (tubes were placed up side down for 15 minutes). Weight of the gum and oil phase was measured.

High-Performance-Thin-Layer-Chromatography (HPTLC)

The content of triglycerides in the gum phase and phospholipid content in oil and gum was semi-quantified by HPTLC.

Apparatus

Applicator: Automatic TLC Sampler 4, CAMAG ADC2 Automatic developing chamber programmed to an elution length of 7 cm of migration.

HPTLC plate: 20×10 cm, Merck no. 1.05641. Activated at a CAMAG TLC Plate Heater III for 10 minutes at 160° C. before use.

Development: the HPTLC plate was dried on a CAMAG TLC Plate Heater III for 10 minutes at 160° C., cooled, and dipped in 6% cupric acetate in 16% $H_3PO_4$. Additionally dried for 10 minutes at 160° C. and evaluated directly.

Methods

Analysis of Triglyceride Content in Gum

The gum phase obtained from approximately 10 ml oil was diluted in 7.5 ml hexane:isopropanol (3:2) (solution A). 200 µl of solution A was diluted in 600 µl hexane:isopropanol (3:2) (solution B).

Solution B was applied (0.3 µl) to the HPTLC plate by an automatic TLC applicator.

Standard: 0.5% refined rapeseed oil was applied (0.1, 0.3, 0.5, 0.8 and 1.5 µl) on the HPTLC plate by an automatic TLC applicator.

Running buffer 5: P-ether:Methyl-tert-butyl ketone:Acetic acid 70:30:1.

Analysis of Phospholipids in Gum

The gum phase from approximately 10 g oil was dissolved in 7.5 ml hexane:isopropanol (3:2). 1 µl of the sample was applied to the HPTLC plate.

Gum standard: gum from the control was applied (0.1, 0.3, 0.5, 0.8 and 1.0 µl) to the HPTLC plate by an automatic TLC applicator.

Running buffer 6: Methylacetate:Chloroform:1-propanol: Methanol:25% KCl in water 25:25:25:10:9.

Analysis of Phospholipids in Oil

Approximately 80-100 mg oil was diluted in 1 ml hexane: isopropanol (3:2) and applied (5 µl) to the HPTLC plate by an automatic TLC applicator.

Phospholipid standard: no. 16 (0.5% phospholipid (Spectra Lipid, Germany) diluted in $CHCl_3$) was applied (0.1, 0.3, 0.5, 0.8 and 1.5 µl) to the HPTLC plate by an automatic TLC applicator.

Calculation of Triglycerides in Gum

Figure 43:
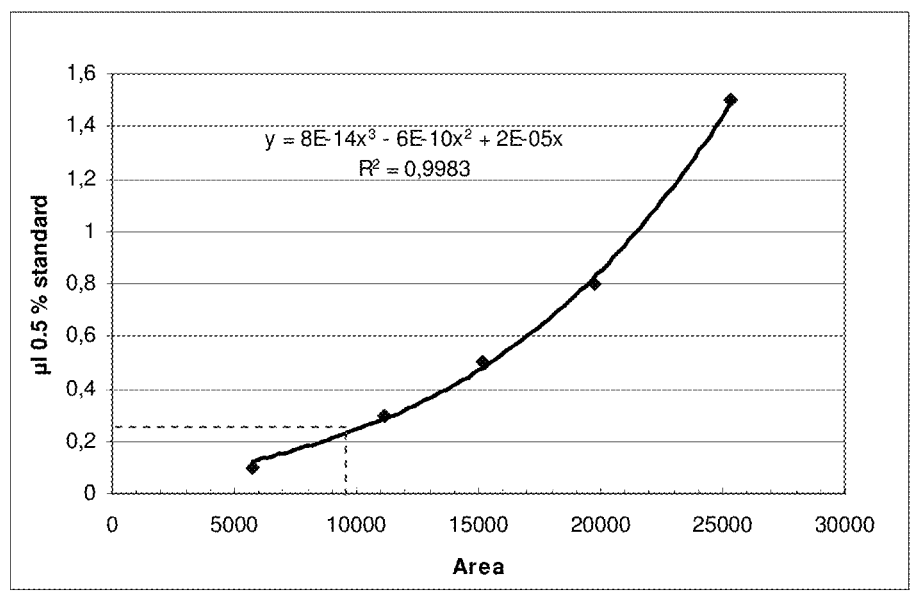
FIG. 43 shows a Standard curve based on attachment (0.1, 0.3, 0.5, 0.8 and 1.5 µl) of 0.5% refined rapeseed oil (standard) as a function of measured triglyceride area on the TLC plate.
Figure 44:
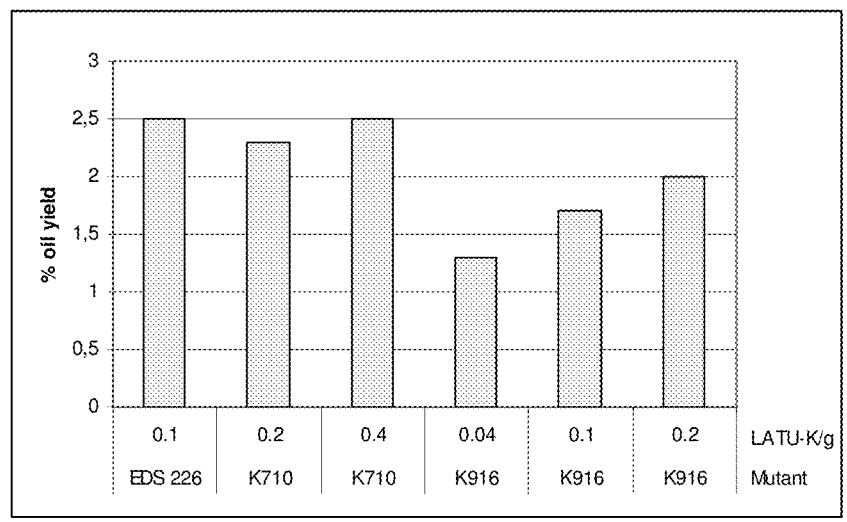
FIG. 44 shows oil yield (%) calculated from the amount of gum (control) subtracted amount of gum (enzymatic sample). Sample 5 is not shown due to analysis error. Sample 2: EDS 226 (0.1 LATU-K/g), 3: K710 (0.2 LATU-K/g), 4: K710 (0.4 LATU-K/g), 6: K916 (0.04 LATU-K/g), 7: K916 (0.1 LATU-K/g) and 8: K916 (0.2 LATU-K/g)

FIG. 43 shows the standard curve is calculated on the basis of applied amount (0.1, 0.3, 0.5, 0.8 and 1.5 µl) of 0.5% refined rapeseed oil as function of the area of triglycerides (measured on the TLC plate).

The content of triglycerides in enzymatic gum samples is estimated from the equation of the standard curve and the area of triglycerides in enzymatic samples (measured on TLC plate).

Example, Sample 3:

In sample 3, the area of triglyceride is measured to 9647 (FIG. 43) on the TLC plate, corresponding to applying 0.231 µl of the standard on the TLC plate.

Calculation of % triglycerides: In sample 3, 0.438 g gum was dissolved in 7.5 ml $CHCl_3$/MeOH, diluted 4 times and applied (0.3 µl) to the TLC plate. The standard contains 0.5 g/ml triglyceride, hence the amount of triglyceride in sample 3 is: (0.231 µl*0.5 g/ml*7.5 ml*4)/(0.3 µl*0.438 g)=26.4% triglyceride Calculation of Phospholipids in Gum A standard curve was made, based on gum from the control (no enzyme) in order to calculate the phospholipid content in enzymatic samples. Control gum was applied in 0.1, 0.3, 0.5, 0.8 and 1.0 µl to the TLC plate. The phospholipid degradation (%) in enzymatic samples was calculated relatively to the control, by assuming that no phospholipid degradation takes place in the control gum (=100% PA, PE, PC respectively).

Calculation of Phospholipid Content in Oil

Content (ppm) of PA, PE and PC was calculated in the oil phase, by same principle as calculation of the triglyceride content in gum. A standard curve was made, based on a standard containing 0.5% phospholipid. The content of each phospholipid in enzymatic samples is calculated from the content (%) in the standard and the molecular weight of the phospholipids (see Table below).

TABLE

Content and molecular weight of PA, PE and PC in standard

| | Molecular weight (g/mol) | % |
|---|---|---|
| PA | 685 | 5.13 |
| PE | 725 | 12.74 |
| PC | 770 | 14.76 |

Example, Sample 3:

0.088 g oil was dissolved in 1 ml CHCl$_3$/MeOH and 5 µl is attached on the TLC plate.

% PA: the detected area (1779) of PA in sample 3 corresponds to 0.983 µl of the standard (attached on the TLC plate, graph not shown). The standard contains 0.5% phospholipid, whereof PA makes out 5.13%. Hence, the PA content in sample 3 is: (0.983 µl*0.5 g/ml*0.0513)/(5 µl*0.088 g)=0.0573% ppm Phosphor from PA:

is calculated on the basis of molecular weight of phosphor and PA: 0.0573%*10000*(32 g/mol/685 g/mol)=26.8 ppm Gas Chromatography (GC) Analysis Oil samples were analysed for phytosterols, phytosterol esters and free fatty acids (FFA) by gas chromatography (Emulsifiers Analysis).

Apparatus

Perkin Elmer Autosystem 9000 Capillary Gas Chromatograph equipped with WCOT fused silica column 12.5 m×0.25 mm ID×0.1µ film thickness 5% phenyl-methyl-silicone (CP Sil 8 CB from Chrompack).

Carrier gas: Helium.

Injector: PSSI cold split injection (initial temp 50° C. heated to 385° C.), volume 1.0 µl Detector FID: 395° C.

Oven program (used since 30 Oct. 2003):

| | 1 | 2 | 3 |
|---|---|---|---|
| Oven temperature, ° C. | 90 | 280 | 350 |
| Isothermal, time, min. | 1 | 0 | 10 |
| Temperature rate, ° C./min. | | 15 | 4 |

Sample Preparation

The sample was dissolved in 12 ml Heptane:Pyridin, 2:1 containing internal standard heptadecane, 0.5 mg/ml. 5000 sample solution was transferred to a crimp vial, 100 µl MSTFA (N-Methyl-N-trimethylsilyl-trifluoraceamid) was added and reacted for 15 minutes at 60° C.

Calculation

Response factors for phytosterols, phytosteryl palmitate and phytosteryl stearate are determined based on pure reference material (weighing for pure material 10 mg).

Results and Discussion

Evaluation of the Lipid Acyltransferase Mutants

In the following section, results from TLC-analysis (phospholipids and triglycerides) and GC-analysis (FFA's, phytosterols and phytosterol esters) of the oil and gum phase are presented.

The properties of the lipid acyltransferase mutants in water degumming are compared with previous results with backbone lipid acyltransferase.

Oil Analysis

Analysis of Oil Yield

Increased oil yield, achieved from enzymatic degumming is shown in 44. Calculations are based on the amount of gum in the control subtracted the amount of gum in enzymatic samples.

Highest oil yield increase (2.3-2.5%) is obtained with EDS 226 (0.1 LATU-K/g) and K710 (0.2 and 0.4 LATU-K/g) and slightly less (1.7-2%) is achieved by K916 (0.1-0.2 LATU-K/g). Comparatively, the lipid acyltransferase backbone in concentrations ranging from 0.1 to 0.2 LATU-K/g, contributes to an increased oil yield of 1.3-1.6%. Hence, EDS 226, K710 and K916 attribute to an increase in oil yield compared to the lipid acyltransferase backbone.

Analysis of Phospholipid and Phosphor Content

The Table below shows the content (ppm) of phospholipids (phosphatidylcholine, phosphatidyl-ethanolamine and phosphatidic acid) in water degummed oils (control and enzymatic samples).

TABLE

| | Sample | | | | | | |
|---|---|---|---|---|---|---|---|
| Mutant | Control | EDS 226 | K710 | K710 | K916 | K916 | K916 |
| LATU-K/g | 0.0 | 0.1 | 0.2 | 0.4 | 0.04 | 0.1 | 0.2 |
| PA | 35.3 | 35.5 | 26.8 | 27.9 | 30.5 | 34.8 | 41.8 |
| PE | 8.7 | 0 | 0 | 0 | 1.2 | 3.0 | 2.0 |
| PC | 13 | 6.6 | 5.0 | 5.3 | 6.7 | 9.8 | 11.9 |
| Total phosphor content | 56.9 | 42.1 | 31.8 | 33.2 | 38.4 | 47.6 | 55.7 |

Content (ppm) of phosphor from PA, PE, PC and total phosphor in oils, degummed with varying concentrations of KLM3' mutants.
Sample
1: control,
2: EDS 226 (0.1 LATU-K/g),
3: K710 (0.2 LATU-K/g),
4: K710 (0.4 LATU-K/g),
5: K710 (0.9 LATU-K/g)
6: (0.04 LATU-K/g),
7: K916 (0.1 LATU-K/g) and
8: K916 (0.2 LATU-K/g).
Highest degradation of phospholipids is marked in bold.

K710 (0.2 LATU-K/g) demonstrates highest hydrolytic activity, attributing to a total phosphor content of approximately 32 ppm, while EDS 226 and K916 (0.2 LATU-K/g) reduce total phosphor to 42 and 56 ppm respectively. Comparatively, KLM3' (0.1-0.2 LATU-K/g) has been shown to reduce total phosphor to approximately 47-42 ppm.

Inspecting the specific PL's in the oil, the content increases with increasing concentration of K916, and also somewhat with K710. This may be explained from the fact that some of the non-hydratable phospholipids are withdrawn together with the hydratable phospholipids, when these are washed out. When enzyme concentration is increased, the removal of hydratable PL's is increased. Hence, the removal of non-hydratable PL's naturally slows down.

In conclusion, the present observations clearly illustrate that the lipid acyltransferase mutants are applicable in water degumming, particularly K710.

Analysis of Fatty Acids, Phytosterols and Phytosterol Ester

Figure 45:
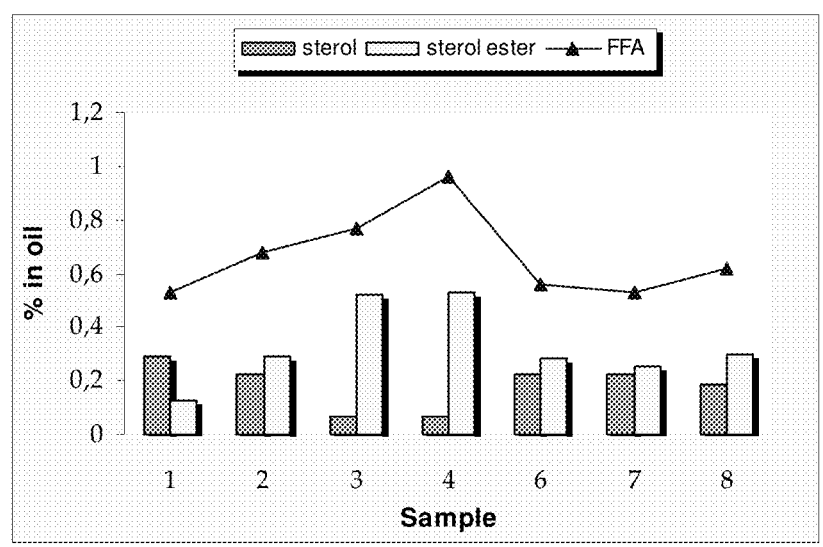
FIG. 45 shows GC-results. Contents (%) of FFA's, phytosterols and phytosterol esters in oils degummed with the lipid acyltransferase mutants. Sample 1: control, 2: EDS 226 (0.1 LATU-K/g), 3: K710 (0.2 LATU-K/g), 4: K710 (0.4 LATU-K/g), 6: K916 (0.04 LATU-K/g), 7: K916 (0.1 LATU-K/g) and 8: K916 (0.2 LATU-K/g)

Analogous content (0.53-0.62%) of free fatty acids (FFA's) is observed in the control and oils, degummed with K916 (0.04, 0.1 and 0.2 LATU-K/g) (FIG. 45). Adding to this the formation of sterol esters is not markedly increased in samples with K916. Hence, it seems that the hydrolytic activity of K916 is not high in low concentrations.

Figure 46:
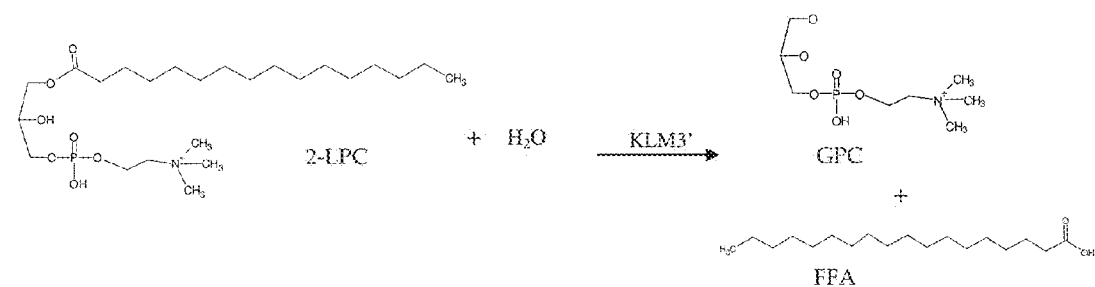
FIG. 46 shows lyso-activity shown as degradation of 2-lyso-phosphatidylcholine (2-LPC) to a free fatty acid (FFA) and glycerophosphatidylcholine (GPC)

On the contrary, increased content of FFA's (0.77-1.08%) is observed with increasing concentration of K710 (0.2 and 0.4 LATU-K/g). This most likely may be explained from high hydrolytic activity of K710. When the phytosterols are depleted, transfer of FFA's to phytosterols is not possible and the enzyme will hydrolyze 2-lyso-phosphatidylcholine into FFA's and glycero-phosphatidylcholine, whereof the FFA's will remain in the oil (FIG. 46). It is likely that K710 has higher lyso-activity than EDS 226 and K916.

The content of FFA's in oils, degummed with the backbone lipid acyltransferase has been reported to range from 0.48% in samples with lowest enzyme concentration (0.1 LATU-K/g) to 0.73% in samples with highest concentrations (0.4 LATU-K/g). In the refinery industry, it is desirable to obtain a minimum of FFA's in the oil, as these will be removed in the deodorization process. Thus, the amount of FFA's may be considered as a loss of oil and should be taken into account in the calculations of oil yield.

Gum Analysis

Analysis of Phospholipid Content

Figure 47:
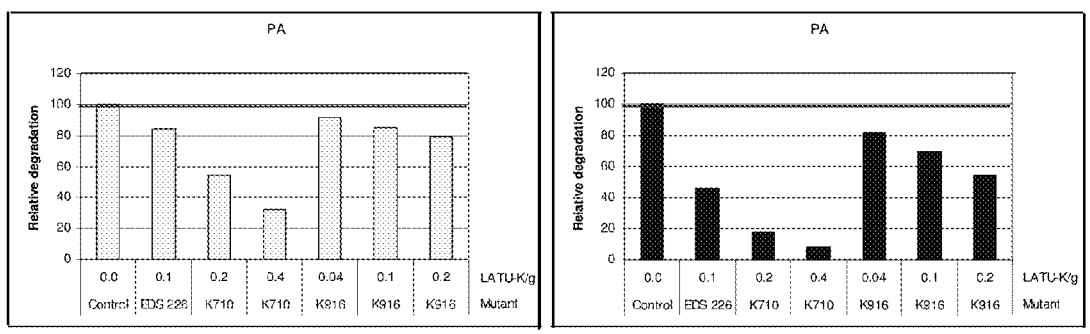
FIG. 47 shows results from TLC analysis of the gum phase. Relative degradation of phospholipids (PE and PA) in gums. Results are based on oils, degummed with different lipid acyltransferase mutants. Sample 1: control, 2: EDS 226 (0.1 LATU-K/g), 3: K710 (0.2 LATU-K/g), 4: K710 (0.4 LATU-K/g), 5: K710 (0.9 LATU-K/g) 6: K916 (0.04 LATU-K/g), 7: K916 (0.1 LATU-K/g) and 8: K916 (0.2 LATU-K/g)

FIG. 47 shows the relative degradation of phosphatidylethanolamine (PE) and phosphatidic acid (PA) in enzymatic gum samples compared to the control. The degradation of phospholipids in the control is set to 100% and the content in enzymatic samples is calculated relatively to the control.

Catalysis of the degradation of non-hydratable phospholipids, PE and PA in particular is pronounced in samples with K710 (0.2 and 0.4 LATU-K/g) compared to the control and samples with EDS 226 (0.1 LATU-K/g) and K916 (0.2 LATU-K/g). Noticeable degradation of PA (≈92%) and PE (≈68%) is succeeded by degumming with K710 in highest concentration (0.4 LATU-K/g). Degradation of PA (63%) and PE (81%) with the backbone lipid acyltransferase (0.4 LATU-K/g) has been observed to be somewhat the opposite.

Analysis of Triglyceride Content

Figure 48:
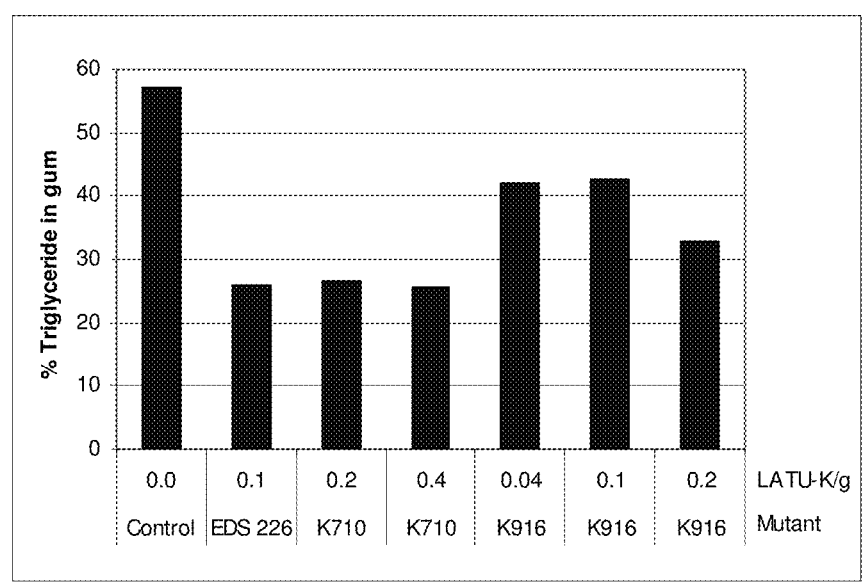
FIG. 48 shows results from TLC analysis of the gum phase. Triglyceride content (%) in gums, obtained from degumming with lipid acyltransferase mutants. Sample 1: control, 2: EDS 226 (0.1 LATU-K/g), 3: K710 (0.2 LATU-K/g), 4: K710 (0.4 LATU-K/g), 5: K710 (0.9 LATU-K/g) 6: K916 (0.04 LATU-K/g), 7: K916 (0.1 LATU-K/g) and 8: K916 (0.2 LATU-K/g).

FIG. 48 shows the triglyceride content in gums. Comparing the content of triglycerides in the gum phase, samples with EDS 226 (0.1 LATU-K/g) and K710 (0.2 and 0.4 LATU-K/g) contain approximately 26% compared to 33-43% in other enzymatic samples and approximately 57% in the control.

Comparable triglyceride content (26-30%) were observed with the backbone lipid acyltransferase (0.1, 0.2, 0.3 and 0.4 LATU-K/g.

K710 demonstrated higher hydrolytic activity on PA, PE and PC compared to EDS 226 and K916 as well as the backbone lipid acyltransferase. The backbone lipid acyltransferase has been shown to reduce total phosphor in the oil to approximately 47-42 ppm, while K710 attributed to a content of 33-32 ppm.

K710 and EDS 226 attributed to an increased oil yield of 2.3-2.5% and K916 to slightly less (2%). Comparatively, the backbone lipid acyltransferase has been shown to increase the oil yield with 1.3-1.6%.

Enzymatic degumming with K710 resulted in 0.77-1.08% FFA's in the oil, which is slightly higher than hydrolysis with the backbone lipid acyltransferase. Presumably K710 is more active on lyso-components than the backbone lipid acyltransferase. The content of FFA's in oils, degummed with EDS 226 and K916 were similar to the control.

In overall, the present experiment shows that the mutant lipid acyltransferase show great promise in degumming oils, particularly K710.

EXAMPLE 4

Converting *E. coli* Thioesterase into an Acyl Transferase Having Properties of *A. salmonicida*

In this example, the *E. coli* thioesterase is modified to provide an altered enzyme that can efficiently catalyze acyl transfer via perhydrolysis or alcoholysis in an aqueous environment.

Four insertions are made in the *E. coli* thioesterase:
A) Replace nucleic acid encoding amino acid residues 11 through 23 corresponding to the amino acid sequence: L S A G Y R M S A S A A W (SEQ ID No. 18)
with nucleic acid encoding the amino acid residues 69 through 92 in *A. salmonicida* lipid acyltransferase encoding the following amino acid sequence: L S D T G K M Y S K M R G Y L P S S P P Y Y E G R F S N G P V W (SEQ ID No. 19).

B) Replace nucleic acid residues 45 through 54 corresponding to the amino acid sequence:
D T S Q Q G L A R L (SEQ ID No. 20)
with DNA encoding the amino acid residues 69 through 92 in of *A. salmonicida* lipid acyltransferase encoding the following amino acid sequence: A T A V A Y N K I S W D P K Y Q V I N N L D Y E (SEQ ID No. 21).

C) Replace nucleic acid encoding amino acid residues 107 through 122 corresponding to the amino acid sequence: I R L P A N Y G R R Y N E A F S (SEQ ID No. 22)
with nucleic acid encoding the amino acid residues 155 through 177 in *A. salmonicida* lipid acyltransferase corresponding the following amino acid sequence: L P D L G Q N P S A R S Q K V V E A V S H V S (SEQ ID No. 23).

D) Replace nucleic acid encoding amino acid residues 142 through 152 corresponding to the amino acid sequence: E E V Y L K P Q W M Q (SEQ ID No. 24)
with nucleic acid encoding amino acid residues 207 through 286 in *A. salmonicida* lipid acyltransferase corresponding to the following sequence: A E M L R D P Q N F G L S D V E N P C Y D G G Y V W K P F A T R S V S T D R Q L S A S P Q E R L A I A G N P L L A Q A V A S P M A R R S A S P L N C E G K M F (SEQ ID No. 17).

The invention is further described by the following numbered paragraphs:

1. A method for preparing a variant lipid acyltransferase enzyme comprising expressing in a host organism a nucleotide sequence which has at least 90% identity with a nucleotide sequence encoding a parent lipid acyltransferase and comprises at least one modification at a position(s) which corresponds in the encoded amino acid sequence to an amino acid(s) located at position 27, 31, 85, 86, 122, 119, 120, 122, 201, 235, 232, 236, 245, 232, 235 and/or 236 wherein the position numbering is defined as that position which when aligned based on primary or tertiary structure corresponds to the same position of the enzyme shown herein as SEQ ID No. 6.

2. A method according to paragraph 1 wherein the at least one modification is in an amino acid residue located in the canyon region and selected from one or more of the following positions 27, 31, 85, 86, 119 and/or 120.

3. A method according to paragraph 2 wherein the at least one modification in the canyon region is in combination with a further modification outside of the canyon region.

4. A method according to any one of paragraphs 1 to 3 wherein the lipid acyltransferase may further comprise at least one further modification may be at one or more of the following positions 23, 81, 82, 289, 229, 227, 233, 33, 207 and/or 130, wherein the position numbering is defined as that position which when aligned based on primary or tertiary structure corresponds to the same position of the enzyme shown herein as SEQ ID No. 6.

5. A method according to any one of the preceding paragraphs wherein said at least one modification is selected from the group consisting of: L31Q, H, N, T, F, Y or C (preferably L31 Q); M27R, G, H, K, Y, D, N, V, C, Q, L, E, S or F (preferably M27V); V85H, R, D or E; I86R, Y, S, V, I, A, T, M, F, C or L (preferably I86S or A); A119T or I; Y120K or E; W122S, L or A (preferably W122L); E201R; Q245S; F235A or V; W232G or S; and/or A236G or E.

6. A method comprising: altering the length of a substrate chain length specificity determining segment that lies immediately N-terminal to the catalytic triad (preferably the Asp residue of the catalytic triad) of a parent enzyme that has an amino acid sequence that is at least 70% identical to the lipid acyltransferase from *A. salmonicida* shown herein as SEQ ID No. 6 or 16, to produce a variant lipid acyltransferase enzyme that has an altered substrate specificity relative to said parent enzyme.

7. A (variant) lipid acyltransferase polypeptide obtained by the method according to any one of the preceding paragraphs.

8. A nucleic acid encoding a lipid acyltransferase enzyme and which nucleotide sequence comprises at least one modification at a position which corresponds in the encoded amino acid sequence to one or more of the following positions: 27, 31, 85, 86, 122, 119, 120, 122, 201, 235, 232, 236, 245, 232, 235, 236, wherein the position numbering is defined as that position which when aligned based on primary or tertiary structure corresponds to the same position of the enzyme shown herein as SEQ ID No. 6.

9. A nucleic acid according to paragraph 8 wherein the nucleic acid encodes a polypeptide having lipid acyltransferase activity and comprising a sequence having at least 94% amino acid sequence identity to the mature region of SEQ ID No. 6 or 16 and which comprises at least one modification at a position located at position 27, 31, 85, 86, 122, 119, 120, 201, 245, 232, 235 and/or 236 wherein the position numbering is defined as that position which when aligned based on primary or tertiary structure corresponds to the same position in the enzyme shown herein as SEQ ID No. 6.

10. A nucleic acid encoding a polypeptide having lipid acyltransferase activity, wherein the nucleotide sequence hybridizes under medium or high stringency conditions over substantially the entire length of SEQ ID No. 10 or SEQ ID No. 25 or a compliment of SEQ ID No. 10 or SEQ ID No. 25, wherein the encoded polypeptide comprises one or more amino acid residues selected from Q, H, N, T, F, Y or C at position 31; R, Y, S, V, I, A, T, M, F, C or L at position 86; R, G, H, K, Y, D, N, V, C, Q, L, E, S or F at position 27; H, R, D, E 85; T or I at position 119; K or E at position 120; S, L, A, F, W, Y, R, H, M or C at position 122; R at position 201; S as position 245; A or V at position 235; G or S at position 232; G or E at position 236, wherein the positions are equivalent amino acid positions with respect of SEQ ID No. 6.

11. A nucleic acid according to paragraph 8 or 9 wherein the at least one modification is in an amino acid residue located in the canyon region and selected from one or more of the following positions 27, 31, 85, 86, 119 and 120.

12. A nucleic acid according to paragraph 11 wherein the at least one modification in the canyon region is in combination with a further modification outside of the canyon region.

13. A nucleic acid according to any one of paragraphs 8 to 12 wherein the nucleic acid comprises at least one further modification at a position which corresponds in the encoded amino acid sequence to one or more of the following positions 23, 81, 82, 289, 229, 227, 233, 33, 207 and/or 130, wherein the position numbering is defined as that position which when aligned based on primary or tertiary structure corresponds to the same position of the enzyme shown herein as SEQ ID No. 6.

14. A nucleic acid according to any one of paragraphs 8 to 13 wherein said at least one modification is selected from the group consisting of: L31Q, H, N, T, F, Y or C (preferably L31 Q); M27R, G, H, K, Y, D, N, V, C, Q, L, E, S or F (preferably M27V); V85H, R, D or E; I86R, Y, S, V, I, A, T, M, F, C or L (preferably I86S or A); A119T or I; Y120K or E; W122S, L or A (preferably W122L); E201R; Q245S; F235A or V; W232G or S; and/or A236G or E.

15. A nucleic acid according to any one of paragraphs 8 to 14 wherein the nucleotide sequence encoding the lipid acyltransferase enzyme and before modification is a nucleotide sequence shown herein as SEQ ID No. 25, SEQ ID No. 10, SEQ ID No. 11, SEQ ID No. 12, SEQ ID No. 13, SEQ ID No. 14 or SEQ ID No. 15; or is a nucleotide sequence which has at least 70% identity (preferably at least 80%, more preferably at least 90%, even more preferably at least 95% identity) with a nucleotide sequence shown herein as SEQ ID No. 25, SEQ ID No. 10, SEQ ID No. 11, SEQ ID No. 12, SEQ ID No. 13, SEQ ID No. 14 or SEQ ID No. 15; or is a nucleotide sequence which is related to SEQ ID No. 25, SEQ ID No. 10, SEQ ID No. 11, SEQ ID No. 12, SEQ ID No. 13, SEQ ID No. 14, SEQ ID No. 15 by the degeneration of the genetic code; or is a nucleotide sequence which hybridizes under medium stringency or high stringency conditions to a nucleotide sequence shown herein as SEQ ID No. 25, SEQ ID No. 10, SEQ ID No. 11, SEQ ID No. 12, SEQ ID No. 13, SEQ ID No. 14 or SEQ ID No. 15.

16. A variant lipid acyltransferase polypeptide encoded by the nucleic acid or nucleotide sequence according to any one of paragraphs 8 to 15.

17. A variant lipid acyltransferase polypeptide encoded by the nucleic acid or nucleotide sequence according to any one of paragraphs 8 to 15 when expressed in a *Bacillus* expression host, in particular in a *B. licheniformis* expression host.

18. A method of producing a polypeptide comprising introducing the nucleic acid of any one of paragraphs 8 to 15 into a host cell (preferably a *Bacillus* expression host, in particular in a *B. licheniformis* expression host), wherein said nucleic acid encoding said polypeptide is operably linked to a regulatory sequence capable of directing expression of a polypeptide encoded by the nucleic acid, culturing the host cell under conditions in which the regulatory sequence directs expression of the polypeptide encoded by the nucleic acid or vector.

19. A polypeptide which has lipid acyltransferase activity and comprises an amino acid sequence which is at least 90% (preferably at least 95%, more preferably at least 98%) identical with the amino acid sequence shown as SEQ ID No. 6 or 16 and comprises one or more modifications at one or more of the following positions: 27, 31, 85, 86, 122, 119, 120, 122, 201, 235, 232, 236, 245 232, 235 and/or 236.

20. A polypeptide according to paragraph 19 wherein the at least one modification is in an amino acid residue located in the canyon region and selected from the group consisting of: 27, 31, 85, 86, 119 and 120.

21. A polypeptide according to paragraph 19 or paragraph 20 wherein the at least one modification in the canyon region is in combination with a further modification outside of the canyon region.

22. A polypeptide according to any one of paragraphs 19 to 21 wherein the lipid acyltransferase may further comprise at least one further modification may be at one or more of the following positions 23, 81, 82, 289, 229, 227, 233, 33, 207 and/or 130, wherein the position numbering is defined as that position which when aligned based on primary or tertiary structure corresponds to the same position of the enzyme shown herein as SEQ ID No. 6.

23. A polypeptide according to any one of paragraphs 19 to 22 wherein said at least one modification is selected from the group consisting of: L31Q, H, N, T, F, Y or C (preferably L31 Q); M27R, G, H, K, Y, D, N, V, C, Q, L, E, S or F (preferably M27V); V85H, R, D or E; I86R, Y, S, V, I, A, T, M, F, C or L (preferably I86S or A); A119T or I; Y120K or E; W122S, L or A (preferably W122L); E201R; Q245S; F235A or V; W232G or S; and/or A236G or E.

24. A polypeptide according to any one of paragraphs 19 to 23 which has lipid acyltransferase activity and comprises an amino acid sequence shown as SEQ ID No. 6 or 16 except for said one or more modifications.

25. A variant lipid acyltransferase polypeptide comprising an amino acid sequence that is at least 70% identical to the lipid acyltransferase from *Aeromonas salmonicida* shown herein as SEQ ID No. 6 or 16, wherein a substrate chain length specificity determining segment that lies immediately N-terminal of the Asp residue of the catalytic triad of said altered lipid acyltransferase has an altered length relative to said lipid acyltransferase from *Aeromonas salmonicida* shown herein as SEQ ID No. 6 or 16.

26. A variant lipid acyltransferase polypeptide according to paragraph 25 wherein the altered lipid acyltransferase comprises an amino acid sequence that is at least 90% identical to the lipid acyltransferase from *Aeromonas salmonicida* shown herein as SEQ ID No. 6 or 16.

27. A method of making a foodstuff comprising adding a polypeptide according to any one of paragraphs 7, 16-17 or 19-26 to one or more ingredients of the foodstuff.

28. A method of making a baked product comprising adding a polypeptide according to any one of paragraphs 7, 16-17 or 19-26 to a dough and baking the dough to make the baked product.

29. Use of a variant lipid acyltransferase enzyme according to any one of paragraphs 7, 16-17 or 19-26 in a process of treating egg or egg-based products to produce lysophospholipids.

30. A process of enzymatic degumming of vegetable or edible oils, comprising treating the edible or vegetable oil with a polypeptide according to any one of paragraphs 7, 16-17 or 19-26 so as to hydrolyze a major part of the polar lipids present therein.

31. A foodstuff or a baked product obtained by the method according to paragraph 27 or paragraph 28.

32. A method as generally described herein with reference to the figures and examples.

33. A nucleic acid as generally described herein with reference to the figures and examples.

34. A variant lipid acyltransferase polypeptide as generally described herein with reference to the figures and examples.

35. A use of a variant lipid acyltransferase polypeptide as generally described herein with reference to the Figures and examples All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

What is claimed is:

1. An isolated variant lipid acyltransferase polypeptide obtained by the method comprising expressing in a host organism a nucleotide sequence encoding a lipid acyltransferase which has at least 80% identity with the amino acid sequence of SEQ ID No. 6 and comprises at least one modification at a position(s) which corresponds in the encoded amino acid sequence to an amino acid(s) located at position 27, 31, 85, 119, 120, 122, 201, 235, 232, 245 and/or 236.

2. An isolated variant lipid acyltransferase polypeptide encoded by a nucleotide sequence-encoding a lipid acyltransferase which has at least 80% identity with the amino acid sequence of SEQ ID No. 6 and comprises at least one modification at a position(s) which corresponds in the encoded amino acid sequence to an amino acid(s) located at position 27, 31, 85, 119, 120, 122, 201, 235, 232, 245 and/or 236; or
    encoded by a nucleotide sequence encoding a lipid acyltransferase enzyme which has at least 80% identity with the amino acid sequence of SEQ ID No. 6 and which nucleotide sequence comprises at least one modification at a position which corresponds in the encoded amino acid sequence to one or more of the following positions: 27, 31, 85, 119, 120, 122, 201, 235, 232, 245 and/or 236 when expressed in a *Bacillus* expression host.

3. An isolated polypeptide which has lipid acyltransferase activity and comprises an amino acid sequence which is at least 80% identical with the amino acid sequence of SEQ ID No. 6 and comprises one or more modifications at one or more of the following positions: 27, 31, 85, 119, 120, 122, 201, 235, 232, 245 and/or 236, wherein before modification the amino acid sequence of the polypeptide comprises an amino acid sequence which is at least 90% identical with the amino acid sequence SEQ ID No. 6 or 16.

4. An isolated polypeptide according to claim 3, wherein the at least one modification is in an amino acid residue located in the canyon region and selected from the group consisting of: 27, 31, 85, 119 and 120; or
    wherein the at least one modification in the canyon region is in combination with a further modification outside of the canyon region; or
    wherein the lipid acyltransferase may further comprise at least one further modification at one or more of the following positions 23, 81, 82, 86, 289, 229, 227, 233, 33, 207 and/or 130; or
    wherein said at least one modification is selected from the group consisting of: L31Q, H, N, T, F, Y or C (preferably L31 Q); M27R, G, H, K, Y, D, N, V, C, Q, L, E, S or F (preferably M27V); V85H, R, D or E; A119T or I; Y120K or E; W122S, L or A (preferably W122L); E201R; Q245S; F235A or V; W232G or S; and/or A236G or E; or
    wherein the isolated polypeptide has lipid acyltransferase activity and comprises the amino acid sequence of SEQ ID No. 6 or 16 except for said one or more modifications.

5. An isolated variant lipid acyltransferase polypeptide comprising an amino acid sequence that is at least 70% identical to the lipid acyltransferase from *Aeromonas salmonicida* comprising the amino acid sequence of SEQ ID No. 6 or 16, wherein a substrate chain length specificity determining segment that lies immediately N-terminal of the Asp residue of the catalytic triad of said altered lipid acyltransferase has an altered length relative to said lipid acyltransferase from *Aeromonas salmonicida* comprising the amino acid sequence of SEQ ID No. 6 or 16.

6. An isolated variant lipid acyltransferase polypeptide according to claim 5 wherein the altered lipid acyltransferase comprises an amino acid sequence that is at least 90% identical to the lipid acyltransferase from *Aeromonas salmonicida* comprising the amino acid sequence of SEQ ID No. 6 or 16.

7. A method of making a foodstuff comprising adding a polypeptide according to claim 1 to one or more ingredients of the foodstuff.

8. A method of making a baked product comprising adding a polypeptide according to claim 1 to a dough and baking the dough to make the baked product.

9. A process of enzymatic degumming of vegetable or edible oils, comprising treating the edible or vegetable oil with a polypeptide according to claim 1 so as to hydrolyse a major part of the polar lipids present therein.

* * * * *

SEQUENCE LISTING

```
<160> NUMBER OF SEQ ID NOS: 54

<210> SEQ ID NO 1
<211> LENGTH: 335
<212> TYPE: PRT
<213> ORGANISM: Aeromonas hydrophila

<400> SEQUENCE: 1

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45
```

Leu Pro Ser Ser Pro Pro Tyr Tyr Glu Gly Arg Phe Ser Asn Gly Pro
 50                  55                  60

Val Trp Leu Glu Gln Leu Thr Lys Gln Phe Pro Gly Leu Thr Ile Ala
 65                  70                  75                  80

Asn Glu Ala Glu Gly Gly Ala Thr Ala Val Ala Tyr Asn Lys Ile Ser
                 85                  90                  95

Trp Asn Pro Lys Tyr Gln Val Ile Asn Asn Leu Asp Tyr Glu Val Thr
             100                 105                 110

Gln Phe Leu Gln Lys Asp Ser Phe Lys Pro Asp Leu Val Ile Leu
         115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Gln Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Ala Asn Gln Tyr Glu Phe Leu Ala His
                325                 330                 335

<210> SEQ ID NO 2
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ile Val Ala Phe Gly Asp Ser Leu Thr Asp Gly Glu Ala Tyr Tyr Gly
 1               5                  10                  15

Asp Ser Asp Gly Gly Gly Trp Gly Ala Gly Leu Ala Asp Arg Leu Thr
             20                  25                  30

Ala Leu Leu Arg Leu Arg Ala Arg Pro Arg Gly Val Asp Val Phe Asn
         35                  40                  45

Arg Gly Ile Ser Gly Arg Thr Ser Asp Gly Arg Leu Ile Val Asp Ala
     50                  55                  60

Leu Val Ala Leu Leu Phe Leu Ala Gln Ser Leu Gly Leu Pro Asn Leu
 65                  70                  75                  80

```
Pro Pro Tyr Leu Ser Gly Asp Phe Leu Arg Gly Ala Asn Phe Ala Ser
            85                  90                  95

Ala Gly Ala Thr Ile Leu Pro Thr Ser Gly Pro Phe Leu Ile Gln Val
        100                 105                 110

Gln Phe Lys Asp Phe Lys Ser Gln Val Leu Glu Leu Arg Gln Ala Leu
        115                 120                 125

Gly Leu Leu Gln Glu Leu Leu Arg Leu Leu Pro Val Leu Asp Ala Lys
        130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
                165                 170                 175

Val Pro Glu Phe Lys Asp Asn Leu Arg Gln Leu Ile Lys Arg Leu Arg
                180                 185                 190

Ser Asn Asn Gly Ala Arg Ile Ile Val Leu Ile Thr Leu Val Ile Leu
            195                 200                 205

Asn Leu Gly Pro Leu Gly Cys Leu Pro Leu Lys Leu Ala Leu Ala Leu
210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
                260                 265                 270

Ala Asp Val Pro Tyr Val Asp Leu Tyr Ser Ile Phe Gln Asp Leu Asp
            275                 280                 285

Gly Ile Gln Asn Pro Ser Ala Tyr Val Tyr Gly Phe Glu Thr Thr Lys
            290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
                340                 345                 350

Gly Tyr Lys Ala Val Ala Glu Ala Leu
            355                 360

<210> SEQ ID NO 3
<211> LENGTH: 335
<212> TYPE: PRT
<213> ORGANISM: Aeromonas hydrophila

<400> SEQUENCE: 3

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
        50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
```

```
                    85                  90                  95

Trp Asn Pro Lys Tyr Gln Val Ile Asn Asn Leu Asp Tyr Glu Val Thr
                100                 105                 110

Gln Phe Leu Gln Lys Asp Ser Phe Lys Pro Asp Asp Leu Val Ile Leu
            115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
                180                 185                 190

His Val Ser Ala Tyr His Asn Gln Leu Leu Asn Leu Ala Arg Gln
                195                 200                 205

Leu Ala Pro Thr Gly Met Val Lys Leu Phe Glu Ile Asp Lys Gln Phe
            210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
                260                 265                 270

Leu Ala Ile Ala Gly Asn Pro Leu Leu Ala Gln Ala Val Ala Ser Pro
            275                 280                 285

Met Ala Ala Arg Ser Ala Ser Thr Leu Asn Cys Glu Gly Lys Met Phe
290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 4
<211> LENGTH: 336
<212> TYPE: PRT
<213> ORGANISM: Aeromonas salmonicida

<400> SEQUENCE: 4

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
                20                  25                  30

Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Tyr Asn Asn Leu Asp Tyr Glu Val Thr
                100                 105                 110

Gln Phe Leu Gln Lys Asp Ser Phe Lys Pro Asp Asp Leu Val Ile Leu
            115                 120                 125
```

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
                180                 185                 190

His Val Ser Ala Tyr His Asn Lys Leu Leu Asn Leu Ala Arg Gln
            195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
            275                 280                 285

Met Ala Arg Arg Ser Ala Ser Pro Leu Asn Cys Glu Gly Lys Met Phe
    290                 295                 300

Trp Asp Gln Val His Pro Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 5
<211> LENGTH: 336
<212> TYPE: PRT
<213> ORGANISM: Aeromonas salmonicida

<400> SEQUENCE: 5

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
                20                  25                  30

Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
                100                 105                 110

Gln Phe Leu Gln Lys Asp Ser Phe Lys Pro Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

```
Gly Gln Asn Pro Ser Ala Arg Ser Gln Lys Val Val Glu Ala Val Ser
                180                 185                 190

His Val Ser Ala Tyr His Asn Lys Leu Leu Leu Asn Leu Ala Arg Gln
            195                 200                 205

Leu Ala Pro Thr Gly Met Val Lys Leu Phe Glu Ile Asp Lys Gln Phe
        210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 6
<211> LENGTH: 318
<212> TYPE: PRT
<213> ORGANISM: Aeromonas salmonicida

<400> SEQUENCE: 6

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
```

```
            210                 215                 220
Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
                260                 265                 270

Arg Arg Ser Ala Ser Pro Leu Asn Cys Glu Gly Lys Met Phe Trp Asp
            275                 280                 285

Gln Val His Pro Thr Thr Val Val His Ala Ala Leu Ser Glu Arg Ala
        290                 295                 300

Ala Thr Phe Ile Glu Thr Gln Tyr Glu Phe Leu Ala His Gly
305                 310                 315

<210> SEQ ID NO 7
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Ala Asp
                20                  25                  30

Ser Arg Pro Ala Phe Ser Arg Ile Val Met Phe Gly Asp Ser Leu Ser
            35                  40                  45

Asp Thr Gly Lys Met Tyr Ser Lys Met Arg Gly Tyr Leu Pro Ser Ser
        50                  55                  60

Pro Pro Tyr Tyr Glu Gly Arg Phe Ser Asn Gly Pro Val Trp Leu Glu
65                  70                  75                  80

Gln Leu Thr Lys Gln Phe Pro Gly Leu Thr Ile Ala Asn Glu Ala Glu
                85                  90                  95

Gly Gly Ala Thr Ala Val Ala Tyr Asn Lys Ile Ser Trp Asn Pro Lys
            100                 105                 110

Tyr Gln Val Ile Asn Asn Leu Asp Tyr Glu Val Thr Gln Phe Leu Gln
        115                 120                 125

Lys Asp Ser Phe Lys Pro Asp Asp Leu Val Ile Leu Trp Val Gly Ala
    130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
        195                 200                 205

Tyr His Asn Gln Leu Leu Leu Asn Leu Ala Arg Gln Leu Ala Pro Thr
    210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
                245                 250                 255
```

-continued

```
Asp Gly Gly Tyr Val Trp Lys Pro Phe Ala Thr Arg Ser Val Ser Thr
                260                 265                 270

Asp Arg Gln Leu Ser Ala Phe Ser Pro Gln Glu Arg Leu Ala Ile Ala
            275                 280                 285

Gly Asn Pro Leu Leu Ala Gln Ala Val Ala Ser Pro Met Ala Arg Arg
        290                 295                 300

Ser Ala Ser Pro Leu Asn Cys Glu Gly Lys Met Phe Trp Asp Gln Val
305                 310                 315                 320

His Pro Thr Thr Val Val His Ala Ala Leu Ser Glu Arg Ala Ala Thr
                325                 330                 335

Phe Ile Ala Asn Gln Tyr Glu Phe Leu Ala His
                340                 345

<210> SEQ ID NO 8
<211> LENGTH: 317
<212> TYPE: PRT
<213> ORGANISM: Aeromonas hydrophila

<400> SEQUENCE: 8

Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Asn Glu Phe Pro Gly Leu Thr Ile Ala Asn Glu
    50                  55                  60

Ala Glu Gly Gly Pro Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Glu Ile Leu Leu Phe Asn Leu Pro Asp Leu Gly Gln
145                 150                 155                 160

Asn Pro Ser Ala Arg Ser Gln Lys Val Val Glu Ala Ala Ser His Val
                165                 170                 175

Ser Ala Tyr His Asn Gln Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Gln Arg Asn Ala
    210                 215                 220

Cys Tyr Gly Gly Ser Tyr Val Trp Lys Pro Phe Ala Ser Arg Ser Ala
225                 230                 235                 240

Ser Thr Asp Ser Gln Leu Ser Ala Phe Asn Pro Gln Glu Arg Leu Ala
                245                 250                 255

Ile Ala Gly Asn Pro Leu Leu Ala Gln Ala Val Ala Ser Pro Met Ala
            260                 265                 270

Ala Arg Ser Ala Ser Thr Leu Asn Cys Glu Gly Lys Met Phe Trp Asp
        275                 280                 285
```

Gln Val His Pro Thr Thr Val Val His Ala Ala Leu Ser Glu Pro Ala
    290                 295                 300

Ala Thr Phe Ile Glu Ser Gln Tyr Glu Phe Leu Ala His
305                 310                 315

<210> SEQ ID NO 9
<211> LENGTH: 318
<212> TYPE: PRT
<213> ORGANISM: Aeromonas salmonicida

<400> SEQUENCE: 9

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His Gly
305                 310                 315

<210> SEQ ID NO 10
<211> LENGTH: 1044
<212> TYPE: DNA

<213> ORGANISM: Aeromonas salmonicida

<400> SEQUENCE: 10

| | | | | | |
|---|---|---|---|---|---|
| atgaaacaac | aaaaacggct | ttacgcccga | ttgctgacgc | tgttatttgc | gctcatcttc | 60 |
| ttgctgcctc | attctgcagc | ttcagcagca | gatacaagac | cggcgtttag | ccggatcgtc | 120 |
| atgtttggag | atagcctgag | cgatacgggc | aaaatgtata | gcaaaatgag | aggctatctt | 180 |
| ccgtcaagcc | cgccgtatta | tgaaggccgc | tttagcaatg | gaccggtctg | gctggaacaa | 240 |
| ctgacgaaac | aatttccggg | actgacgatc | gctaatgaag | cagaaggagg | agcaacagcg | 300 |
| gtcgcctata | acaaaatcag | ctgggacccg | aaatatcagg | tcatcaacaa | cctggactat | 360 |
| gaagtcacac | agtttcttca | gaaagacagc | tttaaaccgg | atgatctggt | catcctttgg | 420 |
| gtcggcgcca | atgattatct | ggcgtatggc | tggaacacag | aacaagatgc | caaaagagtc | 480 |
| agagatgcca | tcagcgatgc | cgctaataga | atggtcctga | acggcgccaa | acaaatcctg | 540 |
| ctgtttaacc | tgccggatct | gggacaaaat | ccgagcgcca | gaagccaaaa | agtcgtcgaa | 600 |
| gcagtcagcc | atgtcagcgc | ctatcataac | aaactgctgc | tgaacctggc | aagacaattg | 660 |
| gcaccgacgg | gaatggttaa | attgtttgaa | attgacaaac | agtttgccga | atgctgaga | 720 |
| gatccgcaaa | attttggcct | gagcgatgtc | gaaaacccgt | gctatgatgg | cggatatgtc | 780 |
| tggaaaccgt | tgccacaag | aagcgtcagc | acggatagac | aactgtcagc | gtttagcccg | 840 |
| caagaaagac | tggcaatcgc | cggaaatccg | cttttggcac | aagcagttgc | ttcaccgatg | 900 |
| gcaagaagat | cagcaagccc | gctgaattgc | gaaggcaaaa | tgttttggga | tcaggtccat | 960 |
| ccgacaacag | ttgtccatgc | tgcccttca | gaaagagcgg | cgacgtttat | cgaaacacag | 1020 |
| tatgaatttc | tggcccatgg | ctga | | | | 1044 |

<210> SEQ ID NO 11
<211> LENGTH: 1005
<212> TYPE: DNA
<213> ORGANISM: Aeromonas hydrophila

<400> SEQUENCE: 11

| | | | | | |
|---|---|---|---|---|---|
| atgaaaaaat | ggtttgtgtg | tttattggga | ttggtcgcgc | tgacagttca | ggcagccgac | 60 |
| agccgtcccg | ccttctcccg | gatcgtgatg | tttggcgaca | gcctctccga | taccggcaag | 120 |
| atgtacagca | agatgcgcgg | ttacctcccc | tccagccccc | cctactatga | gggccgcttc | 180 |
| tccaacgggc | ccgtctggct | ggagcagctg | accaacgagt | tcccgggcct | gaccatagcc | 240 |
| aacgaggcgg | aaggcggacc | gaccgccgtg | gcttacaaca | gatctcctg | gaatcccaag | 300 |
| tatcaggtca | tcaacaacct | ggactacgag | gtcacccagt | tcctgcaaaa | agacagcttc | 360 |
| aagccggacg | atctggtgat | cctctgggtc | ggcgccaacg | actatctggc | ctatggctgg | 420 |
| aacacagagc | aggatgccaa | gcgggtgcgc | gacgccatca | gcgatgcggc | caaccgcatg | 480 |
| gtgctgaacg | cgccaaagga | gatactgctg | ttcaacctgc | cggatctggg | ccagaacccc | 540 |
| tcggcccgca | gccagaaggt | ggtcgaggcg | ccagccatg | tctccgccta | ccacaaccag | 600 |
| ctgctgctga | acctggcacg | ccagctggct | cccaccggca | tggtgaagct | gttcgagatc | 660 |
| gacaagcagt | tgccgagat | gctgcgtgat | ccgcagaact | tcggcctgag | cgaccagagg | 720 |
| aacgcctgct | acggtggcag | ctatgtatgg | aagccgtttg | cctcccgcag | cgccagcacc | 780 |
| gacagccagc | tctccgcctt | caacccgcag | gagcgcctcg | ccatcgcggg | caaccgctg | 840 |
| ctggcccagg | ccgtcgccag | ccccatggct | gcccgcagcg | ccagcaccct | caactgtgag | 900 |
| ggcaagatgt | tctgggatca | ggtccaccc | accactgtcg | tgcacgccgc | cctgagcgag | 960 |

```
cccgccgcca ccttcatcga gagccagtac gagttcctcg cccac            1005
```

<210> SEQ ID NO 12
<211> LENGTH: 1011
<212> TYPE: DNA
<213> ORGANISM: Aeromonas salmonicida

<400> SEQUENCE: 12

```
atgaaaaaat ggtttgtttg tttattgggg ttgatcgcgc tgacagttca ggcagccgac    60
actcgccccg ccttctcccg gatcgtgatg ttcggcgaca gcctctccga taccggcaaa   120
atgtacagca agatgcgcgg ttacctcccc tccagcccgc cctactatga gggccgtttc   180
tccaacggac ccgtctggct ggagcagctg accaagcagt tcccgggtct gaccatcgcc   240
aacgaagcgg aaggcggtgc cactgccgtg gcttacaaca agatctcctg gaatcccaag   300
tatcaggtct acaacaacct ggactacgag gtcacccagt tcttgcagaa agacagcttc   360
aagccggacg atctggtgat cctctgggtc ggtgccaatg actatctggc atatggctgg   420
aatacggagc aggatgccaa gcgagttcgc gatgccatca gcgatgcggc caaccgcatg   480
gtactgaacg gtgccaagca gatactgctg ttcaacctgc cggatctggg ccagaacccg   540
tcagcccgca gtcagaaggt ggtcgaggcg gtcagccatg tctccgccta tcacaacaag   600
ctgctgctga acctggcacg ccagctggcc ccaccggca tggtaaagct gttcgagatc    660
gacaagcaat tgccgagat gctgcgtgat ccgcagaact tcggcctgag cgacgtcgag   720
aaccccctgct acgacggcgg ctatgtgtgg aagccgtttg ccaccccgcag cgtcagcacc   780
gaccgccagc tctccgcctt cagtccgcag gaacgcctcg ccatcgccgg caaccccgctg   840
ctggcacagg ccgttgccag tcctatggcc cgccgcagcg ccagccccct caactgtgag   900
ggcaagatgt tctgggatca ggtacacccg accactgtcg tgcacgcagc cctgagcgag   960
cgcgccgcca ccttcatcga gacccagtac gagttcctcg cccacggatg a           1011
```

<210> SEQ ID NO 13
<211> LENGTH: 1008
<212> TYPE: DNA
<213> ORGANISM: Aeromonas hydrophila

<400> SEQUENCE: 13

```
atgaaaaaat ggtttgtgtg tttattggga ttggtcgcgc tgacagttca ggcagccgac    60
agtcgccccg cctttccccg gatcgtgatg ttcggcgaca gcctctccga taccggcaaa   120
atgtacagca agatgcgcgg ttacctcccc tccagcccgc cctactatga gggccgtttc   180
tccaacggac ccgtctggct ggagcagctg accaaacagt tcccgggtct gaccatcgcc   240
aacgaagcgg aaggcggtgc cactgccgtg gcttacaaca agatctcctg gaatcccaag   300
tatcaggtca tcaacaacct ggactacgag gtcacccagt tcttgcagaa agacagcttc   360
aagccggacg atctggtgat cctctgggtc ggtgccaatg actatctggc ctatggctgg   420
aacacggagc aggatgccaa gcgggttcgc gatgccatca gcgatgcggc caaccgcatg   480
gtactgaacg gtgccaagca gatactgctg ttcaacctgc cggatctggg ccagaacccg   540
tcagctcgca gtcagaaggt ggtcgaggcg gtcagccatg tctccgccta tcacaaccag   600
ctgctgctga acctggcacg ccagctggcc ccaccggca tggtaaagct gttcgagatc    660
gacaagcaat tgccgagat gctgcgtgat ccgcagaact tcggcctgag cgacgtcgag   720
aaccccctgct acgacggcgg ctatgtgtgg aagccgtttg ccaccccgcag cgtcagcacc   780
```

| | |
|---|---|
| gaccgccagc tctccgcctt cagtccgcag gaacgcctcg ccatcgccgg caacccgctg | 840 |
| ctggcacagg ccgttgccag tcctatggcc cgccgcagcg ccagccccct caactgtgag | 900 |
| ggcaagatgt tctgggatca ggtacacccg accactgtcg tgcacgcagc cctgagcgag | 960 |
| cgcgccgcca ccttcatcgc gaaccagtac gagttcctcg cccactga | 1008 |

<210> SEQ ID NO 14
<211> LENGTH: 1011
<212> TYPE: DNA
<213> ORGANISM: Aeromonas salmonicida

<400> SEQUENCE: 14

| | |
|---|---|
| atgaaaaaat ggtttgtttg tttattgggg ttgatcgcgc tgacagttca ggcagccgac | 60 |
| actcgccccg ccttctcccg gatcgtgatg ttcggcgaca gcctctccga taccggcaaa | 120 |
| atgtacagca agatgcgcgg ttacctcccc tccagcccgc cctactatga gggccgtttc | 180 |
| tccaacggac ccgtctggct ggagcagctg accaagcagt tcccgggtct gaccatcgcc | 240 |
| aacgaagcgg aaggcggtgc cactgccgtg gcttacaaca gatctcctg gaatcccaag | 300 |
| tatcaggtca tcaacaacct ggactacgag gtcaccccagt tcttgcagaa agacagcttc | 360 |
| aagccggacg atctggtgat cctctgggtc ggtgccaatg actatctggc atatggctgg | 420 |
| aatacggagc aggatgccaa gcagttcgc gatgccatca gcgatgcggc caaccgcatg | 480 |
| gtactgaacg tgccaagca gatactgctg ttcaacctgc cggatctggg ccagaacccg | 540 |
| tcagcccgca gtcagaaggt ggtcgaggcg gtcagccatg tctccgccta tcacaacaag | 600 |
| ctgctgctga acctggcacg ccagctgccc ccaccggca tggtaaagct gttcgagatc | 660 |
| gacaagcaat ttgccgagat gctgcgtgat ccgcagaact tcggcctgag cgacgtcgag | 720 |
| aaccctgct acgacggcgg ctatgtgtgg aagccgtttg ccacccgcag cgtcagcacc | 780 |
| gaccgccagc tctccgcctt cagtccgcag gaacgcctcg ccatcgccgg caacccgctg | 840 |
| ctggcacagg ccgttgccag tcctatggcc cgccgcagcg ccagccccct caactgtgag | 900 |
| ggcaagatgt tctgggatca ggtacacccg accactgtcg tgcacgcagc cctgagcgag | 960 |
| cgcgccgcca ccttcatcga gacccagtac gagttcctcg cccacggatg a | 1011 |

<210> SEQ ID NO 15
<211> LENGTH: 1047
<212> TYPE: DNA
<213> ORGANISM: Aeromonas hydrophila

<400> SEQUENCE: 15

| | |
|---|---|
| atgtttaagt ttaaaaagaa tttcttagtt ggattatcgg cagctttaat gagtattagc | 60 |
| ttgttttcgg caaccgcctc tgcagctagc gccgacagcc gtcccgcctt ttccggatc | 120 |
| gtgatgttcg gcgacagcct ctccgatacc ggcaaaatgt acagcaagat gcgcggttac | 180 |
| ctcccctcca gcccgcccta ctatgagggc cgtttctcca acggacccgt ctggctggag | 240 |
| cagctgacca aacagttccc gggtctgacc atcgccaacg aagcggaagg cggtgccact | 300 |
| gccgtggctt acaacaagat ctcctggaat cccaagtatc aggtcatcaa caacctggac | 360 |
| tacgaggtca cccagttctt gcagaaagac agcttcaagc cggacgatct ggtgatcctc | 420 |
| tgggtcggtg ccaatgacta tctggcctat ggctggaaca cggagcagga tgccaagcgg | 480 |
| gttcgcgatg ccatcagcga tgcggccaac cgcatggtac tgaacggtgc caagcagata | 540 |
| ctgctgttca acctgccgga tctgggccag aacccgtcag ctcgcagtca gaaggtggtc | 600 |
| gaggcggtca gccatgtctc cgcctatcac aaccagctgc tgctgaacct ggcacgccag | 660 |

```
ctggccccca ccggcatggt aaagctgttc gagatcgaca agcaatttgc cgagatgctg      720
cgtgatccgc agaacttcgg cctgagcgac gtcgagaacc cctgctacga cggcggctat      780
gtgtggaagc cgtttgccac ccgcagcgtc agcaccgacc gccagctctc cgccttcagt      840
ccgcaggaac gcctcgccat cgccggcaac ccgctgctgg cacaggccgt tgccagtcct      900
atggcccgcc gcagcgccag ccccctcaac tgtgagggca agatgttctg ggatcaggta      960
cacccgacca ctgtcgtgca cgcagccctg agcgagcgcg ccgccacctt catcgcgaac     1020
cagtacgagt tcctcgccca ctgatga                                          1047
```

<210> SEQ ID NO 16
<211> LENGTH: 280
<212> TYPE: PRT
<213> ORGANISM: Aeromonas salmonicida

<400> SEQUENCE: 16

```
Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
                20                  25                  30

Ser Ser Pro Pro Tyr Tyr Glu Gly Arg Phe Ser Asn Gly Pro Val Trp
            35                  40                  45

Leu Glu Gln Leu Thr Lys Gln Phe Pro Gly Leu Thr Ile Ala Asn Glu
        50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Arg Ser Ala Ser Pro
225                 230                 235                 240

Leu Asn Cys Glu Gly Lys Met Phe Trp Asp Gln Val His Pro Thr Thr
                245                 250                 255

Val Val His Ala Ala Leu Ser Glu Arg Ala Ala Thr Phe Ile Glu Thr
            260                 265                 270

Gln Tyr Glu Phe Leu Ala His Gly
        275                 280
```

<210> SEQ ID NO 17

```
<211> LENGTH: 79
<212> TYPE: PRT
<213> ORGANISM: Aeromonas salmonicida

<400> SEQUENCE: 17

Ala Glu Met Leu Arg Asp Pro Gln Asn Phe Gly Leu Ser Asp Val Glu
1               5                   10                  15

Asn Pro Cys Tyr Asp Gly Gly Tyr Val Trp Lys Pro Phe Ala Thr Arg
            20                  25                  30

Ser Val Ser Thr Asp Arg Gln Leu Ser Ala Ser Pro Gln Glu Arg Leu
        35                  40                  45

Ala Ile Ala Gly Asn Pro Leu Leu Ala Gln Ala Val Ala Ser Pro Met
    50                  55                  60

Ala Arg Arg Ser Ala Ser Pro Leu Asn Cys Glu Gly Lys Met Phe
65                  70                  75

<210> SEQ ID NO 18
<211> LENGTH: 13
<212> TYPE: PRT
<213> ORGANISM: Escherichia coli

<400> SEQUENCE: 18

Leu Ser Ala Gly Tyr Arg Met Ser Ala Ser Ala Ala Trp
1               5                   10

<210> SEQ ID NO 19
<211> LENGTH: 32
<212> TYPE: PRT
<213> ORGANISM: Aeromonas salmonicida

<400> SEQUENCE: 19

Leu Ser Asp Thr Gly Lys Met Tyr Ser Lys Met Arg Gly Tyr Leu Pro
1               5                   10                  15

Ser Ser Pro Pro Tyr Tyr Glu Gly Arg Phe Ser Asn Gly Pro Val Trp
            20                  25                  30

<210> SEQ ID NO 20
<211> LENGTH: 10
<212> TYPE: PRT
<213> ORGANISM: Escherichia coli

<400> SEQUENCE: 20

Asp Thr Ser Gln Gln Gly Leu Ala Arg Leu
1               5                   10

<210> SEQ ID NO 21
<211> LENGTH: 24
<212> TYPE: PRT
<213> ORGANISM: Aeromonas salmonicida

<400> SEQUENCE: 21

Ala Thr Ala Val Ala Tyr Asn Lys Ile Ser Trp Asp Pro Lys Tyr Gln
1               5                   10                  15

Val Ile Asn Asn Leu Asp Tyr Glu
            20

<210> SEQ ID NO 22
<211> LENGTH: 16
<212> TYPE: PRT
<213> ORGANISM: Escherichia coli

<400> SEQUENCE: 22
```

```
Ile Arg Leu Pro Ala Asn Tyr Gly Arg Arg Tyr Asn Glu Ala Phe Ser
1               5                   10                  15
```

<210> SEQ ID NO 23
<211> LENGTH: 23
<212> TYPE: PRT
<213> ORGANISM: Aeromonas salmonicida

<400> SEQUENCE: 23

```
Leu Pro Asp Leu Gly Gln Asn Pro Ser Ala Arg Ser Gln Lys Val Val
1               5                   10                  15

Glu Ala Val Ser His Val Ser
            20
```

<210> SEQ ID NO 24
<211> LENGTH: 11
<212> TYPE: PRT
<213> ORGANISM: Escherichia coli

<400> SEQUENCE: 24

```
Glu Glu Val Tyr Leu Lys Pro Gln Trp Met Gln
1               5                   10
```

<210> SEQ ID NO 25
<211> LENGTH: 954
<212> TYPE: DNA
<213> ORGANISM: Aeromonas salmonicida

<400> SEQUENCE: 25

```
gacactcgcc ccgccttctc ccggatcgtg atgttcggcg acagcctctc cgataccggc      60
aaaatgtaca gcaagatgcg cggttacctc ccctccagcc cgccctacta tgagggccgt     120
ttctccaacg gacccgtctg gctggagcag ctgaccaagc agttcccggg tctgaccatc     180
gccaacgaag cggaaggcgg tgccactgcc gtggcttaca acaagatctc ctggaccccc     240
aagtatcagg tcatcaacaa cctggactac gaggtcaccc agttcttgca gaaagacagc     300
ttcaagccgg acgatctggt gatcctctgg gtcggtgcca atgactatct ggcatatggc     360
tggaatacgg agcaggatgc caagcgagtt cgcgatgcca tcagcgatgc ggccaaccgc     420
atggtactga acggtgccaa gcagatactg ctgttcaacc tgccggatct gggccagaac     480
ccgtcagccc gcagtcagaa ggtggtcgag gcggtcagcc atgtctccgc ctatcacaac     540
aagctgctgc tgaacctggc acgccagctg gccccaccg gcatggtaaa gctgttcgag     600
atcgacaagc aatttgccga gatgctgcgt gatccgcaga acttcggcct gagcgacgtc     660
gagaacccct gctacgacgg cggctatgtg tggaagccgt ttgccacccg cagcgtcagc     720
accgaccgcc agctctccgc cttcagtccg caggaacgcc tcgccatcgc cggcaacccg     780
ctgctggcac aggccgttgc cagtcctatg gcccgccgca gcgccagccc cctcaactgt     840
gagggcaaga tgttctggga tcaggtacac ccgaccactg tcgtgcacgc agccctgagc     900
gagcgcgccg ccaccttcat cgagacccag tacgagttcc tcgcccacgg atga          954
```

<210> SEQ ID NO 26
<211> LENGTH: 230
<212> TYPE: PRT
<213> ORGANISM: Aspergillus aculeatus

<400> SEQUENCE: 26

```
Thr Thr Val Tyr Leu Ala Gly Asp Ser Thr Met Ala Lys Asn Gly Gly
1               5                   10                  15
```

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
        35                  40                  45

Thr Arg Glu Gly Arg Phe Glu Asn Ile Ala Asp Val Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
    130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
        195                 200                 205

Leu Lys Ala Val Val Cys Thr Gly Thr Ser Leu Lys Ser Val Leu Thr
    210                 215                 220

Thr Thr Ser Phe Glu Gly
225                 230

<210> SEQ ID NO 27
<211> LENGTH: 184
<212> TYPE: PRT
<213> ORGANISM: Escherichia coli

<400> SEQUENCE: 27

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180

<210> SEQ ID NO 28
<211> LENGTH: 308
<212> TYPE: PRT
<213> ORGANISM: Aeromonas hydrophila

<400> SEQUENCE: 28

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Asn Glu Phe Pro
            35                  40                  45

Gly Leu Thr Ile Ala Asn Glu Ala Glu Gly Pro Thr Ala Val Ala
        50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala Ala Thr Phe Ile Glu Ser Gln Tyr Glu
    290                 295                 300

Phe Leu Ala His
305

<210> SEQ ID NO 29
<211> LENGTH: 232
<212> TYPE: PRT

<213> ORGANISM: Aspergillus aculeatus

<400> SEQUENCE: 29

```
Thr Thr Val Tyr Leu Ala Gly Asp Ser Thr Met Ala Lys Asn Gly Gly
1               5                   10                  15
Gly Ser Gly Thr Asn Gly Trp Gly Glu Tyr Leu Ala Ser Tyr Leu Ser
            20                  25                  30
Ala Thr Val Val Asn Asp Ala Val Ala Gly Arg Ser Ala Arg Ser Tyr
        35                  40                  45
Thr Arg Glu Gly Arg Phe Glu Asn Ile Ala Asp Val Val Thr Ala Gly
    50                  55                  60
Asp Tyr Val Ile Val Glu Phe Gly His Asn Asp Gly Gly Ser Leu Ser
65                  70                  75                  80
Thr Asp Asn Gly Arg Thr Asp Cys Ser Gly Thr Gly Ala Glu Val Cys
                85                  90                  95
Tyr Ser Val Tyr Asp Gly Val Asn Glu Thr Ile Leu Thr Phe Pro Ala
            100                 105                 110
Tyr Leu Glu Asn Ala Ala Lys Leu Phe Thr Ala Lys Gly Ala Lys Val
        115                 120                 125
Ile Leu Ser Ser Gln Thr Pro Asn Asn Pro Trp Glu Thr Gly Thr Phe
    130                 135                 140
Val Asn Ser Pro Thr Arg Phe Val Glu Tyr Ala Glu Leu Ala Ala Glu
145                 150                 155                 160
Val Ala Gly Val Glu Tyr Val Asp His Trp Ser Tyr Val Asp Ser Ile
                165                 170                 175
Tyr Glu Thr Leu Gly Asn Ala Thr Val Asn Ser Tyr Phe Pro Ile Asp
            180                 185                 190
His Thr His Thr Ser Pro Ala Gly Ala Glu Val Val Ala Glu Ala Phe
        195                 200                 205
Leu Lys Ala Val Val Cys Thr Gly Thr Ser Leu Lys Ser Val Leu Thr
    210                 215                 220
Thr Thr Ser Phe Glu Gly Thr Cys
225                 230
```

<210> SEQ ID NO 30
<211> LENGTH: 167
<212> TYPE: PRT
<213> ORGANISM: Escherichia coli

<400> SEQUENCE: 30

```
Leu Leu Ile Leu Gly Asp Ser Leu Ser Ala Gly Tyr Arg Met Ser Ala
1               5                   10                  15
Ser Ala Ala Trp Pro Ala Leu Leu Asn Asp Lys Trp Gln Ser Lys Thr
            20                  25                  30
Ser Val Val Asn Ala Ser Ile Ser Gly Asp Thr Ser Gln Gln Gly Leu
        35                  40                  45
Ala Arg Leu Pro Ala Leu Leu Lys Gln His Gln Pro Arg Trp Val Leu
    50                  55                  60
Val Glu Leu Gly Gly Asn Asp Gly Leu Arg Gly Phe Gln Pro Gln Gln
65                  70                  75                  80
Thr Glu Gln Thr Leu Arg Gln Ile Leu Gln Asp Val Lys Ala Ala Asn
                85                  90                  95
Ala Glu Pro Leu Leu Met Gln Ile Arg Leu Pro Ala Asn Tyr Gly Arg
            100                 105                 110
Arg Tyr Asn Glu Ala Phe Ser Ala Ile Tyr Pro Lys Leu Ala Lys Glu
```

```
              115                 120                 125

Phe Asp Val Pro Leu Leu Pro Phe Met Glu Glu Val Tyr Leu Lys
    130                 135                 140

Pro Gln Trp Met Gln Asp Asp Gly Ile His Pro Asn Arg Asp Ala Gln
145                 150                 155                 160

Pro Phe Ile Ala Asp Trp Met
                165

<210> SEQ ID NO 31
<211> LENGTH: 295
<212> TYPE: PRT
<213> ORGANISM: Aeromonas hydrophila

<400> SEQUENCE: 31

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
                20                  25                  30

Phe Ser Asn Gly Pro Val Trp Leu Glu Gln Leu Thr Asn Glu Phe Pro
            35                  40                  45

Gly Leu Thr Ile Ala Asn Glu Ala Glu Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
                100                 105                 110

Trp Asn Thr Glu Gln Asp Ala Lys Arg Val Arg Asp Ala Ile Ser Asp
            115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
    195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
    275                 280                 285

Ala Ala Leu Ser Glu Pro Ala
    290                 295

<210> SEQ ID NO 32
<211> LENGTH: 50
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Arg Pro Ala Phe Ser Arg Ile Val Met Phe Gly Asp Ser Leu Ser Asp
1               5                   10                  15

Thr Gly Lys Met Tyr Ser Lys Met Arg Gly Tyr Leu Pro Ser Ser Pro
            20                  25                  30

Pro Tyr Tyr Glu Gly Arg Phe Ser Asn Gly Pro Val Trp Leu Glu Gln
        35                  40                  45

Leu Thr
    50

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Pro Gly Leu Thr Ile Ala Asn Glu Ala Glu Gly Gly
1               5                   10

<210> SEQ ID NO 34
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Thr Ala Val Ala Tyr Asn Lys Ile Ser Trp Asn Pro Lys Tyr Gln Val
1               5                   10                  15

Ile Asn Asn Leu Asp Tyr Glu Val Thr Gln Phe Leu Gln Lys Asp Ser
            20                  25                  30

Phe Lys Pro Asp Asp Leu Val Ile Leu Trp Val Gly Ala Asn Asp Tyr
        35                  40                  45

Leu Ala Tyr Gly Trp Asn Thr Glu Gln Asp Ala Lys Arg Val Arg Asp
    50                  55                  60

Ala Ile Ser Asp Ala Ala Asn Arg Met Val Leu Asn Gly Ala Lys
65                  70                  75

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Leu Leu Phe Asn Leu Pro Asp Leu Gly Gln Asn Pro Ser Ala Arg
1               5                   10                  15

Ser Gln Lys Val Val Glu Ala
            20

<210> SEQ ID NO 36
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser His Val Ser Ala Tyr His Asn
1               5

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Leu Leu Leu Asn Leu Ala Arg Gln Leu Ala Pro Thr Gly Met Val Lys
1               5                   10                  15

Leu Phe Glu Ile Asp Lys Gln Phe Ala Glu Met Leu Arg Asp Pro Gln
            20                  25                  30

Asn Phe Gly Leu Ser Asp
            35

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Val Trp Lys Pro Phe Ala
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Leu Ser Ala Phe
1               5

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Gln Glu Arg Leu Ala Ile Ala Gly Asn Pro Leu Leu Ala Gln Ala
1               5                   10                  15

Val Ala Ser Pro Met Ala
            20

<210> SEQ ID NO 41
```

<210> SEQ ID NO 41 (implied continuation)
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Ala Ser
1

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Asn Cys Glu Gly Lys Met Phe Trp Asp Gln Val His Pro Thr Thr
1               5                   10                  15

Val Val His Ala Ala Leu Ser Glu
            20

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Ala Thr Phe Ile
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Tyr Glu Phe Leu Ala His
1               5

<210> SEQ ID NO 45
<211> LENGTH: 1225
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (101)..(1141)

<400> SEQUENCE: 45
gcttttcttt tggaagaaaa tatagggaaa atggtacttg ttaaaaattc ggaatattta      60
tacaatatca tatgtttcac attgaaaggg gaggagaatc atg aaa caa caa aaa     115
                                             Met Lys Gln Gln Lys
                                               1               5 cgg ctt tac gcc cga ttg ctg acg ctg tta ttt gcg ctc atc ttc ttg     163
Arg Leu Tyr Ala Arg Leu Leu Thr Leu Leu Phe Ala Leu Ile Phe Leu -continued

```
                        10                  15                  20
ctg cct cat tct gca gct tca gca gca gat aca aga ccg gcg ttt agc      211
Leu Pro His Ser Ala Ala Ser Ala Ala Asp Thr Arg Pro Ala Phe Ser
            25                  30                  35 cgg atc gtc atg ttt gga gat agc ctg agc gat acg ggc aaa atg tat      259
Arg Ile Val Met Phe Gly Asp Ser Leu Ser Asp Thr Gly Lys Met Tyr
        40                  45                  50 agc aaa atg aga ggc tat ctt ccg tca agc ccg ccg tat tat gaa ggc      307
Ser Lys Met Arg Gly Tyr Leu Pro Ser Ser Pro Pro Tyr Tyr Glu Gly
    55                  60                  65 cgc ttt agc aat gga ccg gtc tgg ctg gaa caa ctg acg aaa caa ttt      355
Arg Phe Ser Asn Gly Pro Val Trp Leu Glu Gln Leu Thr Lys Gln Phe
70                  75                  80                  85 ccg gga ctg acg atc gct aat gaa gca gaa gga gga gca aca gcg gtc      403
Pro Gly Leu Thr Ile Ala Asn Glu Ala Glu Gly Gly Ala Thr Ala Val
                90                  95                 100 gcc tat aac aaa atc agc tgg gac ccg aaa tat cag gtc atc aac aac      451
Ala Tyr Asn Lys Ile Ser Trp Asp Pro Lys Tyr Gln Val Ile Asn Asn
            105                 110                 115 ctg gac tat gaa gtc aca cag ttt ctt cag aaa gac agc ttt aaa ccg      499
Leu Asp Tyr Glu Val Thr Gln Phe Leu Gln Lys Asp Ser Phe Lys Pro
        120                 125                 130 gat gat ctg gtc atc ctt tgg gtc ggc gcc aat gat tat ctg gcg tat      547
Asp Asp Leu Val Ile Leu Trp Val Gly Ala Asn Asp Tyr Leu Ala Tyr
    135                 140                 145 ggc tgg aac aca gaa caa gat gcc aaa aga gtc aga gat gcc atc agc      595
Gly Trp Asn Thr Glu Gln Asp Ala Lys Arg Val Arg Asp Ala Ile Ser
150                 155                 160                 165 gat gcc gct aat aga atg gtc ctg aac ggc gcc aaa caa atc ctg ctg      643
Asp Ala Ala Asn Arg Met Val Leu Asn Gly Ala Lys Gln Ile Leu Leu
                170                 175                 180 ttt aac ctg ccg gat ctg gga caa aat ccg agc gcc aga agc caa aaa      691
Phe Asn Leu Pro Asp Leu Gly Gln Asn Pro Ser Ala Arg Ser Gln Lys
            185                 190                 195 gtc gtc gaa gca gtc agc cat gtc agc gcc tat cat aac aaa ctg ctg      739
Val Val Glu Ala Val Ser His Val Ser Ala Tyr His Asn Lys Leu Leu
        200                 205                 210 ctg aac ctg gca aga caa ttg gca ccg acg gga atg gtt aaa ttg ttt      787
Leu Asn Leu Ala Arg Gln Leu Ala Pro Thr Gly Met Val Lys Leu Phe
    215                 220                 225 gaa att gac aaa cag ttt gcc gaa atg ctg aga gat ccg caa aat ttt      835
Glu Ile Asp Lys Gln Phe Ala Glu Met Leu Arg Asp Pro Gln Asn Phe
230                 235                 240                 245 ggc ctg agc gat gtc gaa aac ccg tgc tat gat ggc gga tat gtc tgg      883
Gly Leu Ser Asp Val Glu Asn Pro Cys Tyr Asp Gly Gly Tyr Val Trp
                250                 255                 260 aaa ccg ttt gcc aca aga agc gtc agc acg gat aga caa ctg tca gcg      931
Lys Pro Phe Ala Thr Arg Ser Val Ser Thr Asp Arg Gln Leu Ser Ala
            265                 270                 275 ttt agc ccg caa gaa aga ctg gca atc gcc gga aat ccg ctt ttg gca      979
Phe Ser Pro Gln Glu Arg Leu Ala Ile Ala Gly Asn Pro Leu Leu Ala
        280                 285                 290 caa gca gtt gct tca ccg atg gca aga aga tca gca agc ccg ctg aat     1027
Gln Ala Val Ala Ser Pro Met Ala Arg Arg Ser Ala Ser Pro Leu Asn
    295                 300                 305 tgc gaa ggc aaa atg ttt tgg gat cag gtc cat ccg aca aca gtt gtc     1075
Cys Glu Gly Lys Met Phe Trp Asp Gln Val His Pro Thr Thr Val Val
310                 315                 320                 325 cat gct gcc ctt tca gaa aga gcg gcg acg ttt atc gaa aca cag tat     1123
```

His Ala Ala Leu Ser Glu Arg Ala Ala Thr Phe Ile Glu Thr Gln Tyr
               330                 335                 340 gaa ttt ctg gcc cat ggc tgagttaaca gaggacggat ttcctgaagg            1171
Glu Phe Leu Ala His Gly
                345 aaatccgttt ttttatttta agcttggaga caaggtaaag gataaaacct cgag         1225

<210> SEQ ID NO 46
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ser Ala Ala Asp Thr
                20                  25                  30

Arg Pro Ala Phe Ser Arg Ile Val Met Phe Gly Asp Ser Leu Ser Asp
                35                  40                  45

Thr Gly Lys Met Tyr Ser Lys Met Arg Gly Tyr Leu Pro Ser Ser Pro
50              55                  60

Pro Tyr Tyr Glu Gly Arg Phe Ser Asn Gly Pro Val Trp Leu Glu Gln
65                  70                  75                  80

Leu Thr Lys Gln Phe Pro Gly Leu Thr Ile Ala Asn Glu Ala Glu Gly
                85                  90                  95

Gly Ala Thr Ala Val Ala Tyr Asn Lys Ile Ser Trp Asp Pro Lys Tyr
                100                 105                 110

Gln Val Ile Asn Asn Leu Asp Tyr Glu Val Thr Gln Phe Leu Gln Lys
                115                 120                 125

Asp Ser Phe Lys Pro Asp Asp Leu Val Ile Leu Trp Val Gly Ala Asn
                130                 135                 140

Asp Tyr Leu Ala Tyr Gly Trp Asn Thr Glu Gln Asp Ala Lys Arg Val
145                 150                 155                 160

Arg Asp Ala Ile Ser Asp Ala Ala Asn Arg Met Val Leu Asn Gly Ala
                165                 170                 175

Lys Gln Ile Leu Leu Phe Asn Leu Pro Asp Leu Gly Gln Asn Pro Ser
                180                 185                 190

Ala Arg Ser Gln Lys Val Val Glu Ala Val Ser His Val Ser Ala Tyr
                195                 200                 205

His Asn Lys Leu Leu Leu Asn Leu Ala Arg Gln Leu Ala Pro Thr Gly
                210                 215                 220

Met Val Lys Leu Phe Glu Ile Asp Lys Gln Phe Ala Glu Met Leu Arg
225                 230                 235                 240

Asp Pro Gln Asn Phe Gly Leu Ser Asp Val Glu Asn Pro Cys Tyr Asp
                245                 250                 255

Gly Gly Tyr Val Trp Lys Pro Phe Ala Thr Arg Ser Val Ser Thr Asp
                260                 265                 270

Arg Gln Leu Ser Ala Phe Ser Pro Gln Glu Arg Leu Ala Ile Ala Gly
                275                 280                 285

Asn Pro Leu Leu Ala Gln Ala Val Ala Ser Pro Met Ala Arg Arg Ser
                290                 295                 300

Ala Ser Pro Leu Asn Cys Glu Gly Lys Met Phe Trp Asp Gln Val His
305                 310                 315                 320

```
Pro Thr Thr Val Val His Ala Ala Leu Ser Glu Arg Ala Ala Thr Phe
            325                 330                 335

Ile Glu Thr Gln Tyr Glu Phe Leu Ala His Gly
            340                 345

<210> SEQ ID NO 47
<211> LENGTH: 5
<212> TYPE: PRT
<213> ORGANISM: Aeromonas salmonicida

<400> SEQUENCE: 47

Arg Arg Ser Ala Ser
1               5

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Leu, Ala, Val, Ile, Phe, Tyr, His, Gln, Thr,
      Asn, Met or Ser
<220> FEATURE:
<223> OTHER INFORMATION: see specification as filed for detailed
      description of substitutions and preferred embodiments

<400> SEQUENCE: 48

Gly Asp Ser Xaa
1

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ala Asn Asp Tyr
1               5

<210> SEQ ID NO 50
<211> LENGTH: 317
<212> TYPE: PRT
<213> ORGANISM: Aeromonas hydrophila

<400> SEQUENCE: 50

Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95
```

```
Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Gln Leu Leu Leu Asn Leu Ala Arg Gln Leu Ala
            180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Val Glu Asn Pro
            210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
            275                 280                 285

Gln Val His Pro Thr Thr Val Val His Ala Ala Leu Ser Glu Arg Ala
            290                 295                 300

Ala Thr Phe Ile Ala Asn Gln Tyr Glu Phe Leu Ala His
305                 310                 315

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Asn Asp Ala
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Asn Asp Leu
1               5

<210> SEQ ID NO 53
<211> LENGTH: 318
<212> TYPE: PRT
<213> ORGANISM: Artificial Sequence
<220> FEATURE:
<223> OTHER INFORMATION: Description of Artificial Sequence: Synthetic
      consensus polypeptide
```

```
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (54)..(54)
<223> OTHER INFORMATION: Asn or Lys
<220> FEATURE:
<221> NAME/KEY: MOD_RES
<222> LOCATION: (55)..(55)
<223> OTHER INFORMATION: Glu or Gln
<220> FEATURE:
<221> NAME/KEY: MOD_RES
<222> LOCATION: (69)..(69)
<223> OTHER INFORMATION: Pro or Ala
<220> FEATURE:
<221> NAME/KEY: MOD_RES
<222> LOCATION: (149)..(149)
<223> OTHER INFORMATION: Glu or Gln
<220> FEATURE:
<221> NAME/KEY: MOD_RES
<222> LOCATION: (173)..(173)
<223> OTHER INFORMATION: Ala or Val
<220> FEATURE:
<221> NAME/KEY: MOD_RES
<222> LOCATION: (182)..(182)
<223> OTHER INFORMATION: Gln or Lys
<220> FEATURE:
<221> NAME/KEY: MOD_RES
<222> LOCATION: (221)..(221)
<223> OTHER INFORMATION: Gln or Val
<220> FEATURE:
<221> NAME/KEY: MOD_RES
<222> LOCATION: (222)..(222)
<223> OTHER INFORMATION: Arg or Glu
<220> FEATURE:
<221> NAME/KEY: MOD_RES
<222> LOCATION: (224)..(224)
<223> OTHER INFORMATION: Ala or Pro
<220> FEATURE:
<221> NAME/KEY: MOD_RES
<222> LOCATION: (227)..(227)
<223> OTHER INFORMATION: Gly or Asp
<220> FEATURE:
<221> NAME/KEY: MOD_RES
<222> LOCATION: (229)..(229)
<223> OTHER INFORMATION: Ser or Gly
<220> FEATURE:
<221> NAME/KEY: MOD_RES
<222> LOCATION: (237)..(237)
<223> OTHER INFORMATION: Ser or Thr
<220> FEATURE:
<221> NAME/KEY: MOD_RES
<222> LOCATION: (240)..(240)
<223> OTHER INFORMATION: Ala or Val
<220> FEATURE:
<221> NAME/KEY: MOD_RES
<222> LOCATION: (244)..(244)
<223> OTHER INFORMATION: Ser or Arg
<220> FEATURE:
<221> NAME/KEY: MOD_RES
<222> LOCATION: (250)..(250)
<223> OTHER INFORMATION: Asn or Ser
<220> FEATURE:
<221> NAME/KEY: MOD_RES
<222> LOCATION: (273)..(273)
<223> OTHER INFORMATION: Ala or Arg
<220> FEATURE:
<221> NAME/KEY: MOD_RES
<222> LOCATION: (278)..(278)
<223> OTHER INFORMATION: Thr or Pro
<220> FEATURE:
<221> NAME/KEY: MOD_RES
<222> LOCATION: (303)..(303)
<223> OTHER INFORMATION: Pro or Arg
<220> FEATURE:
<221> NAME/KEY: MOD_RES
<222> LOCATION: (309)..(309)
```

<223> OTHER INFORMATION: Glu or Ala
<220> FEATURE:
<221> NAME/KEY: MOD_RES
<222> LOCATION: (310)..(310)
<223> OTHER INFORMATION: Ser, Thr or Asn
<220> FEATURE:
<221> NAME/KEY: MOD_RES
<222> LOCATION: (318)..(318)
<223> OTHER INFORMATION: May or may not be present

<400> SEQUENCE: 53

```
Ala Asp Xaa Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Xaa Xaa Phe Pro Gly Leu Thr Ile Ala Asn Glu
    50                  55                  60

Ala Glu Gly Gly Xaa Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Xaa Ile Leu Leu Phe Asn Leu Pro Asp Leu Gly Gln
145                 150                 155                 160

Asn Pro Ser Ala Arg Ser Gln Lys Val Val Glu Ala Xaa Ser His Val
                165                 170                 175

Ser Ala Tyr His Asn Xaa Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Xaa Xaa Asn Xaa
210                 215                 220

Cys Tyr Xaa Gly Xaa Tyr Val Trp Lys Pro Phe Ala Xaa Arg Ser Xaa
225                 230                 235                 240

Ser Thr Asp Xaa Gln Leu Ser Ala Phe Xaa Pro Gln Glu Arg Leu Ala
                245                 250                 255

Ile Ala Gly Asn Pro Leu Leu Ala Gln Ala Val Ala Ser Pro Met Ala
            260                 265                 270

Xaa Arg Ser Ala Ser Xaa Leu Asn Cys Glu Gly Lys Met Phe Trp Asp
        275                 280                 285

Gln Val His Pro Thr Thr Val Val His Ala Ala Leu Ser Glu Xaa Ala
    290                 295                 300

Ala Thr Phe Ile Xaa Xaa Gln Tyr Glu Phe Leu Ala His Gly
305                 310                 315
```

<210> SEQ ID NO 54
<211> LENGTH: 6
<212> TYPE: PRT
<213> ORGANISM: Artificial Sequence -continued

```
<220> FEATURE:
<223> OTHER INFORMATION: Description of Artificial Sequence: Synthetic
      6xHis tag

<400> SEQUENCE: 54

His His His His His His
1               5
```